(12) United States Patent
Graham

(10) Patent No.: US 7,833,147 B2
(45) Date of Patent: Nov. 16, 2010

(54) PROCESS FOR ENRICHING A POPULATION OF SPERM CELLS

(75) Inventor: Jeffrey A. Graham, Chesterfield, MO (US)

(73) Assignee: Inguran, LLC., Navasota, TX (US)

( * ) Notice: Subject to any disclaimer, the term of this patent is extended or adjusted under 35 U.S.C. 154(b) by 0 days.

(21) Appl. No.: 11/572,376

(22) PCT Filed: Jul. 22, 2005

(86) PCT No.: PCT/US2005/026269

§ 371 (c)(1),
(2), (4) Date: Aug. 7, 2007

(87) PCT Pub. No.: WO2006/012597

PCT Pub. Date: Feb. 2, 2006

(65) Prior Publication Data

US 2008/0039680 A1  Feb. 14, 2008

Related U.S. Application Data

(63) Continuation-in-part of application No. 11/092,313, filed on Mar. 29, 2005, and a continuation-in-part of application No. 11/092,338, filed on Mar. 29, 2005, and a continuation-in-part of application No. 11/092,509, filed on Mar. 29, 2005.

(60) Provisional application No. 60/590,270, filed on Jul. 22, 2004, provisional application No. 60/590,769, filed on Jul. 23, 2004, provisional application No. 60/614,178, filed on Sep. 29, 2004, provisional application No. 60/618,440, filed on Oct. 13, 2004.

(51) Int. Cl.
*A61B 17/43* (2006.01)
(52) U.S. Cl. ...................................................... 600/35
(58) Field of Classification Search ............ 600/33–35; 435/40.5, 173.9
See application file for complete search history.

(56) References Cited

U.S. PATENT DOCUMENTS

| | | |
|---|---|---|
| 3,005,756 A | 10/1961 | Van Demark |
| 3,499,435 A | 3/1970 | Rockwell et al. |
| 3,547,526 A | 12/1970 | Devereux |
| 3,644,128 A | 2/1972 | Lipner |
| 3,661,460 A | 5/1972 | Elking et al. |
| 3,687,806 A | 8/1972 | Van den Bovenkamp |
| 3,710,933 A | 1/1973 | Fulwyler et al. |
| 3,738,759 A | 6/1973 | Dittrich et al. |
| 3,756,459 A | 9/1973 | Bannister |
| 3,761,187 A | 9/1973 | Dittrich et al. |
| 3,761,941 A | 9/1973 | Robertson |
| 3,788,744 A | 1/1974 | Friedman et al. |
| 3,791,384 A | 2/1974 | Richter |
| 3,791,517 A | 2/1974 | Friedman |
| 3,810,010 A | 5/1974 | Thom |
| 3,816,249 A | 6/1974 | Bhattacharya |
| 3,826,364 A | 7/1974 | Bonner et al. |
| 3,829,216 A | 8/1974 | Persidsky |
| 3,833,796 A | 9/1974 | Fetner et al. |
| 3,877,430 A | 4/1975 | Wieder |
| 3,893,766 A | 7/1975 | Hogg |
| 3,894,529 A * | 7/1975 | Shrimpton .................... 600/35 |
| 3,906,929 A * | 9/1975 | Augspurger ................. 600/34 |
| 3,909,744 A | 9/1975 | Wisner et al. |
| 3,916,143 A | 10/1975 | Farrell |
| 3,944,917 A | 3/1976 | Hogg et al. |
| 3,947,093 A | 3/1976 | Goshima et al. |
| 3,960,449 A | 6/1976 | Carleton et al. |
| 3,963,606 A | 6/1976 | Hogg |
| 3,973,003 A | 8/1976 | Colas |
| 3,973,196 A | 8/1976 | Hogg |
| RE29,141 E | 2/1977 | Hogg |
| 4,006,360 A | 2/1977 | Mueller |
| 4,007,087 A | 2/1977 | Ericsson |
| 4,009,260 A | 2/1977 | Ericsson |
| 4,014,611 A | 3/1977 | Simpson et al. |
| 4,056,324 A | 11/1977 | Gohde |
| 4,058,732 A | 11/1977 | Wieder |
| 4,067,965 A | 1/1978 | Bhattacharya |
| 4,070,617 A | 1/1978 | Kachel et al. |
| 4,083,957 A | 4/1978 | Lang |

(Continued)

FOREIGN PATENT DOCUMENTS

BR   9704313   6/1999

(Continued)

OTHER PUBLICATIONS

Abdel-Ghaffar, A. E., et al., "Rabbit Semen Metabolism" in Rabbit Production in Hot Climates' Baselga and Marai (eds); International Conference of Rabbit Production in Hot Climates 1994, p. 305-312.

(Continued)

*Primary Examiner*—Samuel G Gilbert

(57) ABSTRACT

Processes for selectively enriching a population of viable sperm cells with respect to a characteristic without physically sorting the cells are disclosed. The cells contained in such an enriched population benefit from the advantage of not being subjected to a sorting process. Processes of inseminating a female mammal and processes of forming a sperm dispersion utilizing the processes of selectively enriching a population of viable sperm cells are also disclosed.

49 Claims, No Drawings

U.S. PATENT DOCUMENTS

| | | |
|---|---|---|
| 4,085,205 A | 4/1978 | Hancock |
| 4,092,229 A * | 5/1978 | Bhattacharya ................. 435/2 |
| 4,110,604 A | 8/1978 | Haynes et al. |
| 4,148,718 A | 4/1979 | Fulwyler |
| 4,155,831 A | 5/1979 | Bhattacharya |
| 4,162,282 A | 7/1979 | Fulwyler et al. |
| 4,175,662 A | 11/1979 | Zold |
| 4,178,936 A | 12/1979 | Newcomb |
| 4,179,218 A | 12/1979 | Erdmann et al. |
| 4,189,236 A | 2/1980 | Hogg et al. |
| 4,191,749 A | 3/1980 | Bryant |
| 4,200,802 A | 4/1980 | Salzman et al. |
| 4,225,229 A | 9/1980 | Gohde |
| 4,225,405 A | 9/1980 | Lawson |
| 4,230,558 A | 10/1980 | Fulwyler |
| 4,251,733 A | 2/1981 | Hirlman, Jr. |
| 4,255,021 A | 3/1981 | Brunsden |
| 4,263,508 A | 4/1981 | Leary et al. |
| 4,267,268 A | 5/1981 | Nelson, Jr. |
| 4,274,408 A | 6/1981 | Nimrod |
| 4,274,740 A | 6/1981 | Eidenschink et al. |
| 4,276,139 A | 6/1981 | Lawson |
| 4,302,166 A | 11/1981 | Fulwyler et al. |
| 4,317,520 A | 3/1982 | Lombardo et al. |
| 4,318,480 A | 3/1982 | Lombardo et al. |
| 4,318,481 A | 3/1982 | Lombardo et al. |
| 4,318,482 A | 3/1982 | Barry et al. |
| 4,325,483 A | 4/1982 | Lombardo et al. |
| 4,327,177 A | 4/1982 | Shrimpton |
| 4,339,434 A | 7/1982 | Ericsson |
| 4,341,471 A | 7/1982 | Hogg et al. |
| 4,348,107 A | 9/1982 | Leif |
| 4,350,410 A | 9/1982 | Minott |
| 4,352,558 A | 10/1982 | Eisert |
| 4,361,400 A | 11/1982 | Gray et al. |
| 4,362,246 A * | 12/1982 | Adair ......................... 209/3.3 |
| 4,367,043 A | 1/1983 | Sweet et al. |
| 4,395,397 A * | 7/1983 | Shapiro ....................... 424/577 |
| 4,395,676 A | 7/1983 | Hollinger et al. |
| 4,400,764 A | 8/1983 | Kenyon |
| 4,408,877 A | 10/1983 | Lindmo et al. |
| 4,422,761 A | 12/1983 | Frommer |
| 4,448,767 A | 5/1984 | Bryant |
| 4,474,875 A | 10/1984 | Shrimpton |
| 4,487,320 A | 12/1984 | Auer |
| 4,492,436 A | 1/1985 | Bergmann |
| 4,498,766 A | 2/1985 | Unterleitner |
| 4,501,366 A | 2/1985 | Thompson |
| 4,511,661 A | 4/1985 | Goldberg |
| 4,515,274 A | 5/1985 | Hollinger et al. |
| 4,523,809 A | 6/1985 | Taboada et al. |
| 4,538,733 A | 9/1985 | Hoffman |
| 4,545,677 A | 10/1985 | Chupp |
| 4,559,309 A | 12/1985 | Evenson |
| 4,573,796 A | 3/1986 | Martin |
| 4,585,736 A | 4/1986 | Dolbeare et al. |
| 4,598,408 A | 7/1986 | O'Keefe |
| 4,600,302 A | 7/1986 | Sage, Jr. |
| 4,605,558 A | 8/1986 | Shrimpton |
| 4,609,286 A | 9/1986 | Sage, Jr. |
| 4,629,687 A | 12/1986 | Schindler et al. |
| 4,631,483 A | 12/1986 | Proni et al. |
| 4,637,691 A | 1/1987 | Uehara et al. |
| RE32,350 E | 2/1987 | Bhattacharya |
| 4,654,025 A | 3/1987 | Cassou et al. |
| 4,659,185 A | 4/1987 | Aughton |
| 4,660,971 A | 4/1987 | Sage et al. |
| 4,661,913 A | 4/1987 | Wu et al. |
| 4,662,742 A | 5/1987 | Chupp |
| 4,673,288 A | 6/1987 | Thomas et al. |
| 4,673,289 A | 6/1987 | Gaucher |
| 4,680,258 A | 7/1987 | Hammerling et al. |
| 4,683,195 A | 7/1987 | Mullis et al. |
| 4,683,202 A | 7/1987 | Mullis |
| 4,691,829 A | 9/1987 | Auer |
| 4,698,142 A | 10/1987 | Muroi et al. |
| 4,702,598 A | 10/1987 | Böhmer |
| 4,704,891 A | 11/1987 | Recktenwald et al. |
| 4,710,635 A | 12/1987 | Chupp |
| 4,714,680 A | 12/1987 | Civin |
| 4,737,025 A | 4/1988 | Steen |
| 4,744,090 A | 5/1988 | Freiberg |
| 4,749,458 A | 6/1988 | Muroi et al. |
| 4,752,131 A | 6/1988 | Eisenlauer et al. |
| 4,756,427 A | 7/1988 | Gohde et al. |
| 4,758,729 A | 7/1988 | Monnin |
| 4,764,013 A | 8/1988 | Johnston |
| 4,765,737 A | 8/1988 | Harris et al. |
| 4,770,992 A | 9/1988 | den Engh et al. |
| 4,778,593 A | 10/1988 | Yamashita et al. |
| 4,780,406 A | 10/1988 | Dolbeare et al. |
| 4,780,451 A | 10/1988 | Donaldson |
| 4,786,165 A | 11/1988 | Yamamoto et al. |
| 4,790,653 A | 12/1988 | North, Jr. |
| 4,794,086 A | 12/1988 | Kasper et al. |
| 4,796,788 A | 1/1989 | Bond |
| 4,818,103 A | 4/1989 | Thomas et al. |
| 4,831,385 A | 5/1989 | Archer et al. |
| 4,836,038 A | 6/1989 | Baldwyn |
| 4,845,025 A | 7/1989 | Lary et al. |
| 4,846,785 A | 7/1989 | Cassou |
| 4,867,908 A | 9/1989 | Recktenwald et al. |
| 4,871,249 A | 10/1989 | Watson |
| 4,876,458 A | 10/1989 | Takeda et al. |
| 4,877,965 A | 10/1989 | Dandliker et al. |
| 4,887,721 A | 12/1989 | Martin et al. |
| 4,915,501 A | 4/1990 | Steen |
| 4,936,465 A | 6/1990 | Zold |
| 4,942,305 A | 7/1990 | Sommer |
| 4,954,715 A | 9/1990 | Zold |
| 4,957,363 A | 9/1990 | Takeda et al. |
| 4,959,354 A | 9/1990 | Barbetti |
| 4,965,204 A | 10/1990 | Civin |
| 4,979,093 A | 12/1990 | Laine et al. |
| 4,980,277 A | 12/1990 | Junilla |
| 4,981,580 A | 1/1991 | Auer |
| 4,983,038 A | 1/1991 | Ohki et al. |
| 4,987,539 A | 1/1991 | Moore et al. |
| 4,988,619 A | 1/1991 | Pinkel |
| 4,989,977 A | 2/1991 | North, Jr. |
| 4,999,283 A | 3/1991 | Zavos et al. |
| 5,005,981 A | 4/1991 | Schulte et al. |
| 5,007,732 A | 4/1991 | Ohki et al. |
| 5,017,497 A | 5/1991 | de Grooth |
| 5,021,244 A | 6/1991 | Spaulding |
| 5,030,002 A | 7/1991 | North, Jr. |
| 5,034,613 A | 7/1991 | Denk et al. |
| 5,040,890 A | 8/1991 | North, Jr. |
| 5,043,591 A | 8/1991 | Ludlow et al. |
| 5,055,393 A | 10/1991 | Kwoh et al. |
| 5,057,413 A | 10/1991 | Terstappen et al. |
| 5,072,382 A | 12/1991 | Kamentsky |
| 5,076,472 A | 12/1991 | Gross et al. |
| 5,079,959 A | 1/1992 | Miyake et al. |
| 5,084,004 A | 1/1992 | Ranoux |
| 5,087,295 A | 2/1992 | Gross et al. |
| 5,088,816 A | 2/1992 | Tomioka et al. |
| 5,089,714 A | 2/1992 | Ludlow et al. |
| 5,098,657 A | 3/1992 | Blackford et al. |
| 5,101,978 A | 4/1992 | Marcus |
| 5,116,125 A | 5/1992 | Rigler |
| 5,127,729 A | 7/1992 | Oetliker et al. |
| 5,132,548 A | 7/1992 | Borden et al. |
| 5,135,759 A | 8/1992 | Johnson |

| Patent No. | Date | Inventor |
|---|---|---|
| 5,138,181 A | 8/1992 | Lefevre et al. |
| 5,142,140 A | 8/1992 | Yamazaki et al. |
| 5,142,462 A | 8/1992 | Kashima |
| 5,144,224 A | 9/1992 | Larsen |
| 5,150,313 A | 9/1992 | Van den Engh et al. |
| 5,158,889 A | 10/1992 | Hirako et al. |
| 5,159,397 A | 10/1992 | Kosaka et al. |
| 5,159,403 A | 10/1992 | Kosaka |
| 5,162,306 A | 11/1992 | Donaldson |
| 5,167,926 A | 12/1992 | Kimura et al. |
| 5,180,065 A | 1/1993 | Touge et al. |
| 5,182,617 A | 1/1993 | Yoneyama et al. |
| 5,195,979 A | 3/1993 | Schinkel et al. |
| 5,199,576 A | 4/1993 | Corio et al. |
| 5,204,884 A | 4/1993 | Leary et al. |
| 5,215,376 A | 6/1993 | Schulte et al. |
| 5,219,729 A | 6/1993 | Hodgen |
| 5,247,339 A | 9/1993 | Ogino |
| 5,259,593 A | 11/1993 | Orme et al. |
| 5,260,764 A | 11/1993 | Fukuda et al. |
| 5,274,240 A | 12/1993 | Mathies et al. |
| 5,275,787 A | 1/1994 | Yuguchi et al. |
| 5,298,967 A | 3/1994 | Wells |
| 5,315,122 A | 5/1994 | Pinsky et al. |
| 5,316,540 A | 5/1994 | McMannis et al. |
| 5,317,162 A | 5/1994 | Pinsky et al. |
| 5,336,217 A | 8/1994 | Buys et al. |
| 5,346,990 A | 9/1994 | Spaulding |
| RE34,782 E | 11/1994 | Dandliker et al. |
| 5,359,907 A | 11/1994 | Baker et al. |
| 5,366,888 A | 11/1994 | Fry et al. |
| 5,367,474 A | 11/1994 | Auer et al. |
| 5,370,842 A | 12/1994 | Miyazaki et al. |
| 5,371,585 A | 12/1994 | Morgan et al. |
| 5,395,588 A | 3/1995 | North, Jr. et al. |
| 5,400,179 A | 3/1995 | Ito |
| 5,412,466 A | 5/1995 | Ogino |
| 5,437,987 A | 8/1995 | Ten et al. |
| 5,439,362 A | 8/1995 | Spaulding |
| 5,444,527 A | 8/1995 | Kosaka |
| 5,447,841 A | 9/1995 | Gray et al. |
| 5,447,842 A | 9/1995 | Simons |
| 5,452,054 A | 9/1995 | Dewa et al. |
| 5,457,526 A | 10/1995 | Kosaka |
| 5,461,145 A | 10/1995 | Kudo et al. |
| 5,464,581 A | 11/1995 | Van den Engh |
| 5,466,572 A | 11/1995 | Sasaki et al. |
| 5,467,189 A | 11/1995 | Kreikebaum et al. |
| 5,469,375 A | 11/1995 | Kosaka |
| 5,471,294 A | 11/1995 | Ogino |
| 5,471,299 A | 11/1995 | Kaye et al. |
| 5,475,487 A | 12/1995 | Mariella, Jr. et al. |
| 5,480,774 A | 1/1996 | Hew et al. |
| 5,480,775 A | 1/1996 | Ito et al. |
| 5,483,469 A | 1/1996 | Van den Engh et al. |
| 5,488,469 A | 1/1996 | Yamamoto et al. |
| 5,492,534 A | 2/1996 | Atheyde |
| 5,494,795 A | 2/1996 | Guerry et al. |
| 5,495,719 A | 3/1996 | Gray, Jr. |
| 5,496,272 A | 3/1996 | Chung et al. |
| 5,503,994 A | 4/1996 | Shear et al. |
| 5,514,537 A | 5/1996 | Chandler |
| 5,523,573 A | 6/1996 | Hanninen et al. |
| 5,532,155 A | 7/1996 | Ranoux |
| 5,547,849 A | 8/1996 | Baer et al. |
| 5,548,395 A | 8/1996 | Kosaka |
| 5,548,661 A | 8/1996 | Price et al. |
| 5,550,058 A | 8/1996 | Corio et al. |
| 5,556,764 A | 9/1996 | Sizto et al. |
| 5,558,998 A | 9/1996 | Hammond et al. |
| 5,559,032 A | 9/1996 | Pomeroy et al. |
| 5,578,449 A | 11/1996 | Frasch et al. |
| 5,579,159 A | 11/1996 | Ito |
| 5,584,982 A | 12/1996 | Dovichi et al. |
| 5,589,457 A | 12/1996 | Wiltbank |
| 5,596,401 A | 1/1997 | Kusuzawa |
| 5,601,234 A | 2/1997 | Larue |
| 5,601,235 A | 2/1997 | Booker et al. |
| 5,601,533 A | 2/1997 | Hancke et al. |
| 5,602,039 A | 2/1997 | Van den Engh |
| 5,602,349 A | 2/1997 | Van den Engh |
| 5,608,519 A | 3/1997 | Grouley et al. |
| 5,620,842 A | 4/1997 | Davis et al. |
| 5,622,820 A | 4/1997 | Rossi |
| 5,627,037 A | 5/1997 | Ward et al. |
| 5,633,503 A | 5/1997 | Kosaka |
| 5,641,457 A | 6/1997 | Vardanega |
| 5,643,796 A | 7/1997 | Van den Engh et al. |
| 5,650,847 A | 7/1997 | Maltsev et al. |
| 5,658,751 A | 8/1997 | Yue |
| 5,660,997 A | 8/1997 | Spaulding |
| 5,663,048 A | 9/1997 | Winkfein et al. |
| 5,665,315 A | 9/1997 | Robert et al. |
| 5,672,880 A | 9/1997 | Kain |
| 5,674,743 A | 10/1997 | Ulmer |
| 5,675,401 A | 10/1997 | Wangler et al. |
| 5,682,038 A | 10/1997 | Hoffman |
| 5,684,575 A | 11/1997 | Steen |
| 5,687,727 A | 11/1997 | Kraus et al. |
| 5,690,815 A | 11/1997 | Krasnoff et al. |
| 5,690,895 A | 11/1997 | Matsumoto et al. |
| 5,691,133 A | 11/1997 | Critser et al. |
| 5,693,534 A | 12/1997 | Alak et al. |
| 5,696,157 A | 12/1997 | Wang et al. |
| 5,699,152 A | 12/1997 | Fedor et al. |
| 5,700,692 A | 12/1997 | Sweet |
| 5,701,012 A | 12/1997 | Ho |
| 5,707,808 A | 1/1998 | Roslaniec et al. |
| 5,708,868 A | 1/1998 | Ishikawa |
| 5,712,807 A | 1/1998 | Bangham |
| 5,719,666 A | 2/1998 | Fukuda et al. |
| 5,719,667 A | 2/1998 | Miers |
| 5,726,009 A | 3/1998 | Connors et al. |
| 5,726,364 A | 3/1998 | Van den Engh |
| 5,726,751 A | 3/1998 | Altendorf et al. |
| 5,730,941 A | 3/1998 | Lefevre et al. |
| 5,736,330 A | 4/1998 | Fulton |
| 5,739,902 A | 4/1998 | Gjelsnes et al. |
| 5,745,308 A | 4/1998 | Spangenberg |
| 5,747,349 A | 5/1998 | den Engh et al. |
| 5,759,767 A | 6/1998 | Lakowicz et al. |
| 5,777,732 A | 7/1998 | Hanninen et al. |
| 5,780,230 A | 7/1998 | Li et al. |
| 5,786,560 A | 7/1998 | Tatah et al. |
| 5,790,692 A | 8/1998 | Price et al. |
| 5,793,485 A | 8/1998 | Gourley |
| 5,793,842 A | 8/1998 | Schloemer et al. |
| 5,796,112 A | 8/1998 | Ichie |
| 5,798,276 A | 8/1998 | Haugland |
| 5,799,830 A | 9/1998 | Carroll et al. |
| 5,804,436 A | 9/1998 | Okun et al. |
| 5,815,262 A | 9/1998 | Schrof et al. |
| 5,819,948 A | 10/1998 | Van den Engh |
| 5,824,269 A | 10/1998 | Kosaka et al. |
| 5,831,723 A | 11/1998 | Kubota et al. |
| 5,835,262 A | 11/1998 | Iketaki et al. |
| 5,840,504 A | 11/1998 | Blecher |
| 5,844,685 A | 12/1998 | Gontin |
| 5,846,737 A | 12/1998 | Kang |
| 5,866,344 A | 2/1999 | Georgiou |
| 5,868,767 A | 2/1999 | Farley et al. |
| 5,872,627 A | 2/1999 | Miers |
| 5,873,254 A | 2/1999 | Arav |
| 5,874,266 A * | 2/1999 | Palsson .................. 435/173.1 |
| 5,876,942 A | 3/1999 | Cheng et al. |
| 5,880,457 A | 3/1999 | Tomiyama et al. |

| | | |
|---|---|---|
| 5,880,474 A | 3/1999 | Norton et al. |
| 5,883,378 A | 3/1999 | Irish et al. |
| 5,888,730 A | 3/1999 | Gray et al. |
| 5,891,734 A | 4/1999 | Gill et al. |
| 5,893,843 A | 4/1999 | Rodrigues Claro |
| 5,895,764 A | 4/1999 | Sklar et al. |
| 5,895,922 A | 4/1999 | Ho |
| 6,704,313 B1 | 4/1999 | De Resende et al. |
| 5,899,848 A | 5/1999 | Haubrich |
| 5,909,278 A | 6/1999 | Deka et al. |
| 5,912,257 A | 6/1999 | Prasad et al. |
| 5,916,144 A | 6/1999 | Li et al. |
| 5,916,449 A | 6/1999 | Ellwart et al. |
| 5,917,733 A | 6/1999 | Bangham |
| 5,919,360 A | 7/1999 | Contaxis, III et al. |
| 5,919,621 A | 7/1999 | Brown |
| 5,934,885 A | 8/1999 | Farrell et al. |
| 5,962,238 A | 10/1999 | Sizto et al. |
| 5,972,710 A | 10/1999 | Weigl et al. |
| 5,985,216 A | 11/1999 | Rens |
| 5,985,538 A | 11/1999 | Stachecju |
| 5,990,479 A | 11/1999 | Weiss |
| 5,991,028 A | 11/1999 | Cabib et al. |
| 5,998,140 A | 12/1999 | Dervan |
| 5,998,212 A | 12/1999 | Corio et al. |
| 6,002,471 A | 12/1999 | Quake |
| 6,003,678 A | 12/1999 | Van den Engh |
| 6,042,025 A | 3/2000 | Crampton et al. |
| 6,042,249 A | 3/2000 | Spangenberg |
| 6,050,935 A | 4/2000 | Ranoux et al. |
| 6,071,689 A | 6/2000 | Seidel |
| 6,079,836 A | 6/2000 | Burr et al. |
| 6,086,574 A | 7/2000 | Carroll et al. |
| 6,087,352 A | 7/2000 | Trout |
| 6,090,947 A | 7/2000 | Dervan |
| 6,097,485 A | 8/2000 | Lievan |
| 6,111,398 A | 8/2000 | Graham |
| 6,117,068 A | 9/2000 | Gourley et al. |
| 6,119,465 A | 9/2000 | Mullens et al. |
| 6,120,735 A | 9/2000 | Zborowski et al. |
| 6,128,133 A | 10/2000 | Bergmann |
| 6,130,034 A | 10/2000 | Aitken |
| 6,132,961 A | 10/2000 | Gray et al. |
| 6,133,044 A | 10/2000 | Van den Engh |
| 6,133,995 A | 10/2000 | Kubota |
| 6,139,800 A | 10/2000 | Chandler |
| 6,140,121 A | 10/2000 | Ellington et al. |
| 6,143,535 A | 11/2000 | Paisson |
| 6,143,901 A | 11/2000 | Dervan |
| 6,146,837 A | 11/2000 | van de Winkel |
| 6,149,867 A | 11/2000 | Seidel |
| 6,153,373 A | 11/2000 | Benjamin et al. |
| 6,154,276 A | 11/2000 | Mariella, Jr. |
| 6,175,409 B1 | 1/2001 | Nielsen et al. |
| 6,177,277 B1 | 1/2001 | Soini |
| 6,193,647 B1 | 2/2001 | Beebe et al. |
| 6,201,628 B1 | 3/2001 | Basiji et al. |
| 6,207,392 B1 | 3/2001 | Weiss |
| 6,208,411 B1 | 3/2001 | Vaez-Iravani |
| 6,211,477 B1 | 4/2001 | Cardott et al. |
| 6,214,560 B1 | 4/2001 | Yguerabide et al. |
| 6,221,654 B1 | 4/2001 | Quake et al. |
| 6,221,671 B1 | 4/2001 | Groner et al. |
| 6,238,920 B1 | 5/2001 | Nagai et al. |
| 6,247,323 B1 | 6/2001 | Maeda |
| 6,248,590 B1 | 6/2001 | Malachowski |
| 6,256,096 B1 | 7/2001 | Johnson |
| 6,263,745 B1 | 7/2001 | Buchanan |
| 6,283,920 B1 | 9/2001 | Eberle et al. |
| 6,296,810 B1 | 10/2001 | Ulmer |
| 6,309,815 B1 | 10/2001 | Tash |
| 6,316,234 B1 | 11/2001 | Bova |
| 6,317,511 B1 | 11/2001 | Horiuchi |
| 6,322,901 B1 | 11/2001 | Bawendi |
| 6,323,632 B1 | 11/2001 | Husher et al. |
| 6,326,144 B1 | 12/2001 | Bawendi |
| 6,328,071 B1 | 12/2001 | Austin |
| 6,329,158 B1 | 12/2001 | Hoffman et al. |
| 6,332,540 B1 | 12/2001 | Paul et al. |
| 6,357,307 B2 | 3/2002 | Buchanan et al. |
| 6,368,786 B1 | 4/2002 | Saint-Ramon |
| 6,372,422 B1 | 4/2002 | Seidel |
| 6,372,506 B1 | 4/2002 | Norton |
| 6,384,951 B1 | 5/2002 | Basiji et al. |
| 6,395,305 B1 | 5/2002 | Buhr |
| 6,400,453 B1 | 6/2002 | Hansen |
| 6,411,835 B1 | 6/2002 | Modell et al. |
| 6,411,904 B1 | 6/2002 | Chandler |
| 6,416,190 B1 | 7/2002 | Grier |
| 6,423,505 B1 | 7/2002 | Davis |
| 6,423,551 B1 | 7/2002 | Weiss |
| 6,432,630 B1 | 8/2002 | Blankenstein |
| 6,432,638 B2 | 8/2002 | Dervan et al. |
| 6,452,372 B1 | 9/2002 | Husher et al. |
| 6,454,945 B1 | 9/2002 | Weigl et al. |
| 6,456,055 B2 | 9/2002 | Shinabe et al. |
| 6,463,314 B1 | 10/2002 | Haruna |
| 6,465,169 B2 | 10/2002 | Walderich et al. |
| 6,473,176 B2 | 10/2002 | Basiji et al. |
| 6,482,652 B2 | 11/2002 | Furlong et al. |
| 6,489,092 B1 | 12/2002 | Benjamin et al. |
| 6,495,333 B1 | 12/2002 | Willmann et al. |
| 6,495,366 B1 | 12/2002 | Briggs |
| 6,503,698 B1 | 1/2003 | Dobrinsky et al. |
| 6,511,853 B1 | 1/2003 | Kopf-Sill et al. |
| 6,514,722 B2 | 2/2003 | Palsson et al. |
| 6,524,860 B1 | 2/2003 | Seidel |
| 6,528,802 B1 | 3/2003 | Koenig et al. |
| 6,534,308 B1 | 3/2003 | Palsson et al. |
| 6,537,829 B1 | 3/2003 | Zarling et al. |
| 6,540,895 B1 | 4/2003 | Spence et al. |
| 6,563,583 B2 | 5/2003 | Ortyn et al. |
| 6,569,464 B1 * | 5/2003 | Mukherjee et al. .......... 424/520 |
| 6,576,291 B2 | 6/2003 | Bawendi |
| 6,577,387 B2 | 6/2003 | Ross, III et al. |
| 6,580,504 B1 | 6/2003 | Ortyn et al. |
| 6,587,203 B2 | 7/2003 | Colon |
| 6,589,792 B1 | 7/2003 | Malachowski |
| 6,590,911 B1 | 7/2003 | Spinelli et al. |
| 6,596,143 B1 | 7/2003 | Wang et al. |
| 6,596,499 B2 | 7/2003 | Jalink |
| 6,604,435 B2 | 8/2003 | Buchanan et al. |
| 6,613,525 B2 | 9/2003 | Nelson et al. |
| 6,617,107 B1 | 9/2003 | Dean |
| 6,618,143 B2 | 9/2003 | Roche et al. |
| 6,618,679 B2 | 9/2003 | Loehrlein et al. |
| 6,641,708 B1 | 11/2003 | Becker et al. |
| 6,642,018 B1 * | 11/2003 | Koller et al. ................ 435/40.5 |
| 6,658,357 B2 | 12/2003 | Chandler |
| 6,664,550 B2 | 12/2003 | Rader et al. |
| 6,667,830 B1 | 12/2003 | Iketaki et al. |
| 6,671,044 B2 | 12/2003 | Ortyn et al. |
| 6,673,095 B2 | 1/2004 | Nordquist |
| 6,674,525 B2 | 1/2004 | Bardell et al. |
| 6,698,627 B2 | 3/2004 | Garcia et al. |
| 6,700,130 B2 | 3/2004 | Fritz |
| 6,703,621 B2 | 3/2004 | Wolleschensky |
| 6,706,163 B2 | 3/2004 | Seul et al. |
| 6,707,555 B1 | 3/2004 | Kusuzawa et al. |
| 6,713,019 B2 | 3/2004 | Ozasa et al. |
| 6,729,369 B2 | 5/2004 | Neas et al. |
| 6,746,873 B1 | 6/2004 | Buchanan et al. |
| 6,752,298 B2 | 6/2004 | Garcia et al. |
| 6,753,161 B2 | 6/2004 | Koller et al. |
| 6,761,286 B2 | 7/2004 | Py et al. |
| 6,761,288 B2 | 7/2004 | Garcia |

| | | | |
|---|---|---|---|
| 6,767,706 B2 | 7/2004 | Quake | |
| 6,780,377 B2 | 8/2004 | Hall et al. | |
| 6,782,768 B2 | 8/2004 | Buchanan et al. | |
| 6,789,706 B2 | 9/2004 | Abergel et al. | |
| 6,789,750 B1 | 9/2004 | Heldt | |
| 6,793,387 B1 | 9/2004 | Neas et al. | |
| 6,813,017 B1 | 11/2004 | Hoffman et al. | |
| 6,819,411 B1 | 11/2004 | Sharpe et al. | |
| 6,849,394 B2 | 2/2005 | Rozeboom | |
| 6,849,423 B2 | 2/2005 | Mutz et al. | |
| 6,861,265 B1 | 3/2005 | Van den Engh | |
| 6,941,005 B2 | 9/2005 | Lary et al. | |
| 7,015,310 B2 | 3/2006 | Remington | |
| 7,094,527 B2 | 8/2006 | Seidel et al. | |
| 7,105,355 B2 | 9/2006 | Kurabayashi et al. | |
| 7,195,920 B2 | 3/2007 | Seidel et al. | |
| 7,208,265 B1 * | 4/2007 | Schenk | 435/1.1 |
| 7,221,453 B2 | 5/2007 | Sharpe et al. | |
| 7,335,507 B2 * | 2/2008 | Anzar et al. | 435/325 |
| 2001/0006416 A1 | 7/2001 | Johnson | |
| 2002/0047697 A1 | 4/2002 | Husher et al. | |
| 2002/0058332 A1 | 5/2002 | Quake et al. | |
| 2002/0064809 A1 | 5/2002 | Mutz et al. | |
| 2002/0096123 A1 | 7/2002 | Whittier et al. | |
| 2002/0115055 A1 | 8/2002 | Matta | |
| 2002/0119558 A1 | 8/2002 | Seidel | |
| 2002/0131957 A1 | 9/2002 | Gavin | |
| 2002/0171827 A1 | 11/2002 | Van den Engh | |
| 2002/0182590 A1 | 12/2002 | Strange et al. | |
| 2002/0186375 A1 | 12/2002 | Asbury et al. | |
| 2002/0186874 A1 | 12/2002 | Price et al. | |
| 2002/0198928 A1 | 12/2002 | Bukshpan et al. | |
| 2003/0048433 A1 | 3/2003 | Desjonqueres | |
| 2003/0059764 A1 | 3/2003 | Ravkin et al. | |
| 2003/0059945 A1 | 3/2003 | Dzekunov et al. | |
| 2003/0078703 A1 | 4/2003 | Potts | |
| 2003/0096405 A1 | 5/2003 | Takayama et al. | |
| 2003/0098421 A1 | 5/2003 | Ho | |
| 2003/0113765 A1 | 6/2003 | Dempcy | |
| 2003/0119050 A1 | 6/2003 | Shai | |
| 2003/0119206 A1 | 6/2003 | Shai | |
| 2003/0129091 A1 | 7/2003 | Seidel et al. | |
| 2003/0157475 A1 | 8/2003 | Schenk | |
| 2003/0165812 A1 | 9/2003 | Takayama et al. | |
| 2003/0175917 A1 | 9/2003 | Cumming | |
| 2003/0175980 A1 | 9/2003 | Hayenga et al. | |
| 2003/0190681 A1 | 10/2003 | Shai | |
| 2003/0207461 A1 | 11/2003 | Bell et al. | |
| 2003/0209059 A1 | 11/2003 | Kawano | |
| 2004/0005582 A1 | 1/2004 | Shipwast | |
| 2004/0031071 A1 | 2/2004 | Morris et al. | |
| 2004/0034879 A1 | 2/2004 | Rothstein et al. | |
| 2004/0049801 A1 | 3/2004 | Seidel | |
| 2004/0053243 A1 | 3/2004 | Evans | |
| 2004/0055030 A1 | 3/2004 | Maxwell et al. | |
| 2004/0061070 A1 | 4/2004 | Hansen | |
| 2004/0061853 A1 | 4/2004 | Blasenheim | |
| 2004/0062685 A1 | 4/2004 | Norton et al. | |
| 2004/0072278 A1 | 4/2004 | Chou et al. | |
| 2004/0107150 A1 | 6/2004 | Neas et al. | |
| 2004/0132001 A1 | 7/2004 | Seidel et al. | |
| 2005/0003472 A1 | 1/2005 | Anzar et al. | |
| 2005/0011582 A1 | 1/2005 | Haug | |
| 2005/0064383 A1 | 3/2005 | Bashkin et al. | |
| 2005/0112541 A1 | 5/2005 | Durack | |
| 2005/0214733 A1 | 9/2005 | Graham | |
| 2005/0244805 A1 | 11/2005 | Ludwig et al. | |
| 2005/0282245 A1 | 12/2005 | Ludwig et al. | |
| 2006/0118167 A1 | 6/2006 | Neas et al. | |
| 2006/0147894 A1 | 7/2006 | Sowter | |
| 2006/0203226 A1 | 9/2006 | Roche et al. | |
| 2006/0263829 A1 | 11/2006 | Evans et al. | |
| 2006/0281176 A1 | 12/2006 | Seidel et al. | |
| 2007/0026378 A1 | 2/2007 | Schenk | |
| 2007/0026379 A1 | 2/2007 | Seidel et al. | |
| 2007/0042342 A1 | 2/2007 | Seidel et al. | |
| 2007/0092860 A1 | 4/2007 | Schenk | |
| 2007/0099171 A1 | 5/2007 | Schenk | |
| 2007/0099260 A1 | 5/2007 | Seidel et al. | |
| 2007/0117086 A1 | 5/2007 | Evans et al. | |
| 2007/0123461 A1 | 5/2007 | Josephson | |
| 2007/0248976 A1 | 10/2007 | Harding | |

FOREIGN PATENT DOCUMENTS

| | | |
|---|---|---|
| CA | 1029833 | 4/1978 |
| CA | 1 250 808 | 3/1989 |
| CA | 2113957 A1 | 1/1994 |
| CN | ZL 03109426.0 | 12/2005 |
| EP | 0025296 A2 | 3/1981 |
| EP | 0 046 345 A2 | 2/1982 |
| EP | 0 068 404 B1 | 1/1983 |
| EP | 0 026 770 B1 | 3/1983 |
| EP | 0 029 662 B1 | 2/1984 |
| EP | 0 025 296 B1 | 5/1985 |
| EP | 0140616 | 5/1985 |
| EP | 0 158 147 A2 | 10/1985 |
| EP | 0 160 201 A2 | 11/1985 |
| EP | 0 229 814 B1 | 7/1987 |
| EP | 0 246 604 A2 | 11/1987 |
| EP | 0288029 B1 | 4/1988 |
| EP | 0276166 A2 | 7/1988 |
| EP | 0 289 677 A2 | 11/1988 |
| EP | 0 316 173 A1 | 5/1989 |
| EP | 0 317 809 A2 | 5/1989 |
| EP | A-0 366794 | 5/1990 |
| EP | 0 409 293 A2 | 1/1991 |
| EP | 0 461 618 | 12/1991 |
| EP | 0 463 562 A1 | 1/1992 |
| EP | 0468100 A1 | 1/1992 |
| EP | 0474 187 A2 | 3/1992 |
| EP | 0 316 172 B1 | 7/1992 |
| EP | 0 316 171 B1 | 9/1992 |
| EP | 0570102 A1 | 3/1993 |
| EP | 0538786 A | 4/1993 |
| EP | 0 279 000 B1 | 7/1993 |
| EP | 0 553 951 A1 | 8/1993 |
| EP | 0 288 029 B1 | 1/1994 |
| EP | 0 381 694 B1 | 6/1994 |
| EP | 0 361 504 B1 | 7/1994 |
| EP | 606847 A2 | 7/1994 |
| EP | 0 289 200 B2 | 8/1994 |
| EP | 0 555 212 B1 | 10/1994 |
| EP | 0 361 503 B1 | 11/1994 |
| EP | 0 696 731 A2 | 2/1996 |
| EP | 0 705 978 A2 | 4/1996 |
| EP | 0 711 991 A1 | 5/1996 |
| EP | 0 471 758 B1 | 9/1996 |
| EP | 0 736 765 A1 | 10/1996 |
| EP | 0 545 284 B1 | 2/1997 |
| EP | 0 360 487 B1 | 7/1997 |
| EP | 0 412 431 B1 | 10/1997 |
| EP | 0 526 131 B1 | 1/1998 |
| EP | A-0 478155 | 1/1998 |
| EP | 0 822 404 A3 | 2/1998 |
| EP | 0 822 401 A2 | 4/1998 |
| EP | 0 556 748 B1 | 10/1998 |
| EP | 0 430 402 B1 | 1/1999 |
| EP | 0 529 666 B1 | 4/2000 |
| EP | 0 994 342 A3 | 4/2000 |
| EP | 0 752 133 B1 | 6/2000 |
| EP | 1 018 644 A2 | 7/2000 |
| EP | 1 118 268 A1 | 7/2001 |
| EP | 1 147 774 A1 | 10/2001 |
| EP | 0 534 033 B1 | 11/2001 |
| EP | 0 925 494 B1 | 12/2001 |

| | | | | | | |
|---|---|---|---|---|---|---|
| EP | 0 748 316 B1 | 5/2002 | | WO | WO 0129538 | 4/2001 |
| EP | 0 662 124 B1 | 6/2002 | | WO | 0137655 A1 | 5/2001 |
| EP | 1 245 944 A3 | 10/2002 | | WO | WO 01/40765 A2 | 6/2001 |
| EP | 1 249 502 A2 | 10/2002 | | WO | WO 01/40765 A3 | 6/2001 |
| EP | 1250897 A1 | 10/2002 | | WO | WO 01/42757 A2 | 6/2001 |
| EP | 1 380 304 A2 | 1/2004 | | WO | 0151612 A1 | 7/2001 |
| EP | 1 403 633 A3 | 4/2004 | | WO | WO 01/61313 A2 | 8/2001 |
| EP | 1 100 400 B1 | 5/2004 | | WO | 0168110 A | 9/2001 |
| EP | 1 257 168 B1 | 2/2005 | | WO | WO 01/68226 A2 | 9/2001 |
| GB | 1471019 | 4/1977 | | WO | WO 01/71348 A1 | 9/2001 |
| GB | 2 121 976 A | 1/1984 | | WO | WO 01/75161 A2 | 10/2001 |
| GB | 2 122 369 A | 1/1984 | | WO | WO 0175176 | 10/2001 |
| GB | 2 125 181 A | 2/1984 | | WO | 0185913 A1 | 11/2001 |
| GB | 2 136 561 A | 9/1984 | | WO | WO 01/02836 A1 | 11/2001 |
| GB | 2 137 352 A | 10/1984 | | WO | WO 01/85913 A2 | 11/2001 |
| GB | 2145112 A1 | 2/1985 | | WO | WO 01/85913 A3 | 11/2001 |
| GB | 2 144 542 A | 3/1985 | | WO | WO 01/90295 A1 | 11/2001 |
| GB | 2 153 521 A | 8/1985 | | WO | WO 01/95815 A1 | 12/2001 |
| GB | 2 243 681 A | 11/1991 | | WO | WO 02/01189 A1 | 1/2002 |
| GB | 2 360 360 A | 9/2001 | | WO | WO 02/04666 A2 | 1/2002 |
| JP | 61139747 (A) | 6/1986 | | WO | 0219594 A2 | 3/2002 |
| JP | 61159135 (A) | 7/1986 | | WO | WO 02/19943 A1 | 3/2002 |
| JP | 2024535 | 1/1990 | | WO | WO 02/20850 A2 | 3/2002 |
| JP | 4126064 (A) | 4/1992 | | WO | WO 02/21102 A2 | 3/2002 |
| JP | 4126065 (A) | 4/1992 | | WO | WO 02/23163 A1 | 3/2002 |
| JP | 4126066 (A) | 4/1992 | | WO | WO 02/25269 A2 | 3/2002 |
| JP | 4126079 (A) | 4/1992 | | WO | WO 02/26114 A2 | 4/2002 |
| JP | 4126080 (A) | 4/1992 | | WO | WO 02/28311 A1 | 4/2002 |
| JP | 4126081 (A) | 4/1992 | | WO | WO 02/29106 A12 | 4/2002 |
| WO | WO 84/01265 A1 | 4/1984 | | WO | 0241906 A2 | 5/2002 |
| WO | WO 85/04014 A1 | 9/1985 | | WO | 0243574 A3 | 5/2002 |
| WO | WO 88/07198 | 9/1988 | | WO | WO 0241906 A2 | 5/2002 |
| WO | WO 89/04470 A1 | 5/1989 | | WO | WO 02/43486 A1 | 6/2002 |
| WO | WO 89/04471 A1 | 5/1989 | | WO | WO 02/44319 A2 | 6/2002 |
| WO | WO 90/13315 A1 | 11/1990 | | WO | WO 02/052244 A2 | 7/2002 |
| WO | WO 9105236 | 4/1991 | | WO | WO 02/054044 A2 | 7/2002 |
| WO | WO 92/08120 A1 | 5/1992 | | WO | WO 02/057775 A1 | 7/2002 |
| WO | WO 92/17288 A1 | 10/1992 | | WO | WO 02/060880 A1 | 8/2002 |
| WO | WO 93/10803 | 6/1993 | | WO | WO03020877 A2 | 8/2002 |
| WO | WO 9317322 A1 | 9/1993 | | WO | 02077011 A3 | 10/2002 |
| WO | WO 94/22001 A1 | 9/1994 | | WO | WO 02/077637 A1 | 10/2002 |
| WO | WO 96/04542 A1 | 2/1996 | | WO | WO 02/092161 A1 | 11/2002 |
| WO | WO 96/12171 A2 | 4/1996 | | WO | WO 02/092247 A1 | 11/2002 |
| WO | WO 96/12172 | 4/1996 | | WO | WO 03/008102 A1 | 1/2003 |
| WO | WO 96/12173 A1 | 4/1996 | | WO | WO 03/008937 A2 | 1/2003 |
| WO | WO 96/31764 | 10/1996 | | WO | WO 03/012403 A1 | 2/2003 |
| WO | WO 96/33806 A1 | 10/1996 | | WO | WO 03/016875 A2 | 2/2003 |
| WO | WO 97/29354 A1 | 8/1997 | | WO | WO 03/056330 A2 | 7/2003 |
| WO | WO 97/30338 A1 | 8/1997 | | WO | WO 03/056335 A2 | 7/2003 |
| WO | WO 97/35189 A1 | 9/1997 | | WO | WO 03/072765 A1 | 9/2003 |
| WO | WO 97/43620 A1 | 11/1997 | | WO | WO 03/078065 A1 | 9/2003 |
| WO | WO 89/04472 A1 | 5/1998 | | WO | WO 03/078972 A1 | 9/2003 |
| WO | WO 98/34094 A1 | 8/1998 | | WO | WO 04001401 | 12/2003 |
| WO | WO 98/48259 | 10/1998 | | WO | WO 2004/006916 A1 | 1/2004 |
| WO | WO 98/57152 A1 | 12/1998 | | WO | WO 2004/009237 A2 | 1/2004 |
| WO | WO 99/05504 A2 | 2/1999 | | WO | WO 2004/009237 A3 | 1/2004 |
| WO | 9933956 A1 | 7/1999 | | WO | WO 2004/012837 A2 | 2/2004 |
| WO | WO 99/38883 A1 | 8/1999 | | WO | WO 2004/012837 A3 | 2/2004 |
| WO | WO 99/42810 A1 | 8/1999 | | WO | WO 2004/017041 A2 | 2/2004 |
| WO | WO 99/44035 | 9/1999 | | WO | WO 2004/017041 A3 | 2/2004 |
| WO | WO 99/44037 A1 | 9/1999 | | WO | WO 2004/024227 A2 | 3/2004 |
| WO | WO 99/47906 A1 | 9/1999 | | WO | WO 2004/024227 A3 | 3/2004 |
| WO | WO 99/60397 A1 | 11/1999 | | WO | WO 2004/046712 A2 | 6/2004 |
| WO | WO 9957955 | 11/1999 | | WO | WO 2004/059282 A2 | 7/2004 |
| WO | WO 99/61888 A2 | 12/1999 | | WO | 2004087177 A2 | 10/2004 |
| WO | WO 00/06193 A1 | 2/2000 | | WO | 2004088283 A | 10/2004 |
| WO | WO 00/12204 | 3/2000 | | WO | WO 2004/003697 A2 | 10/2004 |
| WO | WO 00/36396 | 6/2000 | | WO | WO 2004/104178 A2 | 12/2004 |
| WO | WO 00/49387 | 8/2000 | | WO | WO 2004/104178 A3 | 12/2004 |
| WO | 0054026 A1 | 9/2000 | | WO | WO 2005/094852 A2 | 10/2005 |
| WO | WO 00/56444 | 9/2000 | | WO | WO 2005/095590 A2 | 10/2005 |
| WO | WO 00/70080 | 11/2000 | | WO | WO 2005/095960 A1 | 10/2005 |
| WO | WO 01/28700 A1 | 4/2001 | | WO | WO 2006/015056 A2 | 2/2006 |

| WO | WO 2006012597 A2 | 2/2006 |
| WO | WO 2006060770 A2 | 8/2006 |
| WO | WO 2007016090 A2 | 2/2007 |

OTHER PUBLICATIONS

Akhtar, S., et al., "Prevalence of Five Stereotypes of Bluetongue Virus in a Rambouillet Sheep Flock in Pakistan", Veterinary Record 136, p. 495. (1995).
Aldrich, S. L., et al., "Parturition and Periparturient Reproductive and Metabolic Hormone Concentration in Prenatally Androgenized Beef Heifers", J. Anim. Sci. 73:3712. (1995).
Amann, R. P. et al., "Issues Affecting Commercialization of Sexed Sperm" Therio. 52:1441. (1999).
Amann, R. P., et al. "Prospects For Sexing Mammalian Sperm," Animal Reproduction Laboratory College of Veterinary Medicine and Biomedical Sciences, Colorado State University. (1982).
Amann, R.P. "Fertilizing Potential Vitro of Semen from Young Beef Bulls Containing a High or Low Percentage of Sperm with a Proximal Droplet" Theriogenology 54: 1499-1515, 2000.
Amann, Rupert P. "Cryopreservation of Sperm" 1999, Encyclopedia of Reproduction 1:733-783.
American Meat and Science Association in Cooperation with National Livestock and Meat Board, "Research Guidelines for Cookery and Sensory Evaluation and Instrumental Tenderness Measurements for Fresh Meat". (1995).
Amoah, E. A. and Gelaye, S., "Biotechnological Advances in Goat Reproduction", J. Anim. Sci. 75(2): 578-585. (1996).
Anderson, V. K., et al., Intrauterine und tiefzervikale Insemination mit Gefriersperma bein Schat (Intrauterine and Deep Cervical Insemination With Frozen Semen in Sheep). Zuchthygiene 8:113-118. (1973).
Arriola, J. and Foote, R.H.: "Glycerolation and Thawing Effects on Bull Spermatozoa frozen in Detergent-Treated Egg Yok and Whole Egg Extenders," J Dairy Sci, 70:1664-1670 (1987).
Asbury, Charles A. "Fluorescence Spectra of DNA Dyes Measured in a Flow Cytometer," University of Washington Feb. 19, 1996.
Bagley, C. P. "Nutritional Management of Replacement Beef Heifers: a Review" J. Anim. Science 71:3155-3163. (1993).
Bailey, C. M. et al., "Nulliparous Versus Primiparous Crossbred Females for Beef", J. Anim. Sci. 69:1403. (1991).
Baker, R.D., et al., "Effect of Volume of Semen, Number of Sperm and Drugs on Transport of Sperm in Artificially Inseminated Gilts", J. Anim. Sci. 27:88-93. (1968).
Bakker Schut, Tom C. "A New Principle of Cell Sorting by Using Selective Electroportation in a Modified Flow Cytometry," University of Twente, Mar. 10, 1990.
Barnes, F. L. and Eyestone, W. H., "Early Cleavage and the Maternal Zygotic Transition in Bovine Embryos", Therio. vol. 33, No. 1, pp. 141-149. (1990).
Batellier, F. et al., "Advances in Cooled Semen Technology" Animal Reproduction Science 68 p. 181-190 (2001).
Becker, S.E. and Johnson, A. L. "Effects of Gonadotropin-Releasing Hormone Infused in a Pulsatile or Continuous Fashion on Serum Gonadotropin Concentrations and Ovulation in the Mare", J. Anim. Sci. 70:1208-1215. (1992).
Bedford, S .J. and Hinrichs, K., "The Effect of Insemination Volume on Pregnancy Rates of Pony Mares", Therio. 42:571-578. (1994).
Behrman, S. J., et al., "Freeze Preservation of Human Sperm" American Journal of Obstetrics and Gynecology vol. 103 (5) p. 654-664 Mar. 1, 1969.
Bellows, R. A., et al., "Cause and Effect Relationships Associated With Calving Difficulty and Calf Birth Weight", J. Anim. Sci. 33:407. (1971).
Berardinelli, J. G., et al., "Source of Progesterolle Prior to Puberty in Beef Heifers". J. Anim. Sci. 49:1276. (1979).
Berger, G. S. "Intratubal Insemination", Fertil. Steril. 48:328-330, (1987).
Bergfeld, E. G., et al., "Ovarian Follicular Development in Prepubertal Heifers is Influenced by Level of Dietary Energy Intake", Bio. of Repro. 51:1051. (1994).
Berry, B. W., et al., "Beef Carcass Maturity Indicators and Palatability Attributes", J. Anim. Sci. 38:507 (1974).
Beyhan, Z., et al., "Sexual Dimorphism in IVF Bovine Embryos Produced by Sperm Sorted by High Speed Flow Cytometry", abstr. Therio. 49(1): 359 (1998).
Beyhan, Z., Et Al., 1999 Sexual Dimorphism in IVM-IVF Bovine Embryos Produced from X and Y Chromosome-Bearing Spermatozoa Sorted By High Speed Flow Cytometry. Theriogenology. 52: 35-48.
Bigos, Martin "Nine Color Eleven Parameter Immunophenotyping Using Three Laser Flow Cytometry," Stanford University Dec. 22, 1998.
Bioxcell, Bovine Sperm Preservation, Advertisement Jun. 28, 2005.
Bond, J., et al., "Growth and Carcass Traits of Open Beef Heifers Versus Beef Heifers That Have Calved", Nutrition Reports International 34:621. 1986.
Boucque, C. V., et al., "Beef-Production With Maiden and Once-Calved Heifers", Livestock Prod. Sci. 7:121. 1980.
Bourdon, R. M. and J. S. Brinks. "Simulated Efficiency of Range Beef—Production III. Culling Strategies and Nontraditional Management-Systems", J. Anim. Sci. 65:963. 1987.
Bracher, V. and Allen, W.R., "Videoendoscopic Examination of the Mare's Uterus: I. Findings in Normal Fertile Mares", Equine Veterinary Journal, vol. 24, p. 274-278. 1992.
Braselton, W. E. and McShan, W. H., "Purification and Properties of Follicle Stimulating and Luteinizing Hormones From Horse Pituitary Glands" Arch. Biochem. Biophys. 139:45-48. 1970.
Braun, J. et al, "Effect of Different Protein Supplements on Motility and Plasma Membrane Integrity of Frozen- Thawed Stallion Spermatozoa", Cryobiology (1995) 32:487-492.
Brethour, J. R. and Jaeger, J. R., "The Single Calf Heifer System", Kansas Agric. Sta. Rep of Progress 570. 1989.
Brinsko, S.P. et al., "Artificial Insemination and Preservation of Semen." Veterinary Clinics of North America:Equine Practice vol. 8 No. 1 Apr. 1992 pp. 205-218.
Bristol, F. "Breeding Behavior of a Stallion at Pasture With 20 Mares in Synchronized Oestrus" J. Reprod. Fertil. Suppl 32:71. 1982.
Brookes, A. J. and O'Byrne, M., "Use of Cow-Heifers in Beef Production" J. of the Royal Agricultural Society of England 126:30. 1965.
Buchanan, B. R., et al, "Insemination of Mares with Low Numbers of Either Unsexed or Sexed Spermatozoa", Therio. vol. 53, p. 1333-1344. 2000.
Buchanan, B.R. "Pregnancy Rates in Mares Following a Single Insemination with a Low Number of Spermatozoa into the Tip of the Uterine Horn" Theriogenology p. 395 1999.
Burns, P. D. and Spitzer, J.C., "Influence of Biostimulation on Reproduction in Postpartum Beef-Cows", J. Anim. Sci. 70:358. 1992.
Burwash, L. D., et al., "Relationship of Duration of Estrus to Pregnancy Rate in Normally Cycling, Non Lactating Mares" J.A.V.M.A. 165:714-716. 1974.
Byerley, D. J., et al., "Pregnancy Rates of Beef Heifers Bred Either on Puberal or Third Estrus". J. Anim. Sci. 65:645. 1987.
Caslick, E. A., "The Vulva and the Vulvo-Vaginal Orifice and its Relation to Genital Health of the Thoroughbred Mare", Cornell Veterinarian, vol. 27, p. 178-187. 1937.
Catt, et al., "Assessment of Ram and Boar Spermatozoa During Cell-Sorting by Flow Cytometry", Reproduction Dom Animal, vol. 32, pp. 251-258. 1997.
Catt, S. L., et al., "Birth of a Male Lamb Derived from an In Vitro Matured Oocyte Fertilized by Intracytoplasmic Injection of a Single Presumptive Male Sperm", Veterinary Record 139, p. 494-495. 1996.
Cave-Penney, Tony, "Sexed Semen Offers Faster Genetic Gain", Farming News, Livestock Supplement, Feb. 1997, p. 28.
Celestron: Telescope Basics: www.celestron.com/tb-2ref/htm; 4 pages, Oct. 20, 2003.
Chandler, J. E., "Videomicroscopic Comparison of Bull Sperm and Leukocyte Chromosome Areas as Related to Gender", J Dairy Sci 73, p. 2129-2135. 1990.
Chandler, J. E., et al, "Bovine Spermatozoal Head Size Variation and Evaluation of a Separation Technique Based on this Size", Therio. 52, p. 1021-1034. 1999.

Chen, S.H. "Effects of Oocyte Activation and Treatment of Spermatozoa on Embryonic Development Following Intracytoplasmic Sperm Injection in Cattle" Theriogenology 48: 1265-1273, 1997.

Chen, Y. et al., Survival of Bull Spermatozoa Seeded and Frozen at Different Rates in Egg Yolk-Tris and Whole Milk Extenders, 1993 J Dairy Sci 76:1028-1034.

Chin, W. W. and Boime, I. 1990. In Glycoprotein Hormones. Serona Symp. Norwell, MA. pp. 19-20.

Choi, Y.H. "Developmental Cappacity of Equine Oocytes Matured and Cultured in Equine Trophoblast-Conditioned Media" Theriogenoogy 56: 320-339, 2001.

Chung, Y. G., et al. "Artificial insemination of Superovulated Heifers With 600,000 Sexed Sperm". J Anim. Sci. Suppl. 1. 836:215. 1998 abstr.

Clement, F., et al., "Which Insemination Fertilizes When Several Successive Inseminations are Performed Before Ovulation" 7th Int. Symp. Eq. Repro. 151. 1998 abstr.

Cran, D. G., et al, "Production of Lambs by Low Dose Intrauterine Insemination With Flow Cytometrically Sorted and Unsorted Semen", Therio. p. 267. 1997.

Cran, D. G., et al., "Sex Preselected in Cattle: A Field Trial", Veterinary Record 136, 1995, p. 495-496.

Cran, D. G., et al., "Production of Bovine Calves Following Separation of X- and Y-Chromosome Bearing Sperm and In Vitro Fertilization". Vet. Rec. 132:40-41. 1993.

Cran, D. G., et al., "The Predetermination of Embryonic Sex Using Flow Cytometrically Separated X and Y Spermatozoa" Human Reproduction Update 1996, vol. 2 (4) p. 355-63.

Crowley, J. P. "The facts of Once-Bred Heifer Production" School of Agric., Univ. of Aberdeen, Scotland. 1973.

Cui, K. et al, "X Larger than Y", Nature 366, p. 177-118, 1993.

Cui, K., "Size Differences Between Human X and Y Spermatozoa and Prefertilization Diagnosis", Molecular Human Reproduction, vol. 3, No. 1, pp. 61-67. 1997.

Curran, S. "Fetal Gender Determination" in *Equine Diagnostic Ultrasonography* 1st ed. Rantanen, N.W. and McKinnon A.O. (eds.) Williams and Williams, 1998, p. 165-69.

da Silva, Coutinho M.A.. "Effect of time of oocyte collection and site of insemination on oocyte transfer in mares." Animal Reproduction and Biotechnology Laboratiory, Colorado State Uniuversity, Fort Collins Journal of Animal Science 2002. 80:1275-1279.

*DakoCytomation, "MoFlo® Sorters"* http://www.dakocytomation.us/prod_productrelatedinformation?url=gprod_moflo_index.htm_onepage, printed Jun. 26, 2003.

Database up 1 BR9704313 (Alves, De Resende et al) Jun. 4, 1999.

Day, B. N., et al. Birth of Piglets Preselected for Gender Following In Vitro Fertilization of In Vitro Matured Pig Oocytes by X and Y Bearing Spermatozoa Sorted by High Speed Flow Cytometry. Therio. 49(1): 360. 1998 abstr.

de Leeuw, F.E. et al: "Effects of carious cryoprotective agents and membrane-stabilizing compounds on bull sperm emebrane integrity after cooling and freezing" Cryobiology US, Academic Press Inc 1993 pp. 32-44.

Dean, P.N., et al. "Hydrodynamic Orientation of Spermatozoa Heads for Flow Cytometry". Biophys. J. 23:7-13. 1978.

Demick, D.S., et al. "Effect of Cooling, Storage, Glycerization and Spermatozoal Numbers on Equine Fertility" J. Anim. Sci. 43:633-637. 1976.

DenDaas, J. H. G., et al. "The relationship between the number of spermatozoa inseminated and the reproductive efficiency of dairy bulls" J Dairy Sci. 81: 1714-1723. 1998.

Denham, A. "In-vitro studies on Sandhill Range Forage as Related to Cattle Preference", M.S. Thesis. Colorado State University. 1965.

Denk, Winfried. "Two-Photon Molecular Excitation in Laser-Scanning Microscopy," Handbook of Biological Confocal Microscopy. 1995.

Deutscher, G. H. "Extending Interval From Seventeen to Nineteen Days in the Melengestrol Acetate-Prostaglandin Estrous Synchronization Program for Heifers". The Professional Animal Scientist 16:164. 2000.

*Diagnostic Products Corporation, "Coat-A-Count"* http://www.Progesterone.com. 1998.

Dikeman, M. E. "Cattle Production Systems to Meet Future Consumer Demands" J. Anim. Sci. 59:1631, 1984.

Dinnyes, A., et al., "Timing of the First Cleavage Post-Insemination Affects Cryosurvival of In Vitro-produced Bovine Blastocysts", Molec. Reprod. Develop. 53, p. 318-324. 1999.

Dippert, K.D. "Fertilization Rates in Superovulated and Spontaneously Ovulating Mares" Theriogenology 41: 1411-1423, 1994.

Donaldson, L. E., "Effect of Insemination Regimen on Embryo Production in Superovulated Cows", The Veterinary Record, Jul. 13, p. 35-37, 1985.

Donoghue, A.M., et al. "Timing of Ovulation after Gonadotropin Induction and its Importance to Successful Intrauterine Insemination in the Tiger (*Panthera tigris*)" J. Reprod. Fertil. 107:53-58. 1996.

Douglas, R. H., "Review of Induction of Superovulation and Embryo Transfer in the Equine" Therio. 11:33-46. 1979.

Douglas, R. H., et al. "Induction of Ovulation and Multiple Ovulation on Seasonally-Anovulatory Mares with Equine Pituitary Fractions." Therio. 2(6): 133-142. 1974.

Doyle, S. P., et al. "Artificial Insemination of Lactating Angus Cows with Sexed Semen". Proc. Western Sect. Am. Soc. Anim. Sci. 50:203. 1999.

Duchamp, G., et al. "Alternative Solutions to hCG Induction of Ovulation in the Mare" J. Reprod. Fertil. Suppl. 35:221-228. 1987.

Evans, M. J. and Irvine, C. H. G. "Induction of Follicular Development, Maturation and Ovulation by Gonadotropin Releasing Hormone Administration to Acyclic Mares" Bio. Reprod. 16:452-462, 1977.

Ferrell, C. L. Effects of Post-Weaning Rate of Gain on Onset of Puberty and Productive Performance of Heifers of Different Breeds. J. Anim. Sci. 55:1272. 1982.

Ferrell, C. L. and T. G. Jenkins. "Energy-Utilization by Mature, Nonpregnant, Nonlactating Cows of Different Types" J. Anim.Sci. 58:234. 1984.

Field, R. A., et al., "Bone-Ossification and Carcass Characteristics of Wethers Given Silastic Implants Containing Estradiol", J. Anim. Sci. 68:3663-3668. 1990.

Field, R. et al., "Growth, Carcass, and Tenderness Characteristics of Virgin, Spayed, and Single-Calf Heifers", J. Anim. Sci. 74:2178. 1996.

Fitzgerald, B. P., et al. "Effect of Constant Administration of a Gonadotropin-Releasing Hormone Agonist on Reproductive Activity in Mares: Preliminary Evidence on Suppression of Ovulation During the Breeding Season." Am. J. Vet. Res. 54:1746-1751. 1993.

Fluharty, F. L., et al., "Effects of Age at Weaning and Diet on Growth of Calves",Ohio State University Dept. of Animal Scieneces. 1966 Ohio Agri. Res. And Den. Circular, 156:29 1966.

Foote, et al. Motility and Fertility of Bull Sperm Frozen-Thawed Differently in Egg Yolk and Milk Extenders Containing Detergent, 1987 J Dairy Sci 70:2642-2647.

Foote, R.H., "Buffers and Extenders: What Do They Do? Why Are They Important?" Proc of the NAAB Tech. Conf. On Artificial Insemination and Reproduction, 62-70 (1984).

Foulkes, J. A., et al. "Artificial Insemination of Cattle Using Varying Numbers of Spermatozoa." Vet. Rec. 101:205. 1977.

Francon, M. and Yamamoto, T., "Un Noveau et tres simple dispositif interferentiel applicable as microscope" Optica Acta 9, p. 395-408. 1962.

Fugger, E. F. "Clinical Experience with Flow Cytometric Separation of Human X- and Y- Chromosome Bearing Sperm", Therio. vol. 52, pp. 1435-1440.1999.

Fuller, Robert R. "Characterizing Submicron Vesicles With Wavelenth-Resolved Fluorescence in Flow Cytometry," University of Illinois, May 13, 1996.

Fulwyler, M. J. "Electronic Separation of Biological Cells by Volume." Science. 150:910. 1965.

Fulwyler, M. J. "Hydrodynamic Orientation of Cells." J of Histochem. and Cytochem. 25:781-783. 1977.

Garner, D. L., et al. "Quantification of the X and Y Chromosome-Bearing Spermatozoa of Domestic Animals by Flow Cytometry." Biol. Reprod. 28:312-321. 1983.

Ginther, O. J., "Sexual Behavior Following Introduction of a Stallion into a Group of Mares" Therio. vol. 19 (6) Jun. 1983.

Ginther, O. J., "Some Factors Which Alter Estrus Cycle in Mares." J. Anim. Sci. 33:1158. 1971 abstr.

Ginther, O. J., Reproductive Biology of the Mare. (2nd Ed.) Equiservices, Cross Plains, WI. 1992.

Gledhill, B. L. "Gender Preselection: Historical, Technical and Ethical Perspective." Semen Reprod. Endocrinol. 6:385-395. 1988.

Gombe, S. and Hansel, W. "Plasma Luteinizing Hormone (LH) and Progesterone Levels in Heifers on Restricted Energy Intakes." J. Anim. Sci. 37:728. 1973.

Gottlinger et al., "Operation of a Flow Cytometer", Flow Cytometry and Cell Sorting, A. Radbruch (Ed.), 1992, pp. 7-23.

Gourley, D. D. and Riese, R. L. "Laparoscopic Artificial Insemination in Sheep." Vet. Clin. N. Amer: Food Anim. Prac. 6(3): 615-633 (1990).

Graham, J. Analysis of Stallion semen and its Relation to Fertility. Abstract Complete article from Reproductive Technology vol. 12 # 1 Apr. 1996 now included in XYIDS000213.

Graham, J.K. and Hammerstedt, R.H.: "Differential Effects of Butylated Hydroxytoluene Analogs on Bull Sperm Subjected to Cold-Induced Membrane Stress," Cryobiology, 29:106-117 (1992).

Graham, James K., "Effect of Cholesterol-Loaded Cyclodextrins in Semen Extenders", Proceedings of the 19th Technical Conference on Artificial Insemination & Reproduction, 2003, pp. 91-95.

Gravert, H. O., "Genetic Aspects of Early Calving." In: J.C. Taylor (Ed.) *The Early Calving of Heifers and Its Impact on Beef Production.* 59 (1975).

Gregory, K. E., et al., "Characterization of Biological Types of Cattle—Cycle III: II Growth Rate and Puberty in Females" J. Anim. Sci. 49:461 (1979).

Grimes, I. F, and T. B. Turner. "Early Weaning of Fall Born Calves II. Post Weaning Performance of Early and Normal Weaned Calves". I. Prod. Agric. 4:168 (1991).

Grondahl, C., et al, "In Vitro Production of Equine Embryos", Biology of Reproduction, Monograph Series I, p. 299-307 (1995).

Guillou, F. and Combarnous, Y. "Purification of Equine Gonadotropins and Comparative Study of Their Acid-Dissociation and Receptor-Binding Specificity." Biochemica Et Biophysica Acta 755:229-236 (1983).

Gurnsey, M. P., and Johnson, L.A., "Recent Improvements in Efficiency of Flow Cytometric Sorting of X and Y-Chromosome Bering Sperm of Domestic Animals: a Review" New Zealand Society of Animal Protection, three pages (1998).

Hall, J. B., et al., "Effect of Age and Pattern of Gain on Induction of Puberty with a Progestin in Beef Heifers." J. Anim. Sci. 75:1606 (1997).

Hamano, K., et al., "Gender Preselection in Cattle with Intracytoplasmically Injected, Flow Cytometrically Sorted Sperm Heads", Biology of Reproduction 60, p. 1194-1197 (1999).

Hammerstedt, et al., "Cryopreservation of Mammalian Sperm: What We Ask Them to Survive," Journal of Andrology, 11:1:73-88 (1990).

Harrison, L.A., et al., "Comparison of HCG, Buserelin and Luprostiol for Induction of Ovulation in Cycling Mares." Eq. Vet. Sci. 3:163-166 (1991).

Harte, F. J. "System of Production of Beef From Once Calved Heifers." In: J.C. Taylor (Ed.) *The Early Calving of Heifers and its Impact on Beef Production.* 123 (1975).

Hawk, H. W., et al., "Fertilization Rates in Superovulating Cows After Deposition of Semen on the Infundibulum Near the Uterotubal Junction or After Insemination with High Numbers of Sperm", XP-002103478, Therio. vol. 29, No. 5, p. 1131-1142 (1988).

Hermesmeyer, G. N., et al. "Effects of Prenatal Androgenization and Implantation on the Performance and Carcass Composition of Lactating Heifers in the Single-Calf Heifer System." The Professional Animal Scientist 15:173. 1999.

Herweijer, Hans. "High-Speed Photodamage Cell Selection Uing Bromodeoxyuridine/Hoechst 33342 Photosensitized Cell Killing," Sep. 23, 1987.

Herzenberg, Leonard A. "Flourescence-activated Cell Sorting," Sci. Am. 1976; 234, pp. 108-117.

Hilton, G. G., et al., "An Evaluation of Current and Alternative Systems for Quality Grading Carcasses of Mature Slaughter Cows." J. Anim. Sci. 76:2094. 1998.

Ho, L., et al., "Influence of Gender, Breed and Age on Maturity Characteristics of Sheep." J. Anim. Sci. 67:2460-2470. 1989.

Hofferer, S., et al. "Induction of Ovulation and Superovulation in Mares Using Equine LH and FSH Separated by Hydrophobic Interaction Chromatography." J. Reprod. Fertil. 98:597-602. 1993.

Hohenboken, W. D. "Applications of sexed semen in cattle production." Therio. 52:1421. 1999.

Holtan, D. W., et al., "Estrus, Ovulation and Conception Following Synchronization With Progesterone, Prostaglandin F2a and Human Chorionic Gonadotropin in Pony Mares." J. Anim. Sci. 44:431-437. 1977.

Horan, Paul K. "Quantitative Single Cell Ana,lysis and Sorting, Rapid Analysis and sorting of cells is emerging as an important new technology in research and medicine." Science, Oct. 1977.

Householder, D. D., et al. "Effect of Extender, Number of Spermatozoa and hCG on Equine Fertility." J. Equine Vet. Sci. 1:9-13. 1981.

Howard, J. G., et al., "Comparative Semen Cryopreservation in Ferrets (*Mustela putorious* furo) and Pregnancies After Laparoscopic Intrauterine Insemination With Frozen-Thawed Spermatozoa." J. Reprod. Fertil. 92:109-118. 1991.

Howard, J. G., et al., "Sensitivity to Exogenous Gonadotropins for Ovulation and Laparoscopic Artificial Insemination in the Cheetah and Clouded Leopard." Biol. Reprod. 56:1059-1068. 1997.

Hunter, R. H. F. "Transport and Storage of Spermatozoa in the Female Tract." Proc 4th Int. Congress Anim. Repro. and A. I. 9:227-233. 1980.

Hyland, J. H., et al., "Gonadotropin Releasing Hormone (GnRH) Delivered by Continuous Infusion Induces Fertile Estrus in Mares During Seasonal Acyclity" Proceedings of the Annual Convention of the American Association of Equine Practitioners (34th) 1989, p. 181-190.

IMV Technologies, Protocol of Bioxcell with Fresh Semen, 1 page, 2000.

IMV Technologies, Protocol of Bioxcell with Frozen Semen, 2 pages, 2000.

Irvine, C H. G. and Alexander, S. L. "GnRH" Chapter 4 in Equine Reproduction, McKinnon and Voss eds. Lea and Febiger. Philadelphia, London. p. 37. (1993).

Iwazumi, Y., et al., "Superovulation Using CIDR in Holstein Cows" J. of Reprod. Dev. vol. 40 (3) 1994, pp. 259-266.

Jafar, et al., "Sex Selection in Mammals: A Review", Therio. vol. 46, p. 191-200. (1996).

Jakubiczka, S. et al. "A Bovine Homologue of the Human TSPY Gene." Genomics. 1993, vol. 17, No. 3, pp. 732-735.

Jarriage, R. "Age of Cows at First Calving in France." In: J.C. Taylor (Ed.) *The Early Calving of Heifers and its Impact on Beef Production.* 10. (1975).

Jasko, D. J., et al., "Effect of Insemination Volume and Concentration of Spermatozoa on Embryo Recovery in Mares", Therio. 37:1233-1239, (1992).

Jasko, D. J., et al., "Pregnancy Rates Utilizing Fresh, Cooled and Frozen-Thawed Stallion Semen", American Association of Equine Practitioners 38th Annual Convention Proceedings, 1992, p. 649-60.

Johnson, A. L. "Pulsatile Administration of Gonadotropin Releasing Hormone Advances Ovulation in Cycling Mares", Biol. Reprod. 35:1123—1130, (1986).

Johnson, A. L., et al. "Use of Gonadotropin-Releasing Hormone (GnRH) Treatment to Induce Multiple Ovulations in the Anestrous Mare" Eq. Vet. Sci. 8:130-134, (1988).

Johnson, L.A., "Flow Cytometric Determination of Spermatozoa Sex Ratio in Semen Purportedly Enriched for X or Y Bearing Spermatozoa", Therio. 1988 29:265 abstr.

Johnson, L.A., "Gender Preselection in Domestic Animals Using Flow Cytometrically Sorted Sperm" J. Anim. Sci. (Suppl I) 70:8-18. (1992).

Johnson, L.A., "The Safety of Sperm Selection by Flow Cytometry" Ham. Reprod. 9(5): 758. (1994).

Johnson, L.A., "Gender Preselection in Humans? Flow Cytometric Separation of X and Y Spermatozoa for the Prevention of X-Linked Diseases" Human Reproduction vol. 8 No. 10, p. 1733-1739 (1993).

Johnson, L.A., "Gender Preselection in Mammals: An Overview", Deutsch. Tierarztl. Wschr, vol. 103, p. 288-291 (1996).

Johnson, L.A., "Isolation of X- and Y-Bearing Spermatozoa for Sex Preselection." Oxford Reviews of Reproductive Biology. Ed. H. H. Charlton. Oxford University Press. 303-326. (1994).

Johnson, L.A., "Sex Preselection in Rabbits: Live Births from X and Y Sperm Separated by DNA and Cell Sorting", Biology of Reproduction 41, pp. 199-203 (1989).

Johnson, L.A., "Sex Preselection in Swine: Flow Cytometric Sorting of X- and Y- Chromosome Bearing Sperm to Produce Offspring", Boar Semen Preservation IV, p. 107-114. (2000).

Johnson, L.A., "Successful Gender Preselection in Farm Animals", Agricultural Biotechnology, p. 439-452. (1998).

Johnson, L.A., et al., "Flow Sorting of X and Y Chromosome-Bearing Spermatozoa into Two Populations", Gamete Res. 16:203-212. (1987).

Johnson, L.A., et al., "Improved Flow Sorting Resolution of X- and Y-Chromosome Bearing Viable Sperm Separation Using Dual Staining and Dead Cell Gating" Cytometry 17 (suppl 7): 83, (1994).

Joseph, R. L. "Carcass composition and meat quality in once calved heifers." In: J.C. Taylor (Ed.) *The Early Calving of Heifers and its Impact on Beef Production*. 143. (1975).

Joseph, R. L. and J. P. Crowley. "Meat Quality of Once-Calved Heifers." Irish J. of Agric. Research 10:281. (1971).

Kachel, V., et al., "Uniform Lateral Orientation, Caused by Flow Forces, of Flat Particles in Flow-Through Systems", The Journal of Histochemistry and Cytochemistry, vol. 25, No. 7, pp. 774-780. (1997).

Kanayama, K., et al., "Pregnancy by Means of Tubal Insemination and Subsequent Spontaneous Pregnancy in Rabbits." J. Int. Med. Res. 20:401-405. (1992).

Karabinus, et al., "Effects of Egg Yolk-Citrate and Milk Entenders on Chromatin Structured Viability of Cryopreserved Bull Sperm", Journal of Dairy Science, vol. 74, No. 11, p. 3836-3848. (1999).

Keeling, P. "A Modeling Study of Once-Bred Heifer Beef Production." Proceedings of the New Zealand Society of Animal Production. 51. (1991).

Kilicarslan, M. R., et al., "Effect of GnRH and hCG on Ovulation and Pregnancy in Mares." Vet. Rec. 139:119-120. (1996).

Kinder, J. E., et al. "Endocrine Basis for Puberty in Heifers and Ewes." J. Repro. and Fertility, p. 393. (1995).

Kinder, J. E., et al., "Endocrine Regulation of Puberty in Cows and Ewes." J. Repro. and Fertility, Supl. 34:167. (1987).

Kinoshita, Shuichi. "Spectroscopic Properties of Fluorescein in Living Lymphocytes," Osaka Uinversity Aug. 7, 1986.

Klindt, J. and J. D. Crouse. "Effect of Ovariectomy and Ovariectomy with Ovarian Autotransplantation on Feedlot Performance and Carcass Characteristics of Heifers." J. Anim. Sci. 68:3481. (1990).

Klosterman, E. W. and C. F. Parker. "Effect of Size, Breed and Sex Upon Feed Efficiency in Beef Cattle." North Central Regional Research Publication 235, Ohio Agric. Research and Development Center 1090:3. (1976).

Kniffen, D. M., et al., "Effects of Long-Term Estrogen Implants in Beef Heifers." J. Anim. Sci. 77:2886.(1999).

Kobata, Akira, "Structures and Functions of the Sugar Chains of Human Chorionic Gonadotropin", in *Glycoprotein Hormones* Chin, W.W. and Boime, I., eds. Serono Symposia, Norwell, MA. p. 19-20. 1990.

Koch, R. M., et al., "Characterization of Biological Types of Cattle -Cycle-II .3." Carcass Composition, Quality and Palatability. J. Anim. Sci. 49:448. (1919).

Kommisrud E., et al. "Comparison of Two Processing Systems for Bull Semen with Regard to Post-Thaw Motility and Nonreturn Rates." Theriogenology, vol. 45, 1996, pp. 1515-1521.

Lapin, D. R. and Ginther, O. J. "Induction of Ovulation and Multiple Ovulations in Seasonally Anovulatory and Ovulatory Mares with an Equine Pituitary Extract." J. Anim. Sci. 44:834-842. (1977).

Laster, D. B., "Factors Affecting Dystocia and Effects of Dystocia on Subsequent Reproduction in Beef-Cattle." J. Anim. Sci. 36:695. (1973).

Lawrenz, R. "Preliminary Results of Non-Surgical Intrauterine Insemination of Sheep With Thawed Frozen Semen." J S Afr. Vet. Assoc. 56(2): 61-63. (1985).

Levinson, G., et al., "DNA-based X-Enriched Sperm Separation as an Adjunct to Preimplantation Genetic Testing for the Preparation of X-linked Disease." Mol. Human Reprod. 10:979-982. (1995).

Lindsey, A. C., et al., "Low Dose Insemination of Mares Using Non-Sorted and Sex-Sorted Sperm" Animal Reproduction Science 68 p. 279-89 (2001).

Liu, Z, et al. "Survival of Bull Sperm Frozen at Different rates in Media Varying in Osmolarity." Cryobiology, vol. 27, 1998, pp. 219-230.

Lonergan, P., et al., "Effect of Time Interval from Insemination to First Cleavage on the Development of Bovine Embryos In Vitro and In Vivo", Therio. p. 326 (1999).

Long, C.R., et al., "In Vitro Production of Porcine Embryos From Semen Sorted for Sex With a High Speed Cell Sorter: Comparison of Two Fertilization Media." Therio. 49(1): 363 (1998) abstr.

Loy, R. G. and Hughes, J.P. "The Effects of Human Chorionic Gonadotropin on Ovulation, Length of Estrus, and Fertility in the Mare." Cornell Vet. 56:41-50 (1965).

Lu, K. H. et al., "In Vitro Fertilization of Bovine Oocytes with Flow-Cytometrically Sorted and Unsorted Sperm from Different Bulls" Therio. 2001 abstr.

Lu, K. H., et al., "In Vitro Fertilization with Flow-Cytometrically-Sorted Bovine Sperm", Therio 52, p. 1393-1405. (1999).

Lynch, I. M., et al., "Influence of timing of gain on growth and reproductive performance of beef replacement heifers." J. Anim. Sci. 75:1715. (1997).

Macmillan, K. L. and Day, A.M., "Prostaglandin F2a: A Fertility Drug In Dairy Cattle?", Animal Research Station, Private Bag, Hamilton, New Zealand, Therio. vol. 18, No. 3, p. 245-253 (1982).

Manni, Jeff. "To-Photon Excitation Expands the Capabilities of Laser-Scanning Microscopy," 1996 Biophotonics International.

Manning, S.T., et al., "Development of Hysteroscopic Insemination of the Uterine Tube in the Mare", Proceedings of the Annual Meeting of the Society for Theriogenology, 1998, p. 84-85.

Martin, A. H., et al., "Characteristics of Youthful Beef Carcasses in Relation to Weight, Age and Sex. III. Meat Quality Attributes." Canadian J. Anim. Sci. 51:305. (1971).

Martin, L. C., et al., "Genetic-effects on Beef Heifer Puberty and Subsequent Reproduction." J. Anim. Sci. 70:4006. (1992).

Martinez, E. A., et al., "Successful Low-Dose Insemination by a Fiberoptic Endoscope Technique in the Sow", Proceedings Annual Conference of the International Embryo Transfer Society, Netherlands, Therio. vol. 53 p. 201, Jan. 2000.

Matsuda, Y. and Tobari, I. "Chromosomal Analysis in Mouse Eggs Fertilized In Vitro With Sperm Exposed to Ultraviolet Light (UV) and Methyl and Ethyl Methanesulfonate (MMS and EMS)." Mutat. Res. 198:131-144. (1988).

Matulis, R. J., "Growth and carcass characteristics of cull cows after different times-on-feed." J. Anim. Sci. 65:669. (1987).

Mauleon, P. "Recent research related to the physiology of puberty." In: J.C. Taylor (ed.) *The Early Calving of Heifers and its Impact on Beef Production*. (1975).

Maxwell, W. M. C., et al., Fertility of Superovulated Ewes After Intrauterine or Oviductal Insemination with Low Numbers of Fresh or Frozen-Thawed Spermatozoa. Reprod. Fertil. Dev. 5:57-63. (1993).

Maxwell, W. M. C., et al., "The Relationship Between Membrane Status and Fertility of Boar Spermatozoa After Flow Cytometric Sorting in the Presence or Absence of Seminal Plasma" Reprod. Fertil. Dev. vol. 10 p. 433-40 (1998).

Maxwell, W. M. C., et al., "Viability and Membrane Integrity of Spermazota after Dilution and Flow Cytometric Sorting in the Presence or Absence of Seminal Plasma." Reprod. Fertil. Dev. 8:1165-78. (1997).

McCormick, R. J. "The Flexibility of the Collagen Compartment of Muscle." Meat Sci. 36:79. (1994).

McCue, P.M. "Superovulation" Vet. Clin. N. Amer. Eq. Prac. 12:1-11. (1996).

McCue, P.M., et al., "Oviductal insemination in the mare." 7th Internat. Symp. Eq. Reprod. 133 (1997) abstr.

McDonald, L. E. "Hormones of the Pituitary Gland." Veterinary Pharmacology and Therapeutics. 6th ed. Edited by N. H. Booth and L. E. McDonald. Ames, Iowa State Univ. Press. p. 590 (1988).

McKenna, T. et al., "Nonreturn Rates of Dairy Cattle Following Uterine Body or Cornual Insemination." J. Dairy Sci. 73:1179-1783 (1990).

McKinnon, A.O. and Voss, J. L. *Equine Reproduction*. Lea and Febiger. Philadelphia, London (1993).

McKinnon, A.O., et al., "Predictable Ovulation in Mares Treated With an Implant of the GnRH Analogue Deslorelin." Eq. Vet. J. 25:321-323. (1993).

McKinnon, A.O., et al., "Repeated Use of a GnRH Analogue Deslorelin (Ovuplant) for Hastening Ovulation in the Transitional Mare." Eq. Vet. J. 29:153-155. (1996).

McLeod, John H., "The Axicon: A New type of Optical Element", Journal of the Optical Society of America, vol. 44 No. 8, Aug. 1954, Eastman Kodak Company, Hawk-Eye Works, Rochester, New York.

McNutt, T. L. et al., "Flow Cytometric Sorting of Sperm: Influence on Fertilization and Embryo/Fetal Development in the Rabbit", Molecular Reproduction and Development, vol. 43, p. 261-267 (1996).

Meilgaard, M., et al., "Sensor Evaluation Techniques." CRC Press Inc., Boca Raton, FL. (1991).

Meinert, C., et al., "Advancing the Time of Ovulation in the Mare With a Short-Term Implant Releasing the GnRH Analogue Deslorelin", Equine Veterinary Journal, 25, p. 65-68 (1993).

Melamed et al, "An Historical Review of the Development of Flow Cytometers and Sorters", 1979, pp. 3-9.

Mendes Jr., J.O.B. "Effect of heparin on cleavage rates and embryo production with four bovine sperm preparation protocols" Theriogenology 60 (2003) 331-340.

Menke,E. A Volume Activated Cell Sorter Journal of Histo chemistry and Cyto Chemistry, 1977, vol. 25,No. 7, pp. 796-803.

Merton, J., et al., "Effect of Flow Cytometrically Sorted Frozen/Thawed Semen on Success Rate of In Vitro Bovine Embryo Productiion", Therio. 47, p. 295. (1997).

Metezeau P. et al. Improvement of Flow Cytometry Analysis and Sorting of Bull Spermatozoa by Optical Monitoring of Cell Orientation as Evaluated by DNA Specific Probing Molecular Reproduction and Development, 1991, vol. 30 pp. 250-257.

Meyers, P. J., et al., "Use of the GnRH Analogue, Deslorelin Acetate, in a Slow Release Implant to Accelerate Ovulation in Oestrous Mares." Vet. Rec. 140:249-252. (1997).

Michel, T. H., et al., "Efficacy of Human Chorionic Gonadotropin and Gonadotropin Releasing Hormone for Hastening Ovulation in Thoroughbred Mares." Eq. Vet. J. 6:438-442. (1986).

Miller, S. J. "Artificial Breeding Techniques in Sheep." Morrow, D.A. (ed): Current Therapy in Therio 2. Philadelphia, WB Saunders. (1986).

Mirskaja, L. M. and Petropavloskii, V.V. "The Reduction of Normal Duration of Heat in the Mare by the Administration of Prolan." Probl. Zivotn. Anim. Breed. Abstr. 5:387. (1937).

Moe, P. W., "Energetics of Body Tissue Mobilization." J. of Dairy Sci. 1971 54:548.

Molinia, F. C., et al., "Successful Fertilization After Superovulation and Laparoscopic Intrauterine Insemination of the Brushtail Possum *Trichosurus vulpecula*, and Tammar Wallaby, *Macropus eugenii*." J. Reprod. Fertil. 112:9-17. (1998).

Moran, C., et al., "Puberty in Heifers -a Review." Animal Reproduction Sci. 18:167. (1989).

Moran, D. M. et al., "Determination of Temperature and Cooling Rate Which Induce Cold Shock in Stallion Spermatozoa", Therio. vol. 38 p. 999-1012 (1992).

Morcom, C. B. and Dukelow, W.R. "A Research Technique for the Oviductal Insemination of Pigs Using Laparoscopy." Lab. Anim. Sci. p. 1030-1031. (1980).

Morgan, J. B., et al., "National Beef Tenderness Survey." J. Anim. Sci. 69: 3274. (1991).

Morris, L. H., et al., "Hysteroscopic Insemination of Small Numbers of Spermatozoa at the Uterotubal Junction of Preovulatory Mares", Journal of Reproduction and Fertility, vol. 118, pp. 95-100 (2000).

Morris, S. T., et al., "Biological efficiency: How relevant is this concept to beef cows in a mixed livestock seasonal pasture supply context?" Proceedings of the New Zealand Society of Animal Production 54:333. (1994).

Moseley, W. M., et al., "Relationship of Growth and Puberty in Beef Heifers Fed Monensin" J. Anim. Sci. vol. 55 No. 2 p. 357-62 (1982).

Mount, D. E. "Fibrous and Non-fibrous Carbohydrate Supplementation to Ruminants Grazing Forage From Small Grain Crops." M.S. Thesis. Abstr. Colorado State University. (2000).

Muller, W. and Gautier, F. "Interactions of Heteroaromatic Compounds with Nucleic Acids." Euro. J Biochem. 54:358. (1975).

Mullis, K. B. and F. A. Faloona, "Specific Synthesis of DNA in Vitro Via a Polymerase-Catalyzed Chain Reaction" Methods in Enzymology vol. 155 p. 335-350 (1978).

Munne, S. "Flow Cytometry Separation of X and Y Spermatozoa Could be Detrimental to Human Embryos", Hum. Reprod. 9(5): 758 (1994).

Myers, S. E., "Performance and Carcass Traits of Early-Weaned Steers Receiving Either a Pasture Growing Period or a Finishing Diet at Weaning." J. Anim. Sci. 77:311. (1999).

Myers, S. E., et al., "Comparison of Three Weaning Ages on Cow-Calf Performance and Steer Carcass Traits." J. Anim.Sci. 77:323. (1999).

Myers, S. E., et al., "Production Systems Comparing Early Weaning to Normal Weaning With or Without Creep Feeding for Beef Steers." J. Anim. Sci. 77:300. (1999).

Nix, J. P., et al., "Serum Testosterone Concentration, Efficiency of Estrus Detection and Libido Expression in Androgenized Beef Cows." Therio. 49: 1195. (1998).

Nowshari, et al., "Superovulation of Goats with Purified pFSH Supplemented with Defined Amounts of pLH", Therio. vol. 43, p. 797-802 (1995).

NRC. "Nutrient Requirements for Beef Cattle." National Academy of Sci. National Research Council, Washington, DC. (1996).

O'Brien, Justine K. et al., "Preliminary Developments of Sperm Sorting Technology in Non-human Primates", Biology of Reproduction 2001 (Suppl. 1) 64:158.

Olive, M.D., "Detection of Enterotoxigenic *Escherichia coli* after Polymerase Chain Reaction Amplification with a Tehrmostable DNA Polymerase", J of Clinical Microbiology, Feb. 1989 p. 261-265.

Olson, S.E. and Seidel, G. E. Jr., "Reduced Oxygen Tension and EDTA improve Bovine Zygote Development in a Chemically Defined Medium", J. of Anim. Sci. 78, pp. 152-157. (2000).

Owen, J. B. "The Maiden Female-A Means of Increasing Meat Production." Proc. Symp. On the Use of Once Bred Heifers and Gilts. (1973).

Ozhin F.V. et al. Artificial insemination of farm animals. Moscow, Izdatelstvo Selskokhozyaastvennoi Literatury, 1961, pp. 350-361 and pp. 380-393.

Pace, M. M. and Sullivan, J. J. "Effect of Timing of Insemination, Numbers of Spermatozoa and Extender Components on Pregnancy Rates in Mares Inseminated with Frozen Stallion Semen." J. Reprod. Fertil. Suppl. 2001, 23:115-121.

Parrish, J. J., et al., "Capacitation of Bovine Sperm by Heparin", Department of Meat and Animal Science, Biology Of Reproduction 38, p. 1171-1180 (1988).

Patterson, D. J., et al., "Estrus Synchronization with an Oral Progestogen Prior to Superovulation of Postpartum Beef Cows" Therio. 48, 1025-33 (1997).

Peippo, J., et al., "Sex Diagnosis of Equine Preimplantation Embryos Using the Polymerase Chain Reaction", Therio. vol. 44:619-627 (1995).

Penfold, L.M.et at., "Comparative Motility of X and Y Chromosome-Bearing Bovine Sperm Separated on the Basis of DNA Content", Mol. Reprod. And Develop. 1998, vol. 50,pp. 323-327.

Perry, E. J., "Historical Background" The Artificial Insemination of Farm Animals. 4th ed. E. J. Perry (ed.) New Brunswick, Rutgers University Press, pp. 3-12. (1968).

Petersen, G. A., et al, "Cow and Calf Performance and Economic-Considerations of Early Weaning of Fall-Born Beef Claves", J. Anim. Sci., 64:15, pp. 15-22. (1987).

Petit, M. "Early Calving in Suckling Herds." In: J.C. Taylor (ed.) *The Early Calving of Heifers and its Impact on Beef Production*. p. 157-176. (1975).

Pickett B.W., et al., Recent Developments in Artificial Inseminatin in Horses Livestock Production Science, 1998.

Pickett, B. W, et al., "Factors Influencing the Fertility of Stallion Spermatozoa in an A. I. Program." Proc. 8th International Congress Anim. Reprod. A. I. Krakow, Poland. 4:1049—1052. (1976).

Pickett, B. W., et al., "Effect of Seminal Extenders on Equine Fertility." J. Anim. Sci. 40:1136-1143. (1975).

Pickett, B. W., et al., "Influence of Seminal Additives and Packaging Systems on Fertility of Bovine Spermatozoa." J. Anim. Sci. Suppl. II. 47:12. (1978).

Pickett, B. W., et al., "Management of the Mare for Maximum Reproductive Efficiency." CSU Anim. Repro. Lab. Bull. No. 06. Fort Collins CO. (1989).

Pickett, B. W., et al., "Procedures for Preparation, Collection, Evaluation and Insemination of Stallion Semen." CSU Exp. Sta. Artira. Reprod. Lab. Gen. Series Bull. 935. (1973).

Pickett, B. W., et al., "Recent Developments in Artificial Insemination in Horses", Livestock Production Science, 40, p. 31-36 (1994).

Pickett, B. W., et al., "The Effect of Extenders, Spermatozoal Numbers and Rectal Palpation on Equine Fertility." Proc. Fifth N.A.A.B Tech. Conf. A. I. Reprod. Columbia, MO. pp. 22-22. (1974).

Pinkel et al., "Flow Chambers and Sample Handling", Flow Cytometry: Instrumentation and Data Analysis, Van Dilla et al. (Eds.), 1985, pp. 77-128.

Pinkel, D., et al, "Flow Cytometric Determination of the Proportions of X- and Y- Chromosome-Bearing Sperm in Samples of Purportedly Separated Bull Sperm", J. of Anim. Sci., vol. 60, p. 1303-1307 (1998).

Pinkel, D., et al., "High Resolution DNA Content Measurements of Mammalian Sperm", Cytometry 3:1-9. (1982).

Pinkel, D., et al., "Sex Preselection in Mammals? Separation of Sperm Bearing the Y and "O" Chromosomes in the Vole Microtus Oregoni", Science vol. 218 p. 904 (1982).

Piston, D.W. "Three-dimensionally resolved NAD(P)H cellular metabolic redox imaging of the in situ cornea with two-photon excitation laser scanning microscopy," Journal of Microscopy, vol. 178, Nov. 29, 1994.

Polge, E. J., "Historical Perspective of AI: Commercial Methods of Producing Sex Specific Semen, IVF Procedures", Proceedings of the 16th Technical Conference on Artificial Insemination & Reproduction, Cambridge, England, pp. 7-11. (1996).

Polge, et al, "Revival of Spermatozoa After Vitrification and Dehydration at Low Temperatures," Nature, 164:666 (1994).

Preza, C. et al, "Determination of Direction-Independent Optical Path-Length Distribution of Cells Using Rotational-Diversity Transmitted-Light Differential Interference Contrast (DIC) Images", Presented at the Multidimensional Microscopy: Image Acquisition and Processing V, p. 1-11 (1998).

Prokofiev M.I. Regoulyatsia Razmnozhenia Selskokhozyastvennykh Zhivotnykh, Leningrad, NAOUKA Publishing House, 1983, pp. 181-195.

Province, C.A., et al., Cooling Rates, Storage, Temperatures and Fertility of Extended Equine Spermatozoa Therio. vol. 23 (6) p. 925-934, Jun. 1985.

Pursel, et al, "Effect of Orvus ES Paste on Acrosome Morphology, Motility and Fertilizing Capacity of Frozen-Thawed Boar Sperm," Journal of Animal Science, 47:1:198-202 (1978).

Purvis, H. T. and J. C. Whittier. "Effects of Ionophore Feeding and Anthelmintic Administration on Age and Weight at Puberty in Spring-Born Beef Heifers." J. Anim. Sci. 74:736-744. (1996).

Randel, R. D. "Nutrition and Postpartum Rebreeding in Cattle." J. Anim. Sci. 68:853. (1990).

Rath, D., et al., "Low Dose Insemination Technique in the Pig", Boar Semen Preservation IV, p. 115-118. (2000).

Rathi, R. et al., "Evaluation of In Vitro Capacitation of Stallion Spermatoza", Biology of Reproduction 2001, vol. 65, pp. 462-470.

Recktenwald, Diether. "Cell Separation Methods and Applications," New York 1997.

Reiling, B.A., et al., "Effect of Prenatal Androgenization on Performance, Location, and Carcass and Sensory Traits on Heifers in Single Calf Heifer System", J. Anim. Sci., 1995, 73: 986, p. 986-992.

Reiling, B.A., et al., "Effects of Prenatal Androgenization and Lactation on Adipose Tissue Metabolism in Finishing Single-Calf Heifers" J. Anim. Sci. vol. 75 p. 1504-1512 (1997).

Reiling, B.A., et al., "Effects of prenatal Androgenization, Melengestrol Acetate, and Synovex-H on Feedlot Performance, Carcass, and Sensory Traits of Once-Calved Heifers" J. Anim. Sci. vol. 74 p. 2043-51 (1996).

Rens, W., et al., "A Novel Nozzle for More Efficient Sperm Orientation to Improve Sorting Efficiency of X and Y Chromosome-Bearing Sperm", Technical Notes, Cytometry 33, p. 476-481 (1998).

Rens, W., et al., "Improved Flow Cytometric Sorting of X- and Y-Chromosome Bearing Sperm: Substantial Increase in Yield of Sexed Semen", Molecular Reproduction and Development, p. 50-56(1999).

Rieger, D., et al, "The Relationship Between the Time of First Cleavage of Fertilized Cattle Oocytes and Their Development to the Blastocyst Stage", Therio. 1999, p. 190.

Rigby, S. L., et al., "Pregnancy Rates in Mares Following Hysterscopic or Rectally-Guided Utero-Tubal insemination with Low Sperm Numbers" Abstracts/Animal Reproduction Science vol. 68 p. 331-333 (2001).

Riggs, B.A. "Integration of Early Weaning and Use of Sexed Semen in a Single-Calf Heifer System to Increase Value of Non-Replacement Heifers" MS Thesis, Colorado State University, Spring 2000.

Ritar, A. and Ball, A., "Fertility of Young Cashmere Goats After Laparoscopic Insemination." J. Agr. Sci. 117: p. 271-273. (1991).

Roberts, J. R., Veterinary Obstetrics and Genital Diseases. Ithaca, New York. p. 740-749. (1971).

Romero-Arredondo, A. "Effects of Bovine Folicular Fluid on Maturation of Bovine Oocytes" Theriogenology 41: 383-394, 1994.

Romero-Arrendondo, A. "Effects of Follicular Fluid dring In Virto Maturation of Bovine Oocytes on In Vitro Fertilization and Early Embryonic Development" Biology of Reproduction 55, 1012-1016 1996.

Romita, A. "Some Considerations on the Beef Situation in Italy." In: J.C. Taylor (ed.) The Early Calving of Heifers and its Impact on Beef Production. 23. (1975).

Roser, J. F., et al., "Reproductive Efficiency in Mares With Anti-hCG Antibodies." Proc 9th Int. Congr. Anim. Repro. and A. I. 4:627 (1980) abstr.

Roth, T. L., et al., "Effects of Equine Chorionic Gonadotropin, Human Chorionic Gonadotropin, and Laparoscopic Artificial Insemination on Embryo, Endocrine, and Luteal Characteristics in the Domestic Cat." Bio. Reprod. 57:165-171 (1997).

Roux, M., et al., "Early Calving Heifers Versus Maiden Heifers for Beef-Production from Dairy herds. I. The Effects of Genotype (Friesian and Carloads x Friesian) and Two Feeding Levels in the Rearing Period on Growth and Carcass Quality." Livestock Prod. Sci. 16:1 (1987).

Rowley, H. S., et al., "Effect of Insemination Volume on Embryo Recovery in Mares." J. Equine Vet. Sci. 10:298-300 (1990).

Roy, J. H., "Rearing Dairy-Herd Replacements." Journal of the Society Of Dairy Technology 31:73-79 (1978).

Rutter, L. M., et al., "Effect of Abomasal Infusion of Propionate on the GnRH-Induced Luteinizing Hormone Release in Prepuberal Heifers." J. Anim. Sci. 56:1167 (1983).

Salamon, S., Artificial Insemination of Sheep, Chippendale, New South Whales. Publicity Press. p. 83-84 (1976).

Schenk, J. L. "Applying Sperm Sexing Technology to the AI Industry", Proceedings of the 18th Technical Conference on Artificial insemination & Reproduction, Sep. 29-30, 2000.

Schenk, J. L, et al., "Imminent Commercialization of Sexed Bovine Sperm", Proceedings, The Range Beef Cow Symposium XVI p. 89-96 (1999) Greeley Colorado.

Schiewe, M. C., et al., "Transferable Embryo Recovery Rates Following Different Insemination Schedules in Superovulated Beef Cattle" Therio. 28 (4) Oct. 1997, pp. 395-406.

Schillo, K. K., et al, "Effects of Nutrition and Season on the Onset of Puberty in the Beef Heifer." J. Anim. Sci. 70:3994 (1992).

Schmid, R. L., et al, "Fertilization with Sexed Equine Spermatozoa Using Intracytoplasmic Sperm Injection and Oviductal Insemination", 7th International Symposium On Equine Reproduction, pp. 139 (1998) abstr.

Schnell, T. D., et al, "Performance, Carcass, and Palatability Traits for Cull Cows Fed High-Energy Concentrate Diets for 0, 14, 28, 42, or 56 days." J. Anim. Sci. 75:1195. (1997).

Schoonmaker, J. P., et al., "Effects of Age at Weaning and Implant Strategy on Growth of Steer Calves." J. Anim. Sci. (Suppl. II) 76:71. (1998) abstr.

Seidel, G. E. Jr. "Cryopreservation of Equine Embryos" Veterinary Cliniics of North America: Equine Practice vol. 12, No. 1, Apr. 1996.

Seidel, G. E. Jr. "Sexing Bovine Sperm" The AABP Proceedings—vol. 34, Sep. 2001.

Seidel, G. E. Jr. Sexing mammalian spermatozoa and embryos-state of the art Journal of Reproduction and Fertility Supp 54, 477-487 1999.

Seidel, G. E. Jr. "Uterine Horn Insemination of Heifers With Very Low Numbers of Nonfrozen and Sexed Spermatozoa", Atlantic Breeders Cooperative, Therio. 48: pp. 1255-1264, (1997).

Seidel, G. E. Jr et al., "Current Status of Sexing Mammalian Spermatozoa," Society for Reproduction and fertiity, pp. 733-743, 2002.

Seidel, G. E. Jr., "Commercilizing Repreductive Biotechnology—The Approach used by XY, Inc., " Theriogenology, p. 5, 1999.

Seidel, G. E. Jr., "Use of Sexed Bovine Sperm for In Vitro Fertilization and Superovulation", Animal Reproduction and Biotech Lab, CSU, Proceedings of the 2000 CETA/ACTE Convention, Charlottetown, Prince Edward Island, Aug. 2000, pp. 22-24.

Seidel, G. E. Jr., "Artificial Insemination With X-and Y-Bearing Bovine Sperm", Animal Reproduction and Biotechnology Laboratory, Colorado State University, (1996).

Seidel, G. E. Jr., "Status of Sexing Semen for Beef Cattle", Texas A & M University 45th Annual Beef Cattle Short Course and Trade Show Proceedings, Aug. 9-11, p. 11124-11127, (1999).

Seidel, G. E. Jr., et al, "Insemination Of Heifers With Very Low Numbers Of Frozen Spermatozoa", CSU, Atlantic Breeders Cooperative, Lancaster, PA, DUO Dairy, Loveland, CO, July (1996).

Seidel, G. E. Jr., et al, "Insemination of Holstein Heifers With Very Low Numbers Of Unfrozen Spermatozoa", CSU, Atlantic Breeders Cooperative, (1995).

Seidel, G. E. Jr., et al, "Sexing Mammalian Sperm—Overview", Therio. 52: 1267-1272, (1999).

Seidel, G. E. Jr., Economics of Selecting for Sex: The Most Important Genetic Trait, Theriogenology 59, (2003), pp. 585-598.

Sell, R. S., et al., "Single-calf Heifer Profitability Compared to Other North Dakota Beef Production Systems." Department of Ag. Eco., North Dakota State University, Ag. Econ. Rpt. 20.; Oct. 1988.

Senger, P. L., et al., "Influence of Cornual Insemination on Conception in Dairy Cattle." J Anim. Sci. 66:3010-3016. (1988).

Shabpareh, V. "Methods for Collecting and Maturing Equine Oocytes in Vitro" Theriogenology 40: 1161-1175, 1993.

Shackelford, S. D., et al, "Effects of Slaughter Age on Meat Tenderness and USDA Carcass Maturity Scores of Beef Females." J. Anim. Sci. 73:3304. (1995).

Shapiro, Howard M. MD., PC. "Practical Flow Cytometry Third Edition," New York 1994.

Sharpe, J.C., et al., "A New Optical Configuration for Flow Cytometric Sorting of Aspherical Cells" Horticulture and Food Research Institute of New Zealand Ltd., Hamilton, New Zealand (PNS) Nov. 2, 1997 Abstract.

Sharpe, Johnathan, Thesis; "An Introduction of Flow Cytometry", Ch. 2-2.2, 1997.

Sharpe, Johnathan, Thesis; "Gender Preselection-Principle Scientific Options," Ch. 3.4-3.4.8, 1997.

Sharpe, Johnathan, Thesis; "Sperm Sexing using Flow Cytometry," Ch. 3.5-3.5.8, 1997.

Sharpe, Johnathan, Thesis; "Sperm Sexing-Method of Johnson et al," Ch. 3.6-4.3.4, 1997.

Shelton, J. N. and Moore, N.W. "The Response of the Ewe to Pregnant Serum Mare Gonadotropin and to Horse Anterior Pituitary Extract." J. Reprod. Fertil. 14:175—177. (1967).

Shilova, A. V., et al., "The Use of Human Chorionic Gonadotropin for Ovulation Date Regulation in Mares." VIIIth Int. Congress On Anim. Repro. and A. I. 204-208. (1976).

Shorthose, W. R. and P. V. Harris. "Effect of Animal Age on the Tenderness of Selected Beef Muscles." J. Food Sci. 55:1-. (1990).

Silbermann, M., "Hormones and Cartilage. Cartilage: Development, Differentiation, and Growth." pp. 327-368. Academic Press, Inc. (1983).

Simon, M., "The Effect of Management Option on the Performance of Pregnant Feedlot Heifers." M.S. Thesis. Kansas State University. (1983).

Skogen-Hagenson, M. J. et al; "A High Efficiency Flow Cytometer," The Journal of Histochemistry and Cytochemistry, vol. 25, No. 7, pp. 784-789, 1977, USA.

Smith, G. C., et al, "USDA Maturity Indexes and Palatability of Beef Rib Steaks." J. of Food Quality 11:1. (1988).

Smith, G. C., et al., "Relationship of USDA Maturity Groups to Palatability of Cooked Beef." J. of Food Sci. 47:1100. (1982).

Smith, R. L., et al, Influence of Percent Egg Yok during Cooling and Freezing on Survival of Bovine Spermatozoa, Dairy Science 1979 J 62:1297-1303.

Solsberry G.U., Van-Denmark N.L., Theory and practice of artificial cow insemination in USA, Moscow, KOLOS Publishing House, 1966, p. 346.

Spectra Physics, The Solid State Laser Company, "Vangaurd 4 Watts of UV from a Quasi-CW, All Solid State Laser," http://www.splasers.com/products/isl_products/vangaurd.html three pages, printed Nov. 14, 2002.

Spectra-Physics Products, "Fcbar" http://www.splasers.com/products/oem_products/ov_fcbar.html two pages printed Nov. 14, 2002.

Spectra-Physics, The Solid State Laser Company, Vanguard 2000-HMD 532, www.specra-physics.com, Copyright 2002.

Spectra-Physics, The Solid State Laser Company, Vanguard 350-HMD 355, www.specra-physics.com Copyright 2002.

Squires, E. L, et al., "Effect of Dose of GnRH Analog on Ovulation in Mares." Therio. 41:757-769. (1994).

Squires, E. L, "Simultaneous Analysis of Multiple Sperm Attributes by Flow Cytometry", Diagnostic Techniques and Assisted Reproductive Technology, the Veterinary Clinics of North America, Equine Practice, vol. 12, No. 1, p. 127-130 (1996).

Squires, E. L., "Early Embryonic Loss" *Equine Diagnostic Ultrasonography*, first ed., Rantanen & McKinnon. Williams and Wilkins, Baltimore, Maryland, p. 157-163 (1998).

Squires, E. L., et al, "Cooled and Frozen Stallion Semen", Bulletin No. 9, Colorado State University, Ft. Collins, CO. (1999).

Squires, E.L., "Procedures for Handling Frozen Equine Semen for Maximum Reproductive Efficiency", (1998) pp. 1, 39-41, 81-89.

Staigmiller, R.B. "Superovulation of Cattle with Equine Pituitary Extract and Porcine FSH" Theriogenology 37: 1091-1099 1992.

Stap J. Et al Improving the Resolution of Cryopreserved X- and Y-Sperm During DNA Flow Cytometric Analysis with the Addition of Percoll to quench the Fluorescence of Dead Sperm: Academic Medical Center, University of Amsterdam (1998) Journal of Animal Science vol. 76 1998, pp. 1896-1902.

Steel, N. L., "Cost Effectiveness of Utilizing Sexed-Semen in a Commercial Beef Cow Operation", MS Thesis, Colorado State University, Summer 1998.

Steinkamp: "Flow Cytometry" vol. 55, No. 9, Sep. 1984 pp. 1375-1400, New York Review of Scientific Instruments Abstract Only.

Stellflug, J. N., "Plasma Estrogens in Periparturient Cow." Therio 10:269. (1978).

Stevenson, J. S., et al., "Detection of Estrus by Visual Observation and Radiotelemetry in Peripubertal, Estrus-Synchronized Beef Heifers." J. Anim. Sci. 74:729. (1996).

Story, C. E., et al., "Age of Calf at Weaning of Spring-Calving Beef Cows and the Effect on Cow and Calf Performance and Production Economics." J. Anim. Sci. 78:1403. (2000).

Stovel R.T. A Means for Orienting Flat Cells in flow systems Biophysical Journal, 1978,vol. 23,pp. 1-5.

Sullivan, J. J., et al., "Duration of Estrus and Ovulation Time in Nonlactating Mares Given Human Chorionic Gonadotropin During Three Successive Estrous Periods." J.A.V.M.A. 162:895-898 (1973).

Sumner, A. T. and Robinson, J. A., "A Difference in Dry Mass Between the Heads of X and Y- Bearing Human Spermatozoa", J Reprod Fertil. 48, p. 9-15 (1976).

Swanson, E. W. "Future Research on Problems of Increasing Meat Production by Early Calving." In: J.C. Taylor (ed.) *The Early Calving of Heifers and its Impact on Beef Production*. (1975).

Swenson, S. L., et al., "PRRS Virus Infection in Boars: Isolation From Semen and Effect on Semen Quality" from the 1995 Research Investment Report, Iowa State University, Veterinary Clinical Sciences, Iowa State University.

Taljaard, T. L., et al., "The Effect of the Laparoscopic Insemination Technique on the Oestrus Cycle of the Ewe." J. South Afr. Vet. Assoc. 62(2):60-61. (1991).

Tatum, J. D., et al., "Carcass Characteristics, Time on Feed and Cooked Beef Palatability Attributes." J. Anim. Sci. 50:833. (1980).

Taylor, C. S., "Efficiency of Food Utilization in Traditional and Sex-Controlled Systems of Beef Production", AFRC Animal Breeding Research Organization, West Mains Road, Edinburg EH9 3JQ; Animal Prod. 1985 40:401-440.

Tervit, H.R., et al., "Successful Culture In Vitro of Sheep and Cattle Ova", Agricultural Research Council, Unit of Reprod. Physio. and Biochem., Univ of Cambridge, p. 493-497 (1972).

Thun, Rico, et al., Comparison of Biociphos-Plus® and TRIS-Egg Yolk Extender for Cryopreservation of Bull Semen; Theriogenology Symposium, Dec. 1999, vol. 52, #8.

Time-Bandwidth Products "GE—100—XHP", www.tbsp.com, 2 pages, Jan. 2002.

Unruh, J. A. "Effects of Endogenous and Exogenous Growth-Promoting Compounds on Carcass Composition, Meat Quality and Meat Nutritional-Value." J. Anim. Sci. 62:1441. (1986).

USDA "Official United States Standards for Grades of Carcass Beef." Agric, Marketing Serv., USDA, Washington, DC. (1997).

Van Dilla, Martin, "Overview of Flow Cytometry: Instrumentation and Data Analysis", Flow Cytometry: Instrumentation and Data Analysis, Van Dilla et al. (Eds.), 1985, pp. 1-8.

van Munster, E. B., et al, "Difference in Sperm Head Volume as a Theoretical Basis for Sorting X & Y-Bearing Spermatozoa: Potentials and Limitations", Therio 52, pp. 1281-1293 (1999).

van Munster, E. B., et al, "Difference in Volume of X- and Y-chromosome Bearing Bovine Sperm Heads Matches Difference in DNA Content" Cytometry vol. 35 p. 125-128 (1999).

van Munster, E. B., et al, "Measurement-Based Evaluation of Optical Path Length Distributions Reconstructed From Simulated Differential Interference Contrast Images", J of Microscopy 191, Pt. 2, p. 170-176 (1998).

van Munster, E. B., et al, "Reconstruction of Optical Pathlength Distributions From Images Obtained by a Wide Field Differential Interference Contrast Microscope", J of Microscopy 188, Pt. 2, p. 149-157 (1997).

Vazquez, J. J. et al., "Nonsurgical Uterotubal Insemination in the Mare", Proceedings of the 44th Annual Convention of the American Association of Equine Practitioners, vol. 44, pp. 68-69 (1998).

Vazquez, J. M., et al., "A. I. in Swine; New Strategy for Deep Insemination with Low Number of Spermatozoa Using a Non-surgical Methodology", 14th International Congress on Animal Reproduction, vol. 2, Stockholm, Jul. 2000, p. 289.

Vazquez, J., et al., "Development of a Non-surgical Deep Intra Uterine Insemination Technique", Boar Semen Preservation IV, IVth International Conference on Boar Semen Preservation, Maryland, Aug. 8, 1999, pp. 262-263.

Vazquez, J., et al., "Hyposmotic Swelling Test as Predictor of the Membrane Integrity in Boar Spermatozoa", Boar Semen Preservation IV, IVth International Conference on Boar Semen Preservation, Maryland, pp. 263., Jun. 2004.

Vazquez, J. et al., "Successful low dose insemination by a fiber optic Endoscope technique in the Sow", Proceedings Annual Conference of the International Embryo Transfer Society, Netherlands, Theriogenology, vol. 53 Jan. 2000.

Vidament, M., et al., "Equine Frozen Semen Freezability and Fertility Field Results." Therio. 48:907. (1997).

Vincent, B.C., et al, "Carcass Characteristics and Meat Quality of Once-Calved Heifers." Canadian J. Anim. Sci. 71:311. (1991).

Vogel, T., et al, "Organization and Expression of Bovine TSPY", Mammalian Genome, vol. 8, pp. 491-496 (1997).

Voss, J. L. and Pickett, B. W., "Reproductive Management of the Broodmare." CSU Exp. Sta. Anim. Reprod. Lab. Gen. Series. Bull. 961 (1976).

Voss, J. L. et al., "Effect of Number and Frequency of Inseminations on Fertility in Mares." J. Reprod. Fertil. Suppl. 32:53-57. (1982).

Voss, J. L., et al., Effect of Human Chorionic Gonadotropin on Duration of Estrous Cycle and Fertility of Normally Cycling, Nonlactating Mares. J.A.V.M.A. 165:704-706. (1974).

Waggoner, A. W., et al., "Performance, Carcass, Cartilage Calcium, Sensory and Collagen Traits of Longissimus Muscles of Open Versus 30-month-old Heifers That Produced One Calf." J. Anim. Sci. 68:2380. 1990.

Watson, "Recent Developments and Concepts in the Cryopreservvation of Spermatozoa and the Assessment of Their Post-Thawing Function," Reprod. Fertil. Dev. 7:871-891 (1995) Abstract.

Welch G., et al., Fluidic and Optical Modifications to a FACS IV for Flow Sorting of X- and Y- Chromosome Bearing Sperm Based on DNA. Cytometry 17 (Suppl. 7): 74. (1994).

Welch, G., et al., "Flow Cytometric Sperm Sorting and PCR to Confirm Separation of X- and Y- Chromosome Bearing Bovine Sperm", Animal Biotechnology, 6, pp. 131-139 (1995).

Wheeler, T. L., et al., "Effect of Marbling Degree on Beef Palatability in Bos-taurus and Bos-indicus cattle." J. Anim. Sci. 72:3145. (1994).

Wickersham, E. W. and L. H. Schultz. "Influence of Age at First Breeding on Growth, Reproduction, and Production of Well-Fed Holstein Heifers." J. Dairy Sci. 46:544. (1963).

Wilhelm, K.M. et al, "Effects of Phosphatidylserine and Cholesterol Liposomes on the Viability, Motility, and Acrosomal Integrity of Stallion Spermatozoa Prior to and after Cryopreservation", Cryobiology 33:320, 1996.

Wilson, C. G., et al., "Effects of Repeated hCG Injections on Reproductive Efficiency in Mares." Eq. Vet. Sci. 4:301-308. (1990).

Wilson, D. E. et al., "Mammal Species of the World", Smithsonian Institution Press, 1993, 1206 pp.

Wilson, M.S. "Non-surgical Intrauterine Artificial Insemination in Bitches Using Frozen Semen." J. Reprod. Fertil. Suppl. 47:307-311. (1993).

Windsor, D. P., et al, "Sex Predetermination by Separation of X and Y Chromosome-bearing Sperm: A Review", Reproduction of Fertilization and Development 5, pp. 155-171, (1993).

Wintzer Et al.:"Krankheiten des Pferdes Ein Leitfaden fur Studium und Praxiz," 1982, Parey, Berlin Hamburg XP002281450.

Woods, G. L. and Ginther, O. J. "Recent Studies Related to the Collection of Multiple Embryos in Mares." Therio. 19:101-108. (1983).

Woods, J., et al., "Effects of Time of Insemination Relative to Ovulation on Pregnancy Rate and Embryonic-Loss Rate in Mares." Eq. Vet. J. 22(6): 410-415. (1990).

Zhou, Hongwei, et al. "Research on and Development of Flow Cell Sorting Apparatuses," Gazette of Biophysics, vol. 13, ed. 3, 1997.

Hermesmeyer, G.N. ,et al. Effects of Lactation and Prenatal Androgenization on the Performance, Carcass Composition, and Longissimus muscle sensory characteristics of heifers in the single-calf heifer system. The Professional Animal Scientist 15: 14-23, (1995).

Seidel, G. E. Jr., "Fertility of Bulls on the Edge of the Dose-Response Curve for Numbers of Sperm per Inseminate"; Proceedings of the 17th Technical comference on Artificial Insemination & Reproduction, 1998.

Hollinshead, F.K. et al. "In vitro and in vivo assessment of functional capacity of flow cytometrically sorted ram spermatozoa after freezing and thawing." Reprod. Fertil. And Develop. 2003. vol. 15, pp. 351-359.

Hollinshead F. K. et al. "Production of lambs of predetermined sex after the insemination of ewes with low numbers of frozen-thawed sorted X- or Y- Chromosome-bearing spermatozoa", Reprod. Fertil. And Develop. 2002, vol. 14, pp. 503-508.

Hollinshead F. K. et al. "Sex-Sorting and Re-cryopreservation of Frozen-Thawed Ram Sperm for In Vitro Embryo Production" Theriogenology, vol. 59. (2003) pp. 209.

Dhali et al. Vitrification of Buffalo (*Bubalus bubalis*)Oocytes, Embryo Theriogenology vol. 53, pp. 1295-1303 (2000).

Borini et al. Cryopreservation of Mature Oocytes: The use of a trypsin inhibitor enhances fertilization and obtained embryos rates, Fertil. Steril. (1997), vol. 68 (Suppl.).

Hamamatsu Photonics K.K. Electronic Tube Center, Photomultiplier Tubes, Brochure Dec. 1997.

Johnson, L. A., et al. The Beltsville Sperm Sexing Technology: High-speed sperm sorting gives improved sperm output for In Vitro fertiliation and AI, Journal of Animal Science, vol. 77, Suppl 2/J, Dairy Sci. vol. 82, Suppl. Feb. 1999 pp. 213-220.

Peters D., The LLNL high-speed sorter: Design features, operational characteristics, and bioloical utility, Cyometry, 6:290-301 (1985).

Rens W., et al Slit-scan flow cytometry for consistent high resdolution DNA analysis of X- and Y- chromosome bearing sperm, Cytometry 25:191-199 (1996).

van Munster, E. B. Interferometry in flow to sort unstained X- and Y-Chromosome-Bearing Bull Spermatozoa, Cytometry 47:192-199 (2002).

Scmid, R. L., et al. Effects of follicular fluid or progesterone on in vitro maturation of equine oocytes before intracytoplasmic sperm injection with non-sorted and sex-sorted spermatozoa, Journal of Reproduction and Fertility 56:519-525, 2000.

Brink, Z et al. A reliable procedure for superovulating cattle to obtain zygotes and early emryos for microinjection, Theriogenology vol. 41, p. 168, (1994).

Spectra-Physics, The Solid State Laser Company, Vanguard 350-HMD 355, User's Manual, Dec. 2002.

Photon, Inc. Light MeasuringSolutions, NanoScan for High-powered beam Applications, 2005.

Fluorescense Lifetime Systems, www.picoquant.com, Jan. 28, 2005 pp. 2.

NCI ETI Branch, Flow CytometryCore Laboratory, http://home.ncifcrf.gov/ccr/flowcore/ndyag.htm, pp. 5, Jan. 11, 2004.

NCI ETI Branch, Flow CytometryCore Laboratory, http://home.ncifcrf.gov/ccr/flowcore/lsrll.htm, pp. 14, May 11, 2004.

Saacke, R.G., Can Spermatozoa with abnormal heads gain access to the ovum in artificially inseminated super- and single-ovulating cattle?, Theriogenology 50:117-128 1998.

Hawk, H.W., Gamete Transport in the Superovulated Cow. Theriogenology: Jan. 1998 vol. 29 No. 1 pp. 125-142.

Blecher, S.R., et al. A new approach to immunological sexing of sperm, Theriogenology, 59, pp. 1309-1321, 1999 vol.

Wheeler, M. B., et al. Application of sexed semen technology to in vitro embryo production in cattle, Theriogenology, vol. 65 (2006) 219-227.

Garverick, H. A., et al. mRNA and protein expression of P450 aromatase (AROM) and estrigen receptors (ER) $\alpha$ and $\beta$ during early development of bovine fetal ovaries; The society for the study of reproduction 38th annual meeting Jul. 24-27, 2005; Abstract only.

Bodmer, M., et al., Fertility in heifers and cows after low does insemination with sex-sorted and non-sorted sperm under field conditions; Theriogenology, vol. 64, (2005) 1647-1655.

Schenk J. L., et al. Embryo production from superovulated cattle following insemination of sexed sperm, Theriogenology, 65 (2006) 299-307.

Garner, D. L., Flow cytometric sexing of mammalian sperm, Theriogenology, 65 (2006) 943-957.

Habermann F. A., et al., Validation of sperm sexing in the cattle (*Bos taurus*) by dual colour flourescence in situ hybridization; J Anim Breed Genet. Apr. 2005; 122 Suppl 1:22-7 (Abstract only).

Seidel, G.E. Jr., et al., Methods of Ovum Recovery and Factors Affecting Fertilization of Superovulated Bovine Ova, Control of Reproduction in the Cow, Sneenan ed., 1978, pp. 268-280.

Hawk, H. W. et al., Effect of Unilateral Cornual Insemination upon Fertilization Rate in Superovulating and Single-Ovulating Cattle, Journal of Animal Sciences, 1986 vol. 63, pp. 551-560.

Andersson, M. et al., Pregnancy Rates in Lactating Holstein-Greisian Cows after Artificial Insemination with Sexed Sperm. Reprod. Dom. Anim 41, 95-97, 2006.

Morton, K. M., et al., In vitro and in vivo survival of bisected sheep embryos derived from frozen-thawed unsorted, and frozen-thawed sex-sorted and refrozen-thawed ram spermatozoa; Theriogenology, 65 (2006) 1333-1345.

Wilson, R. D., et al., In vitro production of bovine embryos using sex-sorted sperm, Theriogenology, 65 (2006) 1007-1015.

Johnson, L.A., et al, 1996 Gender preselection in mammals. XX Beltsville Symposium in Agricultural Research Technology's Role in the Genetic Improvement of Farm Animals. pp. 151-164, Amer. Soc. Anim. Sci. IL, USA.

Smorag, Z., et al., Cattle Sex Regulation by Separation of X and Y Spermatozoa—Preliminary Results of Field Experiment in Poland, Reproduction, Fertility and Development 17(2) 306-306; Jan. 1, 2005.

Crichton, E., et al. (Abstract) Artificial Insemination of Lactating Holstein Cows with Sexed Sperm, Reproduction, Fertility and Development 18(2) 281-281, Dec. 14, 2005.

Lindsey, A.C., et al. Hysteroscopic insemination of low numbers of flow sorted fresh and frozen/thawed stallion spermatozoa, Equine Vet J. Mar. 2002;34(2):106-7.

Drobnis, E. Z, Cold shock damage is due to lipid phase transitions in cell membranes : a demonstration using sperm as a model, Journal of experimental zoology (J. exp. zool.) 1993, vol. 265, No. 4, pp. 432-437 (22 ref.).

Hagele, W.C., et al., Effect of Separating Bull Semen into X and Y Chromosome-bearing Fractions on the Sex Ratio of Resulting Embryos; Cran J. Comp. Med, 1984: 48:294-298.

U.S. Appl. No. 11/422,735, filed May 25, 2006 entitled Apparatus, Methods and Processes for Sorting Particles and for Providing Sex-Sorted Animal Sperm.

Suh, T.K, et al., Pressure during flow sorting of bull sperm affects post-thaw motility characteristics; Theriogenology vol. 59, No. 1, Jan. 2003 p. 516.

Rath, D, et al., In Vitro Production of Sexed Embryos for Gender Preselection: High-speed sorting of X-Chromosome-Bearing Sperm to Produce Pigs After Embryo Transfer, J. Anim. Sci. 1999, 77:3346-3352.

Auchtung, T.L., et al., Effects of Photoperiod During the Dry Period on Prolactin, Prolactin Receptor, and Milk Production of Dairy Cows; Journal of Dairy Sci. 88: 121-127; American Dairy Sci. Assoc., 2005.

Bailey, T. et al., Milk Production Evaluation In First Lactation Heifers; 1999 Virginia Cooperation Extension/Dairy Science Publication 404-285.

Belloin, J.C., Milk and Dairy products: prduction and processing costs Food and Agriculture Organization of United Nations Rome 1988 FAO; web page where found: www.fao.org/docrep/003/x6931e/X6931E00.htm.

Lopez, H. et al., Relationship Between Level of Milk Production and Multiple Ovulation in Lactating Dairy Cows Journal of Dairy Sci. 88:2783-2793; American Dairy Science Association, 2005.

Milk Production and Biosynthesis University of Guelph/Dairy Science and Technology (1998) www.foodsci.uoguelph.ca/dairyedu/biosyntheses.html.

Milk Production, Released Jul. 18, 2006, by the National Agricultural Statistics Service (NASS), Agri. Stats. Board, US Dept. of Agri.

De Vries, A. Economic Value of Pregnancy in Dairy Cattle Journal of Dairy Sci. 89:3876-3885/American Dairy Sci. Assoc. 2006.

Wong, P.Y.D., et al. Potassium Movement During sodium-Induced Motility Initiation in the Rat Caudal Epididymal Spermatozoa; Biology of Reproduciton 28, 206-212 (1983).

Shirai, H., et al. Regulation of Sperm Motility in Starfish; Development, Growth, and Differentiation; 24, (5), 419-428 (1982).

Padilla, A.W. et al. Extender and Centrifugation Effects on the Motility Patterns of Slow-Cooled Stallion Spermatozoa; J. Anim. Sci 1991, 69:3308-3313.

Ohta H., et al., Acquisition and Loss of Potential for Motility Ofspermatozoa of the Japanese Eel Anguilla Japonica, National Research Institute of Aquaculture, UNJR Aquiculture; 28th Panel Proceedings (1999).

Morisawa, M. The Process of the Initiation of Sperm Motility; Laboratory of Physiology, Ocean Research Institute, University of Tokyo (1986).

McGrady, A.V., et al. Cholinergic Effects on Bull and Chimpanzee Sperm Motility; Biology of Reproduciton 15, 248-253 (1976).

Klinc, P. Dissertation—Improved Fertility of Flowcytometrically Sex Selected Bull Spermatozoa , School of Veterinary Medicine Hanover Germany, 2005.

Jenkins, A. D., et al. Concentrations of Seven Elements in the Intraluminal Fluids of the Rat Seminiferous Tubules, ReteTestis, and Epididymis; Biology of Reproduciton 23, 981-987 (1980).

Darszon, A., et al. Ion Channels in Sperm Physiology, Physiological Reviews, vol. 27, No. 2, Apr. 1999.

Babcock, D. F., et al. Potassium-dependent increases in cytosolic pH stimulate metabolism and motility of mammalian sperm, Proc. Natl. Acad. Sci. USA, vol. 80, pp. 1327-1331, Mar. 1983.

Zilli, L., et al. Adenosine Triphosphate Concentration and -D-Glucuron idase Activity as Indicators of Sea Bass Semen Quality; Biology of Reproduction 70, 1679-1684 (2004).

Hanania, E. G, et al. A novel Automated Method of Scanning Cytometry and Laser-Induced Necrosis Applied to Tumor Cell Purging, Blood. Nov. 15, 1999, vol. 94, No. 10, suppl 1 part 1.

Purdy, P. H. et al., Effect of Adding Cholesterol to Bull Sperm Membranes on Sperm Capacitation, the Acrosome Reaction, and Fertility, Biology of Reproduction 71, 522-527 (2004).

Purdy, P. H. et al., Effect of cholesterol-loaded cyclodextrin on the cryosurvival of bull sperm, Cryobiology 48 (2004) 36-45.

Moce E., et al., Cholesterol-loaded cyclodextrins added to fresh bull ejaculates improve sperm cryosurvival, J. Anim. Sci, 2006, 84:826-833.

Ereth, B.A., et al. Integration of Early Weaning and Sexed Semen into a Single-Calf Heifer System to Increase Value of Non-Replacement Heifers; Proceedings, Western Section, American Society of Animal Science, vol. 51,441-443, Jun. 2000.

Ereth, B.A., et al. Integration of Early Weaning and Sexed Semen into a Single-Calf Heifer System to Increase Value of Non-Replacement Heifers; Abstract Only, Journal of Animal Science, vol. 78, Supplement 2, 2000.

Bavister, B.D. et al., The effects of Sperm Extracts and Energy Sources on the Motility and Acromosome Reaction of hamster Spermatozoa in vitero; Biology of Reporduction 16, 228-237 (1997).

Fattouh, El-S.M. et al., Effect of Caffine on the Post-Thaw Motility of Buffalo Spermatozoa; Theriogenology, Jul. 1991, vol. 36 No. 1.

Koh-ichi Hamano, et al., Gender Preselection in Cattle with Intracytoplasmically injected, flow cytometrically sorted sperm heads, Biology of Reproduction 60, 1194-1197 (1990).

Hollinshead, F.K. et al., Birth of lambs of pre-determined sex after in vitro production of embryos using frozen-thawed sex-sorted and re-frozen-thawed ram spermatozoa, Reproduction (Cambridge, England) May 2004, vol. 127, o. 5, pp. 557-568.

Nikkei Biotech, Supplement, Latest Information of Biological Instruments and Reagents, 1988, pp. 93-94.

Pursley, J.R. et al., Reproductive Management of Lactating Dairy Cows Using Synchronization of Ovulation; 1997 J. Dairy Sci 80:301-306.

Bagnato, A., Genetic and Breeding; Phenotypic Evaluation of Fertility Traits and Their Association with Milk Production of Italian Friesian Cattle; 1994 J. Dairy Sci 77:874-882.

Panskowski, J., A., et al. Use of Prostaglandin F2a as a Postpartum Reproductive Management Tool for Lactating Dairy Cows; 1995 J. Dairy Sci 78:1477-1488.

Scipioni, R. L., et al., Short Communication: An Electronic Probe Versus Milk Protesterone as Aids for Reproductive Management of Small Dairy Herds; 1999 J. Dairy Sci 82:1742-1745.

Grant, V. J., et al., Sex-Sorted Sperm and Fertility: An Alternative View; Biology of Reproduction 76, 184-188 (2007).

Garner, D. L., Sex-Sorting Mamallian Sperm: Concept to Application in Aminals; Journal of Andrology, vol. 22, No. 4 Jul./Aug. 2001.

Tubman, L.M. et al., Characteristics of calves produced with sperm sexed by flow cytometry/cell sorting; 2004 Amer. Society of Animal Sciences; 82:1029-1036.

Weigel, K. A., Exploring the Role of Sexed Semen in Dairy Production Systems; J. Dairy Sci. 87: (E.Suppl.): E120-E130; 2004 American Dairy Science Assoc.

Ferre, L., In vitro-derived embryo production with sexed and unsexed semen from different bulls; Reproduction Fertility and Development, vol. 16, Part 1/2, p. 253, 2004.

Dransfield, M.B.G., et al., Timing of Inseminatio for Dairy Cows Identified in Estrus by a Radiotelemetric Etrus Detection System. 1998 J Dairy Sci. 81: 1874-1882.

Nebel, R.L. et al. Timing of Artificial Insemination of Dairy Cows: Fixed Time Once Daily Versus Morning and Afternoon 1994 J Dairy Sci. 77:3185-3191.

Pursley, J. Richard, et al. Effect of Time of Artificial Insemination on Pregnancy Rates, Calving Rates, Pregnancy Loss, and Gender Ratio After Synchronization of Ovulation in Lactating Dairy Cows. 1998 J Dairy Sci. 81: 2139-2144.

Rozeboom, K. J. et al. Late Estrus or Metestrus Insemination After Estrual Inseminations Decreases Farrowing Rate and Litter Size in Swine J. Animal Sci. 1997. 75:2323-2327.

Peeler, I. D. et al. Pregnancy Rates After Times Al of Heifers Following Removal of Intravaginal Progesterone Inserts, J. Dair Sci., 87:2868-2873; 2004.

Rath, D. Low Dose Insemination in the Sow—A Review, Reprod. Dom Anim. 37, 201-205 (2002) www.blackwell.de/synergy.

Lukaszewicz, M. et al. Attempts on freezing the Greylag (*Anser anser L.*) gander semen Animal Reproduction Science 80 (2004) 163-173.

Foote, R. H. et al. Sperm Numbers Inseminated in Dairy Cattle and Nonreturn Rates Revisited 1997 J Dairy Science 80:3072-3076.

Conley, H.H. et at. Intensification by Intrauterine Devices of Sperm Loss from the Sheep Uterus Biology of Reproduction 2, 401-407 (1970).

Chrenek, Peter et al. Fertilizing Capacity of Transgenic and Non-Transgenic Rabbit Spermatozoa after Heterospermic Insemination Bull Vet. Inst. Pulawy 49, 307-310, 2005.

Johnson L.A., et al. use of boar spermatozoa for artificial insemination, II. Fertilization Capacity of fresh and frozen spermatozoa in gilts inseminated either at a fixed time or according to walsmeta readings, Journal of Animal Science, vol. 54 No. 1, 1982 pp. 126-131.

Pursel, V. G., et al. Distribution and morphology of fresh and frozen-thawed sperm in the reproductive tract of gilts after artificial insemination; Biology of Reproduction 19, 69-76 (1978).

Rath, D., "On the Status of Sex-Specific Sperm Sorting" Review lecture ET Conference 2002, Department of Animal Production and Animal Behaviour, Mariensee, Germany.

Grossfeld, R., "Experiments to Improve the Quality of Sex-Sorted Fresh and Frozen Procine Spermatozoa" PhD thesis of the Faculty of Agricultural Sciences, Georg-August University, Gottingen, May 2007.

de Graaf, S.P. et al., Birth of offspring of pre-determined sex after artificial insemination of frozen-thawed, sex-sorted and re-frozen-thawed ram spermatozoa, Theriogenology, 67 (2007) 391-398.

O'Brien, J.K. et al., Development fo sperm sexing and associated assisted reproductive technology for sex preselection of captive bottlenose dolphins, Reproduction Fertility and Development, 2006, 18, 319-329.

Best, "Nuclear Localization of Pyrrole-Imidazole Polyamide-Flourescein Conjugates in Cell culture," 2003, PNAS, 100/21, pp. 12063-12068.

Cullilng, "Handbook of Histopathological and Histochemical Techniques," 3rd Ed., Butterworths, pp. 192 Feb. 1975.

DePauw, "Sperm Binding to Epithelial Oviduct Explants in Bulls with Different Nonreturn Rates Investigated with a New in Vitro Model," 2002, Biol Reprod, 67, pp. 1073-1079.

Sabeur, "Effects of Angiotensin II on the Acrosome Reaction in Equine Spermatozoa," 2000, J Reprod Fert, 120, pp. 135-142.

Salisbury, "Reversal by Metabolic Regulators of CO2-induced Inhibition of Mammalian Spermatozoa," 1959, Proc Soc Exp Biol Med, 101/1, pp. 187-189.

Millipore Specialty Media, IVF Protocol, Website, http//www.specialtymedia.com/05Resources/Protocols/ivfprotocol.htm May 2007.

Arndt-Jovin, "Analysis and Sorting of Living Cells According to Deoxyribonucleic Acid Content," 1977, J. Histochem Cytochem, 25/7, pp. 585-589.

Baumber, "The Effect of Reactive Oxygen Species on Equine Sperm Motility, Viability, Acrosomal Integrity, Mitochondrial Membrane Potential, and Membrane Lipid Peroxidation," 2000, J. Andrology, 21/6, pp. 895-902.

Bencic, "Carbon Dioxide Reversibly Inhibits Sperm Motility and Fertilizing Ability in Steelhead (*Oncorhynchus mykiss*)," 2000, Fish Physiology and Biochemistry, 23/4, pp. 275-281.

Boatman, "Bicarbonate Carbon Dioxide Regulation of Sperm Capacitation Hyperactivated Motility and Acrosome Reactions," 1991, Biol of Reprod, 44/5, pp. 806-813.

Bruemmer, "Effect of Pyruvate on Function of Stallion Spermatozoa Stored for up to 48 Hours," 2002, J Anim Sci, 80/1, pp. 12-18.

D'Occhio, "Sexing of Sperm and Embryos: Use of Sexed Sperm in AI, IVF, ICSI and Graft," Animal Breeding Use of New Technologies, Chapter 19, pp. 247-264, Kinghorn, van der Werf and Ryan, Eds., May 2007.
Denniston, "Effect of Antioxidants on the Motility and Viability of Cooled Stallion Spermatozoa," 2001, J. Reprod Fert, Supp 56, pp. 121-126.
Dresser, "Analyses of DNA Content of Living Spermatozoa Using Flow Cytometry Techniques," 1993, J Reprod Fert, 93, pp. 357-365.
Ericsson, "Flow Cytometric Evaluation of Cryopreserved Bovine Spermatozoa Processed Using a New Antiobiotic Combination," 1990, Theriogenology, 33/6, pp. 1211-1220.
Farrell, "Quantification of Bull Sperm Characteristics Measured by Computer-Assisted Sperm Analysis (CASA) and the Relationship of Fertility," 1998, Theriogenology, 49/4, pp. 871-879.
Foote, "Motility and Fertility of Bull Sperm in Whole Milk Extender Containing Antioxidants," 2002, Animal Repro Sci, 71/1-2, pp. 13-23.
Garcia, M.A., et al., "Development of a Buffer System for Dialysis of Bovine Spermatozoa Before Freezing III. Effect of Different Inorganic and Organic Salts on Fresh and Frozen-Thawed Semen," 1989, Theriogenology, 31/5, pp. 1039-1048.
Garner, "Viability Assessment of Mammalian Sperm Using SYBR-14 and Propidium Iodide," 1995, Bio of Reprod, 53, pp. 276-284.
Gordon, "Genetic Transformation of Mouse Embryos by Microinjection of Purified DNA," 1980, PNAS, 77/12, pp. 7380-7384.
Graves, "Metabolism of Pyruvate by Epididymal-Like Bovine Spermatozoa," 1964, J Dairy Sci, 47/12, pp. 1407-1411.
Graves, "Metabolic End-products of Anaerobic Spermatozoan Metabolism," 1966, Nature, 211, pp. 308-309.
Guthrie, "Flow Cytometric Sperm Sorting: Effects of Varying laser Power on Embryo Development in Swine," 2002, Mol Reprod and Develop, 61/1, pp. 87-92.
Gygi, "Use of Fluorescent Sequence-Specific Polyamides to Discriminate Human Chromosomes by Microscopy and Flow Cytometry," 2002, Nucl Acids Res, 30/13, pp. 2790-2799.
Johnson, "Modification of a Laser-Based Flow Cytometry for High-Resolution DNA Analysis of Mammalian Spermatozoa," 1986, Cytometry, 7, pp. 268-273.
Johnson, "Flow Cytometry of X and Y Chromosome-Bearing Sperm for DNA Using an Improved Preparation Method and Staining with Hoechst 33342," 1987, Gamete Research, 17, pp. 203-212.
Johnson, "Sex Preselection in Swine: Altered Sex Ratios in Offspring following Surgical Insemination of Flow Sorted X- and Y-Bearing Sperm," 1991, Reprod Dom Anim, 26, pp. 309-314.
Johnson, "Sex Preselection by Flow Cytometric Separation of X and Y Chromosome-Bearing Sperm Based on DNA Difference: A Review," 1995, Reproduction, Fertility and Development, 7(4), pp. 893-903.
Johnson, "Advances in Gender Preselection in Swine," 1997, J Reprod Fert., Proceedings of the Fifth International Conference on Pig Reproduction, Suppl. 52, pp. 255-266.
Johnson, "Enhanced Flow Cytometric Sorting of Mammalian X and Y Sperm: High Speed Sorting and Orienting Nozzle for Artificial Insemination," 1998, Theriogenology, 49(1), p. 361.
Johnson, "Sex Preselection: High-Speed Flow Cytometric Sorting of X and Y Sperm for Maximum Efficiency," 1999, Theriogenology, 52, pp. 1323-1341.
Johnson, "Sexing Mammalian Sperm for Production of Offspring: the state-of-the-art," 2000, Anim Reprod Sci, 60-61, pp. 93-107.
Karow, "Effects of Temperature, Potassium Concentration, and Sugar on Human Spermatozoa Motility: A Cell Preservation Model from Reproductive Medicine," 1992, Cryobiology, 29, pp. 250-254.
Lodge, "Carbon Dioxide in Anaerobic Spermatozoan Metabolism," 1968, J Dairy Sci, 51/1, pp. 96-103.
Maxwell, "Chlortetracycline Abalysis of Boar Spermatozoa After Incubation, Flow Cytometric Sorting, Cooling, or Cryopreservation," 1997, Mol Reprod Develop, 46, pp. 408-418.
Morrell, "Sexing of Sperm by Flow Cytometry," 1988, The Veterinary Record, 122/14, pp. 322-324.
Partsch, "Scrotal Temperature is Increased in Disposable Plastic Lines Nappies," 2000, Arch Dis Child, 83, pp. 364-368.

Rath, "Production of Piglets Preselected for Sex Following In Vitro Fertilization with X and Y Chromosome-Bearing Spermatozoa Sorted by Flow Cytometry," 1997, Theriogenology, 47, pp. 795-800.
Salisbury, "Preservation of Bovine Spermatozoa in Yolk-Citrate Diluent and Field Results from its Use," 1941, J Dairy Sci, 24/11, pp. 905-910.
Salisbury, "Substrate-Free Epididymal-Like Bovine Spermatozoa," 1963, J Reprod Fertil, 6, pp. 351-359.
Schenk, "Cryopreservation of Flow-Sorted Bovine Spermatozoa," 1999, Theriogenology, 52, pp. 1375-1391.
Seidel, "Artificial Insemination of Heifers with Cooled, Unfrozen Sexed Semen," 1998, Theriogenology, 49/1, p. 365.
Seidel, "Insemination of Heifers with Sexed Sperm," 1999, Theriogenology, 52, pp. 1407-1420.
Seidel, "Insemination of Heifers with Sexed Frozen or Sexed Liquid Semen," Website www.cvmbs.colostate.edu, Abstract, Jun. 3, 1999, 2 pages.
U.S. Patent No. 5,135,759, File History, Johnson Aug. 2009.
Physiology of Reproduction and Artificial Insemination of Cattle, 1978, 2nd Edition, Chap. 16-18, pp. 442-576, Edited by G.W. Salisbury, N.L. VanDemark, J.R. Lodge, published by W.H. Freeman Co., San Francisco, CA.
Zhang, M, et al., In vitro fertilization with flow-sorted buffalo sperm, Reproduction Fertility and Development, 2005, 18(2), 283-284.
Schenk, J.L. et al., Insemination of cow elk with sexed frozen semen, 2003 Theriogenology 59, 514.
BD Biosciences Brochure, BD FACSCalibur Flow Cytometer, the Automated, Multicolor Flow Cytometry System, 2006.
Johnson, L. A. et al., Cryopreservation of flow cytometrically sorted boar sperm: effects on in vivo embryo developmen; J. Anim Sci. vol. 78, Suppl 1/J. Dairy Sci., vol. 83, Suppl 1, 2000.
Lindsey, A., et al., "Hysteroscopic Insemination of Fresh and Frozen Unsexed and Sexed Equine Spermatozoa", pp. 152-153, Proc. 5th Int. Symp. Equine Embryo Transfer, p. 13, 2000.
Presicce, G.A., et al., First established pregnancies in mediterranean italian buffaloes (*Bubalus bubalis*) following deposition of sexed spermatozoa near the utero tubal junction, Reproduction in Domestic Animals, vol. 40, No. 1, Feb. 2005 , pp. 73-75(3).
Dielemann, S.J., Superovulation in cattle: from understanding the biological mechanisms to genomics of the oocyte; $23^{rd}$ Annual Meeting A.E.T.E.—Alghero; Sep. 2007.
Hasler, J. F., Factors influencing the success of embryo transfer in cattle; $23^{rd}$ World Buiatrics Congress, Quebec, Canada Jul. 2004.
Mapletoft, R. J. et al., Superovulation in perspective, Bioniche Animal Health, Dec. 2002.
Bahr, G.F.et al., Considerations of volume, mass, DNA, and arrangement of mitochondria in the midpiece of bull spermatozoa, Experimental Cell Research 60 (1970) 338-340.
Bermudez, D.et al., The immediate effect of IR, laser radiation on rat , germ, cells, was studied by cytophotometric quantification, Scisearch 2001.
Brooks, D.E., Manipulation of Mammalian Gametes in Vitro, Biennial Report, Waite Agricultural Research Institute 1986-1989.
Catt, S.L. et al., Hoechst staining and exposure to UV laser during flow cytometric sorting does not affect the frequency of detected endogenous DNA nicks in abnormal and normal human spermatozoa, Molecular Human Reproduction vol. 3 No. 9 pp. 821-825,(1997).
Chen, Y. et al., Effects of sucrose, trehalose, hypotaurine, taurine, and blood serum on survival of frozen bull sperm, Cryobiology 30, 423-431 (1993).
Conover,J. et al., Pre-loading of mouse oocytes with DNA-specific fluorochrome (Hoechst 33342) permits rapid detection of sperm-oocyte fusion, Journals of Reproductive & Fertility Ltd. 82, 681-690 (1988).
Cressman, B.E. MD, et al., Effect of sperm dose on pregnancy rate from intrauterine insemination: a retrospective analysis, Texas Medicine, 92:74-79 (1996).
Crissman, H.A. et al., Use of DIO-C5-3 to improve hoechst 33342 uptake, resolution of DNA content, and survival of CHO cells, Experimental cell research 174: 338-396 (1988).
De Grooth, B. et al., Simple delay monitor for droplet sorters, Cytometry 12:469-472 (1991).

Delgado, N. et al., Correlation between sperm membrane destabilization by heparin and aniline blue staining as membrane integrity index, Archives of Andrology 40:147-152 (1998).

Donoghue, A. et al., Effects of water- and lipid-soluble antioxidants on turkey sperm viability, membrane integrity, and motility during liquid storage, Poultry Science 76:1440-1445 (1997).

Zucker, R. et al., Utility of light scatter in the Morphological analysis of sperm, Cytometry 13:39-47 (1992).

Ericsson, S. et al., Interrelationships among fluorometric analyses of spermatozoal function, classical semen quality parameters and the fertility of frozen-thawed bovine spermatozoal, Theriogenology 39:1009-1024 (1993).

Esteves, S. et al., Improvement in motion characteristics and acrosome status in cryopreserved human spermatozoa by swim-up processing before freezing, Human Reproduction vol. 15 No. 10 pp. 2173-2179 (2000).

Evenson, D. et al., Physiology and Management, Rapid determination on sperm cell concentration in bovine semen by flow cytometry, J Dairy Sci. 76: 86—94 (1993).

Foote, R., The history of artificial insemination: Selected notes and notables, American Society of Animal Science (2002).

Zhanga, M. et al., Development of bovine embryos after in vitro fertilization of oocytes with flow cytometrically sorted, stained and unsorted sperm from different bulls, Abstract: Theriogenology vol. 60 Issue 9, pp. 1657-1663, Dec. 2003.

Johnson, L. et al., Recent advances in sex preselection of cattle: Flow cytometric sorting of X-&Y-chromosome bearing sperm based on DNA to produce progeny, Theriogenology 41:51-56 (1994).

Ashwood-Smith, M., Debate Human sperm sex selection, Human Reproduction vol. 9 No. 5 pp. 757-759 (1994).

Pinkel, D. et al., Flow cytometry of mammalian sperm progress in DNA and morphology measurement, The Journal of Histochemical and Cytochemistry vol. 27 No. 1 pp. 353-358 (1979).

Johnson, L. et al., Flow sorting of X and Y Chromosome-bearing Mammalian sperm: Activation and pronuclear development of sorted bull, boar, and ram sperm microinjected into hamster oocytes, Gamete Research 21:335-343 (1988).

Centola, G. et al., Cryopreservation of human semen. Comparison of cryopreservatives, sources of variability, and prediction of post-thaw survival. PMID: 1601749 May-Jun. 1992.

Eiman, M. et al., Trehalose-enhanced fluidity of the goat sperm membrane and its protection during freezing, Biology of Reproduction 69: 1245-1250 (2003).

Foote, R. et al., Physiology and Management, Fertility of bull spermatozoa frozen in whole milk extender with trehalose, taurine, or blood serum, J. Dairy Sci. 76:1908-1913 (1993).

Johnson, L. et al., Storage of bull semen, Animal Reproduction Science 62: 143-172 (2000).

Johnson, L. et al., Erratum to "Storage of bull semen", Animal Reproduction Science 62: 143-172 (2000).

McNutt, T. et al., Electrophoretic gel analysis of Hoechst 33342 stained and flow cytometrically sorted bovine sperm membrane proteins, Reprod. Dom Anim. 31: 703-709 (1996).

Agarwal, A. et al., Filtration of spermatozoa through L4 membrane: a new method, Fertility and Sterility, vol. 06, No. 6, Dec. 1991.

Anzar, M. et al., Optimizing and Quantifing fusion of liposomes to mammalian sperm using resonance energy transfer and flow cytometric methods, Cytometry 49:22-27 (2002).

Anzar, M. et al., Sperm Apoptosis in fresh and cryopreserved bull semen detected by flow cytometry and it's relationship with fertility, Biology of Reproduction 66: 354-360 (2002).

Arav, A. et al., New trends in gamete's cryopreservation, Molecular and Cellular Endocrinology 187:77-81 (2002).

Arts, E. et al., Evidence for the existence of lipid-diffusion barriers in the equatorial segment of human spermatozoa, Biochem J. 384:211-218 (1994).

Gadella B, et al., Dynamics in the membrane organization of the mammalian sperm cell and functionality in fertilization, Vet Quart. 21:142-146 (1999).

Garner, D. et al., Morphological and ultrastructural Characterization of mammalian spermatozoa processed for flow cytometric DNA analyses, Gamete Research 10:339-351 (1984).

Garner, D., et al., Effect of hoechst 33342 staining and laser illumination on the viability of sex-sorted bovine sperm, Theriogenology, vol. 57 No. 1, 1-810 (2002).

Garner, D. et al., Assessment of spermatozoal function using dual fluorescent staining and flow cytometric analyses, Biology of Reproduction 34:, 127-138 (1986).

Givan, A., Flow Cytometry First Principles, (1992).

Gledhill, B. et al., Flow cytometry and sorting of sperm and male germ cells, Flow Cytometry and sorting, second edition, pp. 531-551 (1990).

Graham, J. et al., Analysis of sperm cell viability, Acrosomal integrity, and Mitocondrial function using flow cytometry, Biology of Reproduction 43: 55-64 (1990).

Graham, J. et al., Effect of some Zwitter Ion buffers on freezing and storage of spermatozoa I, Bull, J. Dairy Sci 55: 372-378 (1992).

Grogan, W. et al., DNA Analysis and sorting of viable mouse testis cells, The Journal of Histochemistry and Cytochemistry, vol. 29 No. 6 pp. 738-746, (1981).

Hacker-Klom, U.B., et al., Effect of doxorubicin and 4'-epidoxorubicin on mouse spermatogenesis. Mutation Research International Journal on Mutagenesis vol. 159, pp. 39-46. 1986.

Hasler, J., Symposium: Reproductive Technology and Genetic Improvement J. Dairy Sci. 75:2857-2879 (1992).

Held, A. et al., Quasi- CW Solid- state lasers Expand their reach, Photonics Spectra, Dec. 2002.

Hinkley, R. et al., Rapid visual detection of sperm-egg fusion using the DNA-Specific Fluorochrome Hoechst 33342, Developmental Biology 118: 148-154 (1986).

Januskauskas, A. et al., Assessment of sperm quality through Fluorometry and sperm chromatin structure assay in relation to field fertility of frozen-thawed semen from Swedish AI bulls, Theriogenology 55: 947-961 (2001).

Johnson, L., A flow cytometric/ sorting method for sexing mammalian sperm validated by DNA analysis and live births, Cytometry, p. 42 of supplement, Sep. 4, 1990.

Johnson, L., Flow sorting of intact X & Y chromosome-bearing mammalian spermatozoa, The Journal of the Society for Analytical Cytology Cytometry, (1988).

Zhang, M. et al., Development of bovine embryos after in vitro fertilization of oocytes with a flow cytometrically sorted, stained and unsorted sperm from different bulls, Theriogenology 60: 1657-1663 (2003).

Jones, R. et al., Effect of Osmolality and Phosphate, "Tris", "Tes", "Mes", nd "Herpes" Hydrogen ion buffers on the motility of bull spermatozoa stored at 37 or 5° C, Ausi J. Biol. Sci.25:1047-1055 (1972).

Jones, R., Plasma membrane structures and remodelling during sperm maturation in the epididymis, Journal of Reproduciton and Fertility (1998).

Edited by Johnson, L., Boar Semen Preservation, Supplement to Reproduction in Domestic Animals (1991).

Johnson, M., The Macromolecular Organization of membranes and its bearing on events leading up to Fertilization, Journal of Reproduction and Fertility (1975).

Johnson, L., Progress towards achieving sex preselection in farm animals, USDA Agricultural Research Service, (1989).

Kordwig, V. et al., Uniform Lateral Orentation, caused by flow forces, of flat particles in flow-through systrms, The Journal of Histochemistry and Cytochemistry, vol. 25 No. 7 pp. 774-780 (1977).

Keeler, K. et al., Flow microfluorometric analysis of living spermatozoa stained with Hoechst 33342, J. Reprod.Fert. 68:205-212 (1983).

Keij, J. et al., High speed Photodamage cell sorting: An evaluation of the Zapper Prototype, Methods in cell Biology vol. 42, (1994).

Kirchhoff, C. et al., The Molecular biology of the sperm surface: Post-Testicular Membrane Remodelling, The Fate of the Male Germ Cell, (1997).

Krueger, C. et al., Low dose Insemination in synchronized gilts, Theriogenology 52: 1363-1373 (1999).

Lahdetie, J., Induction and survival of micronuclei in rat spermatids. Comparison of two meiotic micronucleus techniques using cyclophosphamide, Mutation Research, 203:47-53 (1988).

Libbus, B.et al.,Incidence of chromosome aberrations in mammalian sperm stained with Hoechst 33342 and UV-laser irradiated during flow sorting, Mutation Research, 182: 265-274 (1987).

Loken, M., Separation of viable T and B lymphocytes using a cytochemical stain, Hoechst 33342, The Journal of Histochemistry and Cytochemistry,vol. 28, No. 1, pp. 36-39 (1980).

Lucas, J.et al., Orientation measurements of microsphere doublets and metaphase chromosomes in flow, Cytometry 7:575-581 (1986).

Luttmer, S.et al.,Examination of living and fixed gametes and early embryos stained with supravital fluorochromes (Hoechst 33342 and 3,3'-dihexyloxacarocyanine Iodide), Gamete Research 15:267-283 (1986).

Maxwell, W.et al.,Physiology of spermatozoa at high dilution rates:The influence of seminal plasma, Theriogenology 52: 1353-1362 (1999).

Mazur, P., The role of Intracellular freezing in the death of cells cooled at supraoptimal rates, Cryobiology 14:251-272 (1977).

Medeiros,C. et al., Current status of sperm cryopreservation: Why isn't it better? Theriogenology 57: 327-344 (2002).

Meistrich, M.et al., "Cytogenetic" studies of spermatids of mice carrying Cattanach's translocation by flow cytometry, Chromosoma 74:141-151 (1979).

Morrell, J. et al., Offspring from inseminations with mammalian sperm stained with Hoechst 33342, either with or without flow cytometry, Mutation Research 224:177-183 (1989).

Moruzzi, J., Selecting a mammalian species for the separationof X- and Y- chromosome-bearing spermatozoa, J. Reprod. Fert. 57:319-323 (1979).

Murthi S. et al., Improved data acquisition system for digital flow cytometry, (2002).

Studt, T., MEMS-based Cell Sorter Speeds Clinical Studies, R& D Magazine, Dec. 2003: pp. 36-37 as currently presented on and printed from http;//www.rdmag.com 2 pgs.

Gwo-Bin, L.et al., Multi-cell-line micro flow cytometers with buried SU-8/SOG Optical waveguides, Feb. 2002.

Shapiro, H. M. et al., Multistation Multparameter Flow Cytometry: Some Influences of Instrumental Factors on System Performance, 1983,pp. 11-19,4,Allan R. Liss, Inc.

OcanaQuero, J.et al., Biological effects of helium-neon irradiation on acrosome reaction in bull, Scisearch Journal of Photochemistry and Photobiology, vol. 40 No. 3, pp. 294-298 (1997).

Pangawkar, G. et al., Physical and biochemical characteristics of semen in relation to fertility of Holstein-Friesian bulls, Indian vet. Med.J. vol. 13: 21-26 (1989).

Papa, S. et al., Chromatin organization in Isolated nuclei: Flow cytometric characterization employing forward and perpendicular light scatter, Cell Biochemistry and Function vol. 6: 31-38 (1988).

Parks, J. et al., Lipids of plasma membrane and outer acrosomal membrane from bovine spermatozoa, Biology of Reproduction 37:1249-1258 (1987).

Partec, Taking flow cytometry to the next generation, Catalogue 2001—2002.

Perez-Pe, R.et al., Semen plasma proteins prevent cold shock membrane damage to ram spermatozoa, Theriogenology 56 (3) : 425-434, Aug. 1, 2001, PMID: 11516122 http.//www.ncbi.nlm.nih.gov/entrez/query.fcgi?CMD=search&DB=pubmed.

Peter, A. et al., Fractionation of bovine spermatozoa for sex selection: A rapid immunomagnetic technique to remove spermatozoa that contain the H-Y antigen, Theriogenology 40:1177-1185 (1993).

Petersen, Timothy W., et al, Stability of the Breakoff Point in a High-Speed Cell Sorter The Journal of the international society for Analytical Cytology, vol. 56A No. 2, Dec. 2003.

Pinkel Dan, Flow Cytometry and Sorting Analytical Chemistry, Mar. 1982 vol. 54 No. 3.

Pinkel Dan, Cytometric Analysis of Mammalian Sperm for Induced Morphologic and DNA Content Errors; Biological Dosimetry (Cytometric Approaches to Mammalian Systems) 1984.

Pinkel, D. et al; Radiation-Induced DNA Content Variability in Mouse Sperm. Radiation Research An International Journal, vol. 95, No. 3, Sep. 1983.

Piumi, F. et al., Specific cytogenetic labeling of bovine spermatozoa bearing X or Y chromosomes using florescent in situ hybridization (FISH), Genet, Sel. vol. 33: 89-98 (2001).

Zahid, R.et al., Changes in motion characteristics, plasma membrane integrity, and acrosome morphology during cryopreservation of buffalo spermatozoa, Journal of Andrology, vol. 22 No. 2, Mar.-Apr. 2001.

Rees, William A., et al,Betaine Can Eliminate the Base Pair Composition Dependence of DNA Melting; Biochemistry 1993, 32, pp. 137-144.

Rens, W.et al.,An X-Y paint set and sperm FISH protocol that can be used for validation of cattle sperm separation procedures, Journals of Reproduction and Fertility, 121: 541-546 (2001).

Reyes, C.et al., Characterization of Secretory Proteins from cultured Cauda Epididymal Cells that significantly sustain bovine sperm motility, Molecular Reproduction and Development 63: 500-509 (2002).

Rippel,N.et al., Transcervical insemination: Effects of variation in total sperm number/dose on fertility, 83rd Annual Fall Conference for Veterinarians, Oct. 2002.

Rizzo, W. et al.,Liposome-mediated transfer of simian virus 40 DNA and minichromosome into mammalian cells, J. Gen. Virol 64:911-919 (1983).

Ruch, F ., Determination of DNA content by microfluorometry, Introduction to Quanitative Cytochemistry, pp. 281-294 (1966).

Saacke, R.et al., Semen Quality test and their relationship to fertility, 4th National Association of Animal Breeders, (1972).

Schroter, S.et al., The glycocalyx of the sperm surface, Human Reproduction Update: vol. 5, No. 4, pp. 302-313 (1999).

Sexing Technologies, Welcome to sexing Technologies, http://www.sexingtechnologies.com/ Dec. 11, 2003.

Sharp, J. et al., Radially symmetric excitation and collection optics for flow cytometric sorting of aspherical cells, Cytometry, 29:363-370 (1997).

Smith, P.et al., Characteristics of a Novel Deep Red/ Infrared Fluorescent Cell-Permeant DNA Probe, DRAQ5, in Intact human Cells Analyzed by Flow Cytometry, Confocal and Multiphoton Microscopy, Cytometry 40:280-291 (2000).

Stanger, J.et al., The Relationship between motility and the FITC-BSA binding Properties of Mouse epididymal spermatozoa, The Journal of Experimental Zoology 227: 323-327 (1983).

Stanic,P. et al.,Comparison of protective media and freezing techniques for cryopreservation of human semen, http://www.ncbi.nlm.nih.gov/entrez/query.fcgi?CMD=search&DB=pubmed , Jul. 11, 2000.

Stewart, R., Georgia Beef Challenge, Livestock Newsletter Jan.-Feb. 2002.

Takacs, T.et al.,Flow Cytometric determination of the sperm cell number in diluted bull semen samples by DNA staining method, Acta Biochim.Biophys.Hung. vol. 22 No. 1, pp. 45-57 (1987).

Thurston,L. et al., Identification of Amplified restriction fragment length polymorphism markers linked to genes controlling boar sperm viability following cryopreservation, Biology Of Reproduction 66: 545-554 (2002).

Tone,S.et al., A method of vital staining of mouse eggs using Hoechst dye, Department of Developmential Biology (1986).

Tucker,K.et al., Sperm separation techniques:Comparison of gradient products, Proceedings 2ed International workshop for Embryologists: Troubleshooting activities in the ART lab. (2002).

Van Dilla, M.et al., Measurement of Mammalian Sperm Deoxyribonucleic acid by Flow Cytometry, The journal of Histochemistry and Cytochemistry vol. 25 No. 7 pp. 763-773 (1977).

Vazquez, J.et al., Nonsurgical Uterotubal Insemination in the Mare, Reproduction: Mare vol. 44 (1998).

Vishwanath,R.et al., Storage of bovine semen in liquid and frozen state, Animal Reproduction Science 62: 23—53 (2000).

Welch,G.et al., Sex preselection: Laboratory Validation of the sperm sex ratio of Flow sorted X- and Y- sperm by sort reanal ysis for DNA, Theriogenology 52:1343-1352 (1999).

Welch, G.et al., Fluidic and optical modification to a facs IV for flow sorting of X&Y Chromosomes bearing sperm based on DNA, International Society for Analytical Cytology (1994).

Wiltshire, M.et al., A Novel Deep Red/ Low infrared fluorescent flow cytometric probe DRAQ5NO, For the Discrimination of intact nucleated cells in apoptotic cell populations, Cytometry 39: 217-223 (2000).

Woelders, H. et al., Effects of Trehalose and Sucrose, Osmolality oh the freezing medium, and cooling Rate on Viability and intactness of bull sperm after freezing and thawing, Cryobiology 35: 93-105 (1997).

Wolf, D., Lipid domains in sperm plasma membranes, Molecular Membrane Biology 12: 101-104 (1995).

Wolf, D.et al., Changes in sperm plasma membrane lipid diffusibility after hyperactivation during In vitro capacitation in the mouse, The Journal of Cell Biology, vol. 102: 1372-1377(1986).

Wolf, D.et al., Diffusion and regionalization in membranes of maturing ram spermatozoa,The Journal of Cell Biology, vol. 98:1678-1684 (1984).

XY Files, Issue 1 Jun. 1999.
XY Files, Issue 4 Aug. 2000.
XY Files, Issue 2 Oct. 1999.
XY Files, Issue 3 Mar. 2000.
XY Files, Issue 5 Mar. 2001.
XY Files, Issue 6 Mar. 2002.

Lindsey, A. C., et al., Hysteroscopic insemination of mares with low numbers of nonsorted or flow sorted spermatozoa; Equine vet. J. (2002) 34(2) 128-132.

Sharpe, Johnathan, Advances in flow cytometry for sperm sexing, Unpublished paper, 2008.

Johnson, S.K., Possibilities with today's reproductive technologies. Available online at www.sciencedirect.com; Therio 64(2005) pp. 639-656.

Brogliatti, G. et al., Pregnancy Rates and First Born Calves by Artificial Insemination using Sexed Semen in Argentina: Therio. Jan. 2, 2002, vol. 57, No. 1 . p. 369.

Palma, G. et al., Sperm Physiology: The Ability to Produce Embryos in Vitro using Semen from Bulls with a Low Non-Return Rate. Therio. p. 308.

Gottlinger, Christopher et al., Cell-Cooling in Flow Cytometry by Peltier Elements. Cytometry 7:295-297 (1986).

Abstracts: American Dairy Science Assoc., American Society of Animal Science, Jun. 22-26, 2003 Phoenix AZ. J.Anim Sci. vol. 81 Suppl.1/J. Dairy Sci. vol. 86, Suppl. 1.

Garner, Duane L., et al, Effect of Semen Dilution on Bovine Sperm Viability as Determined by Dual-DNA Staining and Flow Cytometry. J. of Andrology, vol. 18, No. 3 May/Jun. 1997.

Lindsey, A. L., et al., Hysteroscopic or rectally guided, deep-uterine insemination of mares with spermatozoa stored 18 h at either 5 °C or 15 °C prior to flow-cytometric sorting, Animal Reproduction Science, vol. 85, Issues 1-2, Jan. 2005, pp. 125-130.

Schenk, J. L., et al., Pregnancy rates in heifers and cows with cryopreserved sexed sperm: Effects of sperm numbers per inseminate, sorting pressure, and sperm storage before sorting, Theriogenology (2008), doi:10.1016/j. theriogenolology. Aug. 16, 2008.

Suh, T.K., et al., High pressure flow cytometric sorting damages sperm, Theriogenology 64 (2005) 1035-1048.

Upreti, G. C., et al., Studies on aromatic amino acid oxidase activity in ram spermatozoa: role of pyruvate as an antioxidant, Animal Reproduction Science 51 (1998) 275-287.

Schafer, D. J., et al., Comparison of progestin-based protocols to synchronize estrus and ovulation before fixed-time artificial insemination in postpartum beef cows, Journal of Animal Science Mar. 30, 2007, pp. 1-21.

Lamb, G. C., Synchronization of estrus and artificial insemination in replacement beef heifers using gonadotropin-releasing hormone, prostaglandin F2a and progesterone, Journal of Animal Science Nov. 1, 2006, vol. 84, pp. 3000-3009.

Saladarriaga, J. P., Ovarian, hormonal, and reproductive events associated with synchronization of ovulation and timed appointment breeding in Bos indicus-influenced cattle using intravaginal progesterone, gonadotropin-releasing hormone, and prostaglandin F2a, Journal of Animal Science Jan. 2007, vol. 85, pp. 151-162.

O'Brien, J. K. et al., Semen collection, characterization an preservation in a beluga (*Delphinapterus leucas*), 1st International workshop on Beluga whale research, husbandry and management in wild and captive environments Mar. 2007.

O'Brien, J. K. et al., Development of sperm sexing and associated assisted reproductive technology for sex preselection of captive bottlenose dolphins (*Tursiops truncatus*), Reproduction, Fertility and Developement 2008, 18, 319-329.

Tardif et al., Use of Hoechst 33342 stain to evaluate live fresh and frozen bull sperm by computer-assisted analysis, Journal of Andrology, vol. 19, No. 2, 1998 p. 201-206.

Parallel Chinese Application No. 200580030309.4, Office action dated Dec. 26, 2008.

Parallel European Regional Application No. 05775742.9, Office Action dated Sep. 7, 2007.

Meneze, Y, et al. Serum is not necessary in human vitro fertilization, early embryo culture and transfer, Fertility and Sterility, The American Fertility Society, vol. 42, No. 3, Nov. 1984.

Coulter Electronics, Inc., Hialeah, FL 33010, (now: Beckmann Coulter International), Coulter Epics V System, Product Reference Manual, Apr. 1984.

Sa-Ardrit, M. et al., Ultrastructural alterations of frozen-thawed Asian elephant (*Elephas maximus*) spermatozoa, International Journal of Andrology (2006) 346-352.

De Ambrogi, M. et al., Effect of storage in short- and long term commercial semen extenders on the motility, plasma membrane and chromatin integrity of boar spermatozoa, International Journal of Andrology (2006) 543-552.

Parallel European Patent Application No. 05775742.9; Office Action dated Jun. 25, 2009.

\* cited by examiner

PROCESS FOR ENRICHING A POPULATION OF SPERM CELLS

FIELD OF THE INVENTION

The present invention generally relates to the enrichment of a population of sperm cells. In particular, the present invention generally relates to the enrichment of a population of viable sperm cells without physically sorting the cells.

BACKGROUND

The fertilization of animals by artificial insemination (AI) and embryo transplant following in vitro fertilization is an established practice. In the livestock production industry, the ability to influence the reproductive outcome toward offspring having one or more desired characteristics has obvious advantages. By way of example, there would be an economic benefit in the dairy industry to preselect offspring in favor of the female sex to ensure the production of dairy cows. The separation of sperm into enriched populations of X and Y chromosome-bearing cells, known as gender enriched semen or gender enriched sperm, is one method of achieving preselected offspring.

Johnson et al. (U.S. Pat. No. 5,135,759) describe the separation of intact X and Y chromosome-bearing sperm populations according to DNA content using a flow cytometer/cell sorter into X and Y chromosome-bearing sperm enriched populations. As described, the sperm is combined with a DNA selective dye at a temperature of 30° C. to 39° C. for a period of 1 hour (39° C.) to 1.5 hours (30° C.). A flow cytometer is then used to measure the amount of fluorescent light given off when the sperm passes through a laser beam. Because the X chromosome-bearing sperm contains more DNA than the Y chromosome-bearing sperm, approximately 3% to 5% depending upon the species, the X chromosome-bearing sperm yields a greater intensity of fluorescent light than the Y chromosome-bearing sperm. Droplets containing single sperm of a predetermined fluorescent intensity are given a charge and electrostatically deflected into collection vessels. The collected, gender enriched sperm population, is then used for microinjection or artificial insemination. Notably, this method requires that the sperm cells be physically sorted to achieve the gender enriched sperm population. Physically sorting according to Johnson requires time and cost.

SUMMARY OF THE INVENTION

Among the various aspects of the present invention is a process for the preparation of sperm dispersions, sometimes referred to as suspensions, enriched with respect to a characteristic. In one embodiment, for example, the process of the present invention is used to prepare a sperm dispersion enriched with respect to X or Y-chromosome bearing sperm.

Briefly, therefore, the present invention is directed to a process for selectively decreasing the capacity of a subpopulation of sperm cells in a sperm cell dispersion to fertilize an egg. The process comprises forming a dispersion of labeled sperm cells in a liquid comprising a chemical agent or having a temperature that induces sperm immotility, wherein the presence, absence or amount of the label associated with a sperm cell indicates a genetic, proteomic, structural, or functional characteristic of a subpopulation of sperm cells in the dispersion. The process additionally comprises optically inspecting the dispersion to identify individual sperm cells as members of the subpopulation; determining the position of members of the subpopulation in the dispersion; and delivering a dose of energy to different positions within the dispersion to selectively decrease the capacity of members of the subpopulation to fertilize an egg without similarly affecting sperm cells at other positions in the dispersion.

The present invention is further directed to a process for inseminating a female mammal with an enriched sperm cell population. The process comprises forming a dispersion of labeled sperm cells in a liquid comprising a chemical agent or having a temperature that induces sperm immotility wherein the presence, absence or amount of the label associated with a sperm cell indicates a genetic, proteomic, structural, or functional characteristic of a subpopulation of sperm cells in the dispersion. The process further comprises optically inspecting the dispersion to identify individual sperm cells as members of the subpopulation; determining the position of members of the subpopulation in the dispersion; delivering a dose of energy to different positions within the dispersion to selectively decrease the capacity of members of the subpopulation to fertilize an egg without similarly affecting sperm cells at other positions in the dispersion; and thereafter inseminating a female mammal with the dispersion or a derivative thereof.

The present invention is further directed to a process for in vitro fertilization. The process comprises forming a dispersion of labeled sperm cells in a liquid comprising a chemical agent or having a temperature that induces sperm immotility wherein the presence, absence or amount of the label associated with a sperm cell indicates a genetic, proteomic, structural, or functional characteristic of a subpopulation of sperm cells in the dispersion. The process further comprises optically inspecting the dispersion to identify individual sperm cells as members of the subpopulation; determining the position of members of the subpopulation in the dispersion; delivering a dose of energy to different positions within the dispersion to selectively decrease the capacity of members of the subpopulation to fertilize an egg without similarly affecting sperm cells at other positions in the dispersion; and thereafter fertilizing an egg, in vitro, using the dispersion or a derivative thereof. The fertilized egg may thereafter be introduced into the uterus of a female mammal.

The present invention is further directed to a process for forming a frozen sperm dispersion. The process comprises forming a dispersion of labeled sperm cells in a liquid comprising a chemical agent or having a temperature that induces sperm immotility wherein the presence, absence or amount of the label associated with a sperm cell indicates a genetic, proteomic, structural, or functional characteristic of a subpopulation of sperm cells in the dispersion. The process further comprises optically inspecting the dispersion to identify individual sperm cells as members of the subpopulation; determining the position of members of the subpopulation in the dispersion; delivering a dose of energy to different positions within the dispersion to selectively decrease the capacity of members of the subpopulation to fertilize an egg without similarly affecting sperm cells at other positions in the dispersion; and thereafter cryopreserving the dispersion.

Other aspects and features of the invention will be in part apparent and in part pointed out hereinafter.

DETAILED DESCRIPTION OF THE INVENTION

Advantageously, a population of viable sperm cells may be enriched with respect to a characteristic in accordance with the present invention without physically sorting the cells. This characteristic may be, for example, whether the sperm cells carry an X or a Y chromosome. Alternatively, the characteristic may be another genetic characteristic such as the presence of a single nucleotide polymorphism ("SNP") coding for improved animal productivity (such as, for example, improved milk production) or coding for a lipid to improve cryopreservation of the selected cells. The characteristic may also be a proteomic characteristic such as a protein to improve the performance of sperm, such as, for example, a protein that would improve in utero performance by improving beneficial acrosomal characteristics. The characteristic may also be a structural characteristic, such as, for example, acrosomal integrity, or a functional characteristic, such as, for example, progressive motility.

Enrichment of a sperm cell population with respect to the genetic, proteomic, structural, or functional characteristic may be achieved, for example, by labeling sperm cells in the population having (or, alternatively, lacking) the characteristic, rendering the sperm cells substantially immotile, and selectively dosing the immotile sperm cells with a dose of energy to decrease the viability of the dosed cells or at least decrease the capacity of the dosed cells to fertilize an egg in vitro or in vivo (i.e., after insemination). Because the sperm cells in the dispersion, sometimes referred to as a suspension, are substantially immotile and selectively labeled, the energy beam may be delivered to a specific position in the dispersion to dose an individual sperm cell; by repeating this process step, i.e., individually dosing immotile sperm cells at discrete positions in the dispersion, a subpopulation of sperm cells having a desired characteristic in the dispersion may be effectively enriched, for example, with respect to the percentage of cells of the subpopulation having the desired characteristic; with respect to the percentage of offspring having a certain genetic or proteomic characteristic as a result of being produced by fertilization with the sperm cells; or with respect to both.

In any event, the population of sperm cells may be enriched for a particular subpopulation without physically separating cells having the desired characteristic from those lacking the desired characteristic (i.e., without separating the dosed cells from the non-dosed cells). Optionally, further enrichment of the cells may be achieved by additionally purifying the cells by physically separating the dosed and non-dosed cells into separate subpopulations according to methods described below.

Sperm Cell Dispersion

Density of the Sperm Cells

In general, sperm cell dispersions having a population that may be enriched in some characteristic may be prepared with a wide range of sperm cell densities. Typically, however, the sperm cell density will be at least about $1 \times 10^3$ sperm/ml, and generally not in excess of about $5 \times 10^{10}$ sperm/ml, and more preferably not in excess of about $5 \times 10^8$ sperm/ml of dispersion. For example, in one embodiment the dispersions may contain spermatozoa in a "relatively low" density, i.e., in a density of less than about $1 \times 10^7$ sperm/ml, preferably less than about $1 \times 10^6$ sperm/ml, more preferably about $1 \times 10^3$ to about $5 \times 10^6$ sperm/ml, still more preferably about $1 \times 10^3$ to about $1 \times 10^6$ sperm/ml, even more preferably about $1 \times 10^4$ to about $1 \times 10^5$ sperm/ml, and most preferably about $1 \times 10^5$ sperm/ml of dispersion. In an alternative embodiment, the dispersions may contain spermatozoa in an "intermediate" density, i.e., in a density of about $1 \times 10^7$ to about $1 \times 10^8$ sperm/ml of dispersion. In yet another alternative embodiment, the dispersions may contain spermatozoa in a "relatively high" density, i.e., in a density of at least about $1 \times 10^8$ sperm/ml, preferably about $1 \times 10^8$ to about $5 \times 10^{10}$ sperm/ml, more preferably about $1.5 \times 10^8$ to about $2 \times 10^{10}$ sperm/ml, even more preferably about $1.5 \times 10^8$ to about $2 \times 10^8$ sperm/ml, and still more preferably about $1.5 \times 10^8$ sperm/ml of dispersion. Thus, for example, the dispersions may contain at least about $0.04 \times 10^6$ sperm/ml of dispersion in one embodiment; at least about $1 \times 10^6$ in another embodiment; at least about $1.5 \times 10^6$ in another embodiment; at least about $2 \times 10^6$ in another embodiment; at least about $3 \times 10^6$ in another embodiment; at least about $0.5 \times 10^7$ in another embodiment; at least about $1 \times 10^7$ in another embodiment; at least about $1.25 \times 10^7$ in another embodiment; at least about $2 \times 10^7$ in another embodiment; at least about $3 \times 10^7$ in another embodiment; at least about $4 \times 10^7$ in another embodiment; at least about $5 \times 10^7$ in another embodiment; at least about $6 \times 10^7$ in another embodiment; at least about $7.0 \times 10^7$ in another embodiment; at least about $8 \times 10^7$ in another embodiment; at least about $9 \times 10^7$ in another embodiment; at least about $10 \times 10^7$ in another embodiment; at least about $11 \times 10^7$ in another embodiment; at least about $12 \times 10^7$ in another embodiment; at least about $1.0 \times 10^8$ in another embodiment; at least about $1.25 \times 10^8$ in another embodiment; at least about $1.5 \times 10^8$ in another embodiment; at least about $1.75 \times 10^8$ in another embodiment; at least about $2.0 \times 10^8$ in another embodiment; at least about $2.25 \times 10^8$ in another embodiment; at least about $2.5 \times 10^8$ in another embodiment; at least about $2.75 \times 10^8$ in another embodiment; at least about $3 \times 10^8$ in another embodiment; at least about $5 \times 10^8$ in another embodiment; at least about $7.0 \times 10^8$ in another embodiment; or even at least about $8 \times 10^8$ sperm/ml of dispersion. In an alternative embodiment, the dispersion may contain less than about $9 \times 10^5$, less than about $7 \times 10^5$, less than about $5 \times 10^5$, less than about $2 \times 10^5$, less than about $1 \times 10^5$, less than about $1 \times 10^4$, or even less than about $1 \times 10^3$ sperm/ml of dispersion.

The density of spermatozoa may vary based upon a number of factors, including, for example, the variations among different species of mammals, variations among the mammals of a single species, and even variations among different ejaculates of a single mammal. For example, bovine spermatozoa may be in a dispersion at a higher density, but typically in a smaller volume, such as for example $0.5 \times 10^6$ sperm/ml to about $8 \times 10^7$ sperm/ml in a volume of about 0.5 ml to about 25 ml. Swine spermatozoa, however, may be in a dispersion at a lower density, but typically in a greater volume, such as for example $0.04 \times 10^6$ sperm/ml to about $1 \times 10^7$ sperm/ml in a volume of about 50 ml to about 250 ml.

The density of spermatozoa in the sperm dispersions may also depend upon the method by which the sperm cells may be subsequently enriched or sorted. For example, the sperm cells may be sorted using flow cytometry as described in U.S. Patent Application Publication No. US 2005/0112541, the content of which is hereby incorporated herein by reference. In such an instance, the dispersion may typically be of an "intermediate" or "relatively high" density of spermatozoa. Other sorting or enrichment techniques, as described in greater detail below, may benefit from a lesser density of spermatozoa, such as a "relatively low" density of spermatozoa, labeled with a marker, such as for example the dyes and labels described herein.

The density of the spermatozoa in the sperm dispersions may also be artificially manipulated to achieve a dispersion of a specific spermatozoa density. Manipulations to the density of spermatozoa in a sperm dispersion, for example, contained in an insemination straw, may be made based upon factors such as the temperature at which the dispersion may be stored, the length of the storage period, whether the spermatozoa in the sperm dispersion are sorted or unsorted, the species of the male mammal from which the spermatozoa were collected, the fertility of the mammal from which the spermatozoa were collected, and the species of the female mammal to be inseminated.

The density of the spermatozoa in a sperm dispersion may also be affected by simply concentrating the spermatozoa, such as for example, by centrifugation. In such an instance, the dispersion would substantially separate into what is commonly referred to as a pellet (a mass of cells containing a minimal amount of fluid) and a supernatant (a soluble liquid fraction). The supernatant may then be decanted without disruption of the pellet, thereby resulting in a relatively dense pellet of sperm cells containing a minimal amount of the inhibitor, the effect being to reduce the volume of the dispersion without changing the components of the dispersion. As a result, the sperm cells of the pellet remain in an immotile state.

Immotility of the Sperm Cells

The dispersion of sperm cells contains sperm cells that have a substantially reduced motility. Substantial reduction of the motility of the sperm cells in the sperm cell dispersion may be achieved in a number of ways, including for example, by contacting the sperm cells with a motility inhibitor, by reducing the temperature of the sperm cells or the immediate environment surrounding the sperm cells (i.e., the sperm dispersion), or by a combination of both. In a preferred embodiment, sperm cells in the sperm dispersion of the present invention behave, in certain respects, in a manner characteristic of epididymal spermatozoa; for example, the sperm cells in the population are substantially immotile and/or they may have a lesser rate of endogenous respiration as compared to washed or freshly ejaculated spermatozoa. Advantageously, the immotile sperm cells, sometimes referred to as quiescent sperm cells, have the ability, upon separation from the inhibitor(s) or exposure to an increase in temperature, to behave in a manner characteristic of ejaculated spermatozoa (and not characteristic of epididymal spermatozoa) with respect to motility and, in one embodiment, with respect to motility and respiration.

In one embodiment, for example, the inhibitor, the reduction in temperature, or a combination of both reduces path velocity (sometimes referred to as motility or path motility), progressive velocity (sometimes referred to as progressive motility), or both, as measured by HTM-IVOS sperm analysis (Hamilton-Thorne HTM-IVOS computer assisted sperm analysis system Hamilton-Thorne Research, Beverly Mass.) of at least about 50% of the sperm cells in the dispersion relative to the path velocity, progressive velocity, or both of sperm cells in a fresh ejaculate of the same species. Preferably, the motility inhibitor, the reduction in temperature, or a combination of both reduces path velocity, progressive velocity, or both, as measured by HTM-IVOS sperm analysis, of at least about 60% of the sperm cells in the dispersion relative to the path velocity, progressive velocity, or both of sperm cells in a fresh ejaculate of the same species. More preferably, the motility inhibitor, the reduction in temperature, or a combination of both reduces path velocity, progressive velocity, or both, as measured by HTM-IVOS sperm analysis, of at least about 70% of the sperm cells in the dispersion relative to the path velocity, progressive velocity, or both of sperm cells in a fresh ejaculate of the same species. Still more preferably, the motility inhibitor, the reduction in temperature, or a combination of both reduces path velocity, progressive velocity, or both, as measured by HTM-IVOS sperm analysis, of at least about 80% of the sperm cells in the dispersion relative to the path velocity, progressive velocity, or both of sperm cells in a fresh ejaculate of the same species. Even more preferably, the motility inhibitor, the reduction in temperature, or a combination of both reduces path velocity, progressive velocity, or both, as measured by HTM-IVOS sperm analysis, of at least about 90% of the sperm cells in the dispersion relative to the path velocity, progressive velocity, or both of sperm cells in a fresh ejaculate of the same species. Even more preferably, the motility inhibitor, the reduction in temperature, or a combination of both reduces path velocity, progressive velocity, or both, as measured by HTM-IVOS sperm analysis, of at least about 95% of the sperm cells in the dispersion relative to the path velocity, progressive velocity, or both of sperm cells in a fresh ejaculate of the same species. Most preferably, the motility inhibitor reduces path velocity, progressive velocity, or both, as measured by an HTM-IVOS sperm analysis, of at least about 99% of the sperm cells in the dispersion relative to the path velocity, progressive velocity, or both of sperm cells in a fresh ejaculate of the same species.

A motility inhibitor may be used to substantially reduce the motility of the sperm cells in the sperm cell dispersion. The inhibitor may be any of a range of compositions having a depressive effect upon sperm motility. Such compositions include, for example, sodium channel inhibitors, such as, ouabain; compositions comprising potassium ions; and compositions comprising potassium and sodium ions. For example, relatively high concentrations of potassium ions in the dispersion tend to depress sperm motility. In general, therefore, it is preferred that the dispersion contain a source of potassium ions and that the potassium concentration in the dispersion be at least about 0.05 moles/L. More preferably, the potassium concentration is at least about 0.05 moles/L to about 0.5 moles/L. Still more preferably, the potassium concentration is at least about 0.1 moles/L to about 0.3 moles/L. Most preferably, the potassium concentration is at about 0.173 moles/L. Such dispersions will typically, but not necessarily, also contain a source of sodium ions. When sodium is present, the molar ratio of potassium to sodium is generally equal to or greater than 1:1, respectively, but will generally not exceed a molar ratio of 8:1. Preferably, the molar ratio of potassium to sodium is at least about 1.25:1. Still more preferably, the molar ratio of potassium to sodium is at least about 1.5:1. Still more preferably, the molar ratio of potassium to sodium is at least about 1.75:1. Still more preferably, the molar ratio of potassium to sodium is at least about 1.78:1. In one particular embodiment, the molar ratio of potassium to sodium is at least about 2:1. In yet another embodiment, the molar ratio of potassium to sodium is at least about 3:1. In still another embodiment, the molar ratio of potassium to sodium is at least about 4:1. In still another embodiment, the molar ratio of potassium to sodium is at least about 5:1. In still another embodiment, the molar ratio of potassium to sodium is at least about 6:1. In still another embodiment, the molar ratio of potassium to sodium is at least about 7:1. In still another embodiment, the molar ratio of potassium to sodium is at least about 8:1.

The sperm dispersion may additionally comprise an ion or source of carbon dioxide capable of enhancing the down-regulation of motility. In this embodiment, the source of carbon dioxide may be, for example, one or more carbonates. In one presently preferred embodiment, the sperm dispersion comprises $NaHCO_3$ and $KHCO_3$, thereby providing a source of potassium and sodium ions as well as an increased partial pressure of carbon dioxide (relative to the ambient atmosphere). For example, in one presently preferred embodiment, the dispersion comprises $NaHCO_3$ and $KHCO_3$ in an aqueous solution, preferably $NaHCO_3$, $KHCO_3$, and $C_6H_8O_7.H_2O$ in water; in general, the $KHCO_3$ concentration in the dispersion may be at least about 0.05 moles/L. More preferably, the $KHCO_3$ concentration is at least about 0.05 moles/L to about 0.5 moles/L. Still more preferably, the $KHCO_3$ concentration is at least about 0.1 moles/L to about 0.3 moles/L. In one particularly preferred embodiment, the dispersion is formed using a motility inhibitor comprising 0.097 moles/L of $NaHCO_3$, 0.173 moles/L of $KHCO_3$, 0.090 moles/L $C_6H_8O_7.H_2O$ in water as disclosed in Salisbury & Graves, *J. Reprod. Fertil.*, 6:351-359 (1963). The sperm cells will generally remain quiescent as long as they are exposed to the motility inhibitor(s).

When $C_6H_8O_7.H_2O$ is present in the dispersion, the molar ratio of $KHCO_3$ to $NaHCO_3$ may be as described above. The molar ratio of $KHCO_3$ to $C_6H_8O_7.H_2O$ may generally be equal to or greater than 1:1, respectively, but will generally not exceed a molar ratio of 8:1. Preferably, the molar ratio of $KHCO_3$ to $C_6H_8O_7.H_2O$ is from at least about 1.25:1. Still more preferably, the molar ratio of $KHCO_3$ to $C_6H_8O_7.H_2O$ is at least about 1.5:1. Still more preferably, the molar ratio of $KHCO_3$ to $C_6H_8O_7.H_2O$ is at least about 1.75:1. In one particular embodiment, the molar ratio of $KHCO_3$ to $C_6H_8O_7.H_2O$ is at least about 1.78:1. In another particular embodiment, the molar ratio of $KHCO_3$ to $C_6H_8O_7.H_2O$ is at least about 2:1. In yet another embodiment, the molar ratio of $KHCO_3$ to $C_6H_8O_7.H_2O$ is at least about 3:1. In still another embodiment, the molar ratio of $KHCO_3$ to $C_6H_8O_7.H_2O$ is at least about 4:1. In still another embodiment, the molar ratio of $KHCO_3$ to $C_6H_8O_7.H_2O$ is at least about 5:1. In still another embodiment, the molar ratio of $KHCO_3$ to $C_6H_8O_7.H_2O$ is at least about 6:1. In still another embodiment, the molar ratio of $KHCO_3$ to $C_6H_8O_7.H_2O$ is at least about 7:1. In still another embodiment, the molar ratio of $KHCO_3$ to $C_6H_8O_7.H_2O$ is at least about 8:1. In one particularly preferred embodiment, the dispersion is formed using an inhibitory buffer comprising 0.097 moles/L of $NaHCO_3$, 0.173 moles/L of $KHCO_3$, 0.090 moles/L $C_6H_8O_7.H_2O$ in water as disclosed in Salisbury & Graves, *J. Reprod. Fertil.*, 6:351-359 (1963). The sperm cells will generally remain quiescent as long as they are exposed to the motility inhibitor(s).

Experimental evidence to date further suggests that the overall health and other vital characteristics of sperm cells may be improved if the sperm dispersion is maintained under an atmosphere that reduces or prevents the diffusion of oxygen into the dispersion. This can be achieved by replacing the atmosphere of gas above the sperm dispersion with an atmosphere having an enhanced partial pressure of, for example, carbon dioxide, nitrogen, or other inert gases relative to ambient air. In a particular embodiment, the dispersion is maintained under an atmosphere having an enhanced partial pressure of carbon dioxide relative to air. In a preferred embodiment, the atmosphere over the dispersion has a partial pressure of carbon dioxide of at least about 0.0001 atm, but generally less than about 5 atm at atmospheric pressure. In one embodiment, the partial pressure of carbon dioxide is about 0.5 atm to about 2 atm at atmospheric pressure; in another embodiment, the partial pressure of carbon dioxide is about 0.9 atm to about 2 atm at atmospheric pressure; in another embodiment, the partial pressure of carbon dioxide is about 0.95 atm to about 2 atm at atmospheric pressure. In a particularly preferred embodiment, the atmosphere over the dispersion has a partial pressure of carbon dioxide of at least 0.9 atm; more preferably, at least about 0.95 atm.

Alternatively, or in addition to the use of a motility inhibitor, the temperature of the sperm cells or the dispersion may be altered in order to induce the sperm cells to become immotile. The temperature induced sperm immotility may be induced, for example, by reducing the temperature of the sperm cells or the dispersion to about 0° C. to about 15° C., preferably from about 1° C. to about 10° C.; more preferably from about 2° C. to about 8° C., still more preferably from about 3° C. to about 6° C., and even more preferably from about 4° C. to about 5° C., and still more preferably about 5° C. Preferably, however, the sperm cells are not exposed to temperatures that substantially detrimentally affect the viability of the cells or significantly affect the ability of the sperm cells to bind or uptake a label.

In another embodiment, the temperature of the sperm cells or the sperm dispersion may be altered such that the sperm cells or the sperm dispersion may be at a temperature within the range of about 4° C. to about 50° C.; preferably from about 7° C. to about 43° C.; more preferably from about 10° C. to about 39° C.; still more preferably from about 15° C. to about 30° C.; and most preferably from about 17° C. to about 25° C. In a particularly preferred embodiment, the temperature of the sperm cells or the surrounding dispersion may be about 4° C.

The sperm cells may be exposed to the reduced temperature, and thereby rendered substantially immotile, at any time once the cells have been obtained from the source mammal. For example, the temperature of the sperm cells may be reduced, thereby inducing sperm immotility, upon collection of the cells from the source mammal, upon combining the cells with a buffer, upon formation of the labeling mixture, including before, during, or after the labeling process, or upon formation of the dispersion of labeled cells. Generally, however, sperm immotility may be induced by a reduction in temperature prior to the optical inspection of the dispersion.

For example, the temperature of the sperm cells may be reduced (i.e., sperm immotility may be induced) subsequent to labeling of the cells, thereby allowing for labeling to occur at a more preferred temperature as discussed below. In a preferred embodiment, the temperature of the sperm cells or surrounding dispersion may be reduced (i.e., sperm immotility may be induced) subsequent to labeling and prior to optical inspection of the cells.

Exposure of the sperm cells to the inhibitor, to the reduced temperature, or to a combination of both induces the sperm cells to become immotile. In one embodiment, for example, the motility inhibitor, the reduction in temperature, or a combination of both reduces the motility, progressive motility, or both of at least 60% of the sperm cells in the dispersion relative to the motility, progressive motility, or both of sperm cells in a fresh ejaculate of the same species. Preferably, the motility inhibitor, the reduction in temperature, or a combination of both reduces the motility, progressive motility, or both of at least 70% of the sperm cells in the dispersion relative to the motility, progressive motility, or both of sperm cells in a fresh ejaculate of the same species. More preferably, the motility inhibitor, the reduction in temperature, or a combination of both reduces the motility, progressive motility, or both of at least 80% of the sperm cells in the dispersion relative to the motility, progressive motility, or both of sperm cells in a fresh ejaculate of the same species. Preferably, the motility inhibitor, the reduction in temperature, or a combination of both reduces the motility, progressive motility, or both of at least 90% of the sperm cells in the dispersion relative to the motility, progressive motility, or both of sperm cells in a fresh ejaculate of the same species. Preferably, the motility inhibitor, the reduction in temperature, or a combination of both reduces the motility, progressive motility, or both of at least 99% of the sperm cells in the dispersion relative to the motility, progressive motility, or both of sperm cells in a fresh ejaculate of the same species.

The cells are preferably rendered immotile, regardless of the method used, for a time sufficient to allow for the optical inspection of the dispersion, the determination of the position of the member cells of the subpopulation; and the dosing of the member cells of the subpopulation with an energy source. If it is desired to physically separate the dosed from the non-dosed cells, it may also be preferred to maintain the sperm cells in an immotile state through this process step. Similarly, if the sperm cells are to be cryopreserved, they may be maintained in an immotile state through the cryopreservation step (independent of whether the dosed cells are physically separated from the non-dosed cells prior to cryopreservation). In a preferred embodiment, the cells are kept immotile through the step of cryopreservation.

Immotile cells may be returned to an active state, i.e., behavior characteristic of fresh ejaculate, by separating the cells from the motility inhibitor, exposing them to air, increasing the temperature of the cells or cell dispersion (preferably to the typical temperature of freshly ejaculated spermatozoa), by dilution with physiological saline (Salisbury et al., 1963) or a buffer such as a TCA buffer or PBS, or by any combination of the above, depending upon, for example, the method used to induce immotility. Typically, at least about 20%, preferably at least about 50%, more preferably at least about 60%, still more preferably at least about 70%, even more preferably at least about 80%, even more preferably at least about 90%, still more preferably at least about 95%, and most preferably at least about 99% of the cells returned to an active state (i.e., reactivated cells) will have a path velocity, progressive velocity, or both, as measured by HTM-IVOS sperm analysis, that is at least about 50%, preferably at least about 60%, more preferably at least about 70%, still more preferably at least about 80%, even more preferably at least about 90%, even more preferably at least about 95%, and most preferably at least about 99% of the path velocity, progressive velocity, or both of the sperm cells prior to being combined with the motility inhibitor (i.e., of sperm cells of a fresh ejaculate).

Collection of the Cells from a Mammal

Various methods of collection of viable sperm are known. Such methods include, for example, the gloved-hand method, use of an artificial vagina, and electro-ejaculation.

At the time of collection, or subsequently, the collected sperm may be combined with any of a number of various buffers that are compatible with sperm, such as TCA, HEPES, PBS, or any of the other buffers disclosed in U.S. Patent Application Publication No. US 2005/0003472, the content of which is hereby incorporated herein by reference. For example, a bovine semen sample typically containing about 0.5 to about 10 billion sperm cells per milliliter may be collected directly from the source mammal into a vessel containing a buffer to form a sperm suspension. Alternatively, the semen sample may be collected into an empty vessel and then subsequently contacted with a buffer within several minutes to hours after collection to form the sperm suspension.

Alternatively, the sperm cells may be collected and contacted with a motility inhibitor in lieu of or in addition to a buffer, thereby forming a sperm dispersion. The sperm cells may be collected directly from the animal into a vessel containing a motility inhibitor to form the sperm dispersion, or alternatively, may be collected into an empty vessel and then subsequently combined with a motility inhibitor within several minutes (or even hours) of collection to form the sperm dispersion.

The sperm dispersion may also contain a range of other additives to enhance sperm viability. Exemplary additives include protein sources, antibiotics, growth factors, and compositions that regulate oxidation/reduction reactions intracellularly and/or extracellularly. Examples of each of these additives are well known in the art, as demonstrated in the disclosure of, for example, U.S. Application Ser. Nos. 60/557,407 and 11/092,313, the content of each of which is hereby incorporated herein by reference.

Labeling of the Cells

Sperm cells may be labeled with any of a number of different labels, including labels that bind to the exterior of the cell (such as, for example, fluorescently labeled antibodies) as well as labels that cross the cell membrane and bind to the internal contents of the cell (such as, for example, fluorescent DNA selective dyes). Generally, the labeling process comprises contacting the sperm cells with a concentration of label (thereby forming a labeling mixture, sometimes referred to as a staining mixture), at a temperature and pH that allow for rapid and efficient binding or uptake of the label, for a time sufficiently long to obtain the desired degree of labeling, without substantially affecting the viability of the cells.

The sperm may be in the form of neat semen, or alternatively, a sperm-containing semen derivative obtained by centrifugation or the use of other means to separate semen into fractions. The sperm cells are then contacted or otherwise combined with the label to form a labeling mixture; optionally, the label may be in the form of a solid or a solution. Generally, however, the label, the sperm cells, or both are in a medium such as a buffer.

In one embodiment, the sperm cells are combined with a buffer to form a sperm suspension. Any of a number of various buffers that are compatible with sperm, such as for example, TCA, HEPES, PBS, or the buffers disclosed in U.S. Patent Application Publication No. US 2005/0003472 may be used. Once formed, the sperm suspension may be combined with a source of label to form a labeling mixture; optionally, the label may be in solid or liquid form and, as a further option, may additionally comprise any of the previously mentioned buffers.

In another embodiment, the label is combined with a buffer to form a labeling suspension and the labeling suspension is combined with a sperm source in the form of neat semen, a sperm-containing semen derivative, or a sperm suspension to form the labeling mixture.

In a preferred embodiment, a buffer comprising a motility inhibitor is used to form the labeling mixture. For example, the motility inhibitor may be included in the buffer used to form a sperm suspension (which is then combined with the label) or a labeling suspension (which is then combined with a source of sperm) to form the labeling mixture. In either event, the result is a sperm dispersion containing a motility inhibitor and label.

The labeling mixture may be formed by using any of a number of labels, such as for example, one or more UV or visible light excitable, DNA selective dyes, as previously described in U.S. Pat. No. 5,135,759 and WO 02/41906, each of which is hereby incorporated herein by reference. Exemplary UV light excitable, DNA selective dyes include Hoechst 33342 and Hoechst 33258, each of which is commercially available from Sigma-Aldrich (St. Louis, Mo.). Exemplary visible light excitable dyes include SYBR-14, commercially available from Molecular Probes, Inc. (Eugene, Oreg.) and bisbenzimide-BODIPY® conjugate 6-{[3-((2Z)-2-{[1-(difluoroboryl)-3,5-dimethyl-1H-pyrrol-2-yl]methylene}-2H-pyrrol-5-yl)propanoyl]amino}-N-[3-(methyl{3-[({4-[6-(4-methylpiperazin-1-yl)-1H,3'H-2,5'-bibenzimidazol-2'-yl]phenoxy}acetyl)amino]propyl}amino)-propyl]hexanamide ("BBC") described in WO 02/41906. Each of these dyes may be used alone or in combination; alternatively, other cell permeant UV and visible light excitable dyes may be used, alone or in combination with the aforementioned dyes, provided the dye does not detrimentally affect the viability of the sperm cells to an unacceptable degree when used in concentrations which enable sorting as described elsewhere.

Alternatively, the labeling mixture may be formed using fluorescent polyamides, and more specifically polyamides with a fluorescent label or reporter conjugated thereto. Such labels will fluoresce when bound to nucleic acids. Examples of polyamides with a fluorescent label or reporter attached thereto include, for example, those disclosed in Best et al., *Proc. Natl. Acad. Sci. USA*, 100(21): 12063-12068 (2003); Gygi, et al., *Nucleic Acids Res.*, 30(13): 2790-2799 (2002); U.S. Pat. No. 5,998,140; U.S. Pat. No. 6,143,901; and U.S. Pat. No. 6,090,947, the contents of each of which is hereby incorporated herein by reference.

Fluorescent nucleotide sequences may also be used to label the sperm cells. Such nucleotide sequences fluoresce when hybridized to a nucleic acid containing a target or complementary sequence, but are otherwise non-fluorescent when in a non-hybridized state. Such oligonucleotides are disclosed, for example, in U.S. Patent Application Publication No. 2003/0113765 (hereby incorporated herein by reference).

Sex specific antibodies may also be used to label the sperm cells in a labeling mixture. In this embodiment, for example, a sex specific antibody may be conjugated with a fluorescent moiety (or equivalent reporter molecule). Because the antibody binds to antigens present on only an X chromosome-bearing or, alternatively, a Y chromosome-bearing cell, such cells can be selectively identified based upon their fluorescence (versus the non-fluorescence of an unlabeled cell). Moreover, more than one sex specific antibody, each antibody having a different fluorescent moiety attached thereto, may be used simultaneously. This allows for differentiation of X chromosome-bearing and Y chromosome-bearing cells based upon the differing fluorescence of each.

Luminescent, color-selective nanocrystals may also be used to label sperm cells in a labeling mixture. Also referred to as quantum dots, these particles are well known in the art, as demonstrated by U.S. Pat. No. 6,322,901 and U.S. Pat. No. 6,576,291, each of which is hereby incorporated herein by reference. These nanocrystals have been conjugated to a number of biological materials, including for example, peptides, antibodies, nucleic acids, streptavidin, and polysaccharides, (see, for example, U.S. Pat. Nos. 6,207,392; 6,423,551; 5,990,479, and 6,326,144, each of which is hereby incorporated herein by reference), and have been used to detect biological targets (see, for example, U.S. Pat. Nos. 6,207,392 and 6,247,323, each of which is hereby incorporated herein by reference).

The preferred concentration of the label in the labeling mixture is a function of a range of variables which include, for example, whether the label binds to the exterior of the cell or whether it must cross the cell membrane; if it must cross the cell membrane, the permeability of the cells to the selected label; the temperature of the labeling mixture; the amount of time allowed for labeling to occur; and the degree of selectivity desired. In general, the concentration of the label is preferably sufficient to achieve the desired degree of labeling of the cells in a reasonably short period of time without substantially detrimentally affecting sperm viability. For example, the concentration of Hoechst 33342, Hoechst 33258, SYBR-14, or BBC in the labeling mixture will generally be between about 0.1 µM and about 1.0M, preferably from about 0.1 µM to about 700 µM, and more preferably from about 100 µM to about 200 µM. In a particularly preferred embodiment, the concentration of Hoechst 33342, Hoechst 33258, SYBR-14, or BBC in the staining mixture will generally be between about 400 µM to about 500 µM, and most preferably about 450 µM. Accordingly, under one set of labeling conditions, the concentration of Hoechst 33342 is preferably about 100 µM. Under another set of labeling conditions, the concentration of Hoechst 33342 is about 150 µM. Under still another set of labeling conditions the concentration is preferably about 200 µM. Under yet another set of staining conditions the concentration of Hoechst 33342 is most preferably about 450 µM.

As another example, the concentration of a fluorescent polyamide, such as for example, those described in U.S. Application Publication No. 2001/0002314, will generally be between about 0.1 µM and about 1 mM, preferably from about 1 µM to about 1 mM, more preferably about 5 µM to about 100 µM, even more preferably about 10 µM.

Once formed, the labeling mixture may be maintained at any of a range of temperatures. For example, labeling with Hoechst 33342 or Hoechst 33258 typically will be performed within a range of about 4° C. to about 50° C. For example, the labeling mixture may be maintained at a "relatively low" temperature, i.e., a temperature of about 4° C. to about 30° C.; in this embodiment, the temperature is preferably from about 20° C. to about 30° C., more preferably from about 25° C. to about 30° C., and most preferable at about 28° C. Alternatively, the labeling mixture may be maintained within an "intermediate" temperature range, i.e., a temperature of about 30° C. to about 39° C.; in this embodiment, the temperature is preferably at about 34° C. to about 39° C., and more preferably about 37° C. In addition, the labeling mixture may be maintained within a "relatively high" temperature range, i.e., a temperature of about 40° C. to about 50° C.; in this embodiment, the temperature is preferably from about 40° C. to about 45° C., more preferably from about 40° C. to about 43° C., and most preferably at about 41° C. Selection of a preferred temperature generally depends upon a range of variables, including for example, whether the label binds to the exterior of the cell or whether it must cross the cell membrane; if it must cross the cell membrane, the permeability of the cells to the selected label; the concentration of the label(s) in the labeling mixture; the amount of time allowed for labeling to occur; and the degree of selectivity desired.

The pH of the labeling mixture may be maintained at any of a range of pH's. For example, labeling with Hoechst 33342 or Hoechst 33258 typically will be performed in a pH range of about 5.0 to about 9.0. For example, the labeling mixture may be maintained at a "slightly acidic" pH, i.e., from about 5.0 to about 7.0. In this embodiment, the pH is preferably from about 6.0 to about 7.0, more preferably from about 6.0 to about 6.5, and most preferably at about 6.2. Alternatively, the labeling mixture may be maintained at a "slightly basic" pH, i.e., from about 7.0 to about 9.0. In this embodiment, the pH is preferably from about 7.0 to about 8.0, more preferably from about 7.0 to about 7.5, and most preferably at about 7.3. Generally, however, if labeling is performed at a pH other than about 7.0, once a period of time sufficient to obtain the desired degree of labeling has occurred, the labeling mixture will be adjusted to a pH of about 7.0.

Optionally, the labeling mixture may also contain additives to enhance sperm viability. Exemplary additives include an antibiotic, a growth factor, or a composition which regulates oxidation/reduction reactions intracellularly and/or extracellularly as discussed above with respect to cell sample collection. These additives may be added to the labeling mixture in accordance therewith.

Uptake of the label by or binding of the label to the sperm cells in the labeling mixture is allowed to continue for a period of time sufficient to obtain a dispersion of sperm cells labeled to the desired degree. That period is typically a period sufficient for the label to bind to the sperm cells or the DNA of the sperm cells such that a member of a subpopulation of cells may be identified and its position in the dispersion determined. Selection of a preferred period generally depends upon a range of variables, including for example, whether the label binds to the exterior of the cell or whether it must cross the cell membrane; if it must cross the cell membrane, the permeability of the cells to the selected label; the concentration of the label(s) in the labeling mixture; the temperature of the labeling mixture; and the degree of selectivity desired. For example, the period may be a period sufficient for a fluorescent DNA selective dye to bind to the DNA of X and Y chromosome-bearing sperm cells such that they may be selected based upon the differing and measurable fluorescence intensity between the two. When, labeling with Hoechst 33342 or Hoechst 33258, for example, typically this period will be no more than about 160 minutes, preferably no more than about 90 minutes, still more preferably no more than about 60 minutes, and most preferably from about 5 minutes to about 40 minutes.

Certain labels, and in particular certain dyes, are capable of permeating the sperm cells and specifically binding the DNA without further intervention to increase the permeability of the cells. With other labels, however, it may be desirable to treat the sperm cells prior to labeling to increase the rate of permeation without unacceptably reducing viability or motility. Any suitable method known to those skilled in the art may be used. Such methods include electroporation, the use of cell-permeation-enhancing solutions, e.g., mild surfactants, or chemical shock. Where it is desired or advantageous to use other or more stringent techniques, such treatments can include the use of liposomes or many of the techniques which are used by those skilled in the art to introduce stains, dyes, genes, or vectors into living cells. These methods include, but are not limited to microinjection such as used by Gordon et al. (*Proc. Natl. Acad. Sci. USA*, 77(12): 7380-4 (1980)) and since extended to rabbits, sheep, cattle and pigs; DEAE-dextran-mediated transfer; coprecipitation with calcium phosphate; and other techniques, all of which are well known to one of skill in the art. In yet other instances, it may be desirable to centrifuge the sperm and re-suspend the centrifuged sperm in another medium, albeit based on the same or substantially the same buffer system, to remove certain components (which may have previously been added to the sperm dispersion) that may interfere with later processing steps.

One particularly preferred method of increasing the permeability of a sperm cell to a label is the well known method of optoinjection as disclosed in U.S. Pat. No. 6,753,161, the contents of which is hereby incorporated herein by reference. Generally, optoinjection is a method of transiently permeabilizing a cell by contacting the cell with a pulse of radiation. A cell is illuminated, identified and located based upon the detection of the illumination of the cell, and irradiated with a pulse of radiation sufficient to transiently permeabilize the cell. As applied to the present invention, for example, optoinjection may be used to transiently permeabilize sperm cells and thereby allow labels that bind to the internal contents of a cell (such as, for example, labels that bind to DNA or RNA) to more easily and efficiently enter into the cells. Therefore, optoinjection may be used, for example, to decrease the time needed to sufficiently label sperm cells with a fluorescent DNA selective dye, such as Hoechst 33342, Hoechst 33258, or with a fluorescent polyamide.

Optoinjection may also be used to label cells at reduced temperatures. Previously, sperm cells were generally labeled with, for example, fluorescent DNA selective dyes, at temperatures in excess of 30° C. and even 40° C., as the higher temperatures aided in increased dye uptake. While labeling at such temperatures is certainly feasible, it may be beneficial to avoid exposing the sperm cells to higher temperatures, especially for an extended period of time. Therefore, optoinjection may be used to permeabilize sperm cells, thereby allowing for the labeling of the cells at a lower temperature while still maintaining or exceeding the staining efficiency and speed typically associated with labeling at higher temperatures.

Accordingly, in one embodiment, a labeling mixture is formed comprising sperm cells, a motility inhibitor, and a dye in a concentration from about 100 μM to about 200 μM, and the staining mixture is held for a period of time at a temperature of about 41° C. In another embodiment, the motility inhibitor comprises 0.204 g $NaHCO_3$, 0.433 g $KHCO_3$, and 0.473 g $C_6H_8O_7.H_2O$ per 25 mL of purified water (0.097 moles/L of $NaHCO_3$, 0.173 moles/L of $KHCO_3$, 0.090 moles/L $C_6H_8O_7.H_2O$ in water).

In another embodiment, a labeling mixture is formed comprising sperm cells, a motility inhibitor, and a dye in a concentration of about 400 μM to about 500 μM, and the staining mixture is held for a period of time at a temperature of about 41° C. In another embodiment, the dye concentration is 450 μM. In another embodiment, the motility inhibitor comprises 0.204 g $NaHCO_3$, 0.433 g $KHCO_3$, and 0.473 g $C_6H_8O_7.H_2O$ per 25 mL of purified water (0.097 moles/L of $NaHCO_3$, 0.173 moles/L of $KHCO_3$, 0.090 moles/L $C_6H_8O_7.H_2O$ in water).

In still another embodiment, a labeling mixture is formed comprising sperm cells, a motility inhibitor, and a dye in a concentration from about 100 μM to about 200 μM, and the staining mixture is held for a period of time at a temperature of about 28° C. In another embodiment, the motility inhibitor comprises 0.204 g $NaHCO_3$, 0.433 g $KHCO_3$, and 0.473 g $C_6H_8O_7.H_2O$ per 25 mL of purified water (0.097 moles/L of $NaHCO_3$, 0.173 moles/L of $KHCO_3$, 0.090 moles/L $C_6H_8O_7.H_2O$ in water).

In yet another embodiment, a labeling mixture is formed comprising sperm cells, a motility inhibitor, and a dye in a concentration from about 400 μM to about 500 μM, and the staining mixture is held for a period of time at a temperature of about 28° C. In another embodiment, the dye concentration is 450 μM. In another embodiment, the motility inhibitor comprises 0.204 g $NaHCO_3$, 0.433 g $KHCO_3$, and 0.473 g $C_6H_8O_7.H_2O$ per 25 mL of purified water (0.097 moles/L of $NaHCO_3$, 0.173 moles/L of $KHCO_3$, 0.090 moles/L $C_6H_8O_7.H_2O$ in water).

Formation of a Dispersion of Labeled Cells

Once a labeling mixture is formed, the labeling mixture is used to form a dispersion of labeled cells, which is subsequently inspected and dosed. Such a dispersion comprises labeled sperm cells and a chemical agent that induces sperm immotility. Alternatively, or in addition to, the dispersion may comprise a liquid, such as a buffer as described above, in addition to the labeled sperm cells, and wherein the temperature of the cells or the liquid induces sperm immotility.

The labeled sperm cells may be in any of a number of forms. For example, the labeled cells may still be part of a labeling mixture. As such, the labeled cells may still be in excess or unbound label. Alternatively, the labeled cells may have been separated from any excess or unbound label, such as for example by washing the cells or by spinning down the cells, such as by centrifugation, and then separating the cells from the unbound label. In such an instance, the labeled cells will generally thereafter be combined with a buffer as discussed above with respect to collection of a cell sample. In any event, the sperm cells in the dispersion are labeled such that the absence or amount of label associated with one or more of the sperm cells allows for the identification of a genetic, proteomic, structural, or functional characteristic of a subpopulation of sperm cells in the dispersion. The sperm cells may be maintained at a temperature that induces or increases sperm immotility.

The dispersion of labeled cells may also contain a chemical agent that induces sperm immotility, such as, for example, a motility inhibitor as discussed above. The chemical agent may be added to the labeling mixture or labeled cells at any time before the optical inspection of the dispersion, such as for example, before, during, or after labeling of the sperm cells. The chemical agent may be combined with labeled cells, the labeled cells being in any of the number of forms discussed above (i.e., still in the labeling mixture or removed therefrom). In a particular embodiment, a labeling mixture is formed comprising sperm cells and a label, and then the labeling mixture is combined with the chemical agent that induces sperm immotility. Alternatively, or in addition to the chemical agent, the temperature of the labeling mixture may be reduced as discussed above in order to induce or increase sperm immotility.

Inspection, Determination, and Dosing of the Cells

Once a dispersion of labeled cells has been formed, the dispersion is optically inspected to identify individual sperm cells as members of a subpopulation, the positions of the members of the subpopulation in the dispersion are determined, and an energy beam is delivered to different positions within the dispersion to selectively dose members of the subpopulation with an energy source, thereby decreasing the viability of the dosed cells, or at least their capacity to fertilize an egg, without similarly affecting sperm cells at other positions in the dispersion.

These steps are typically performed by a device and in a manner commercially referred to as LEAP® (Laser-Enabled Analysis and Processing) Technology Platform (Cyntellect, Inc., San Diego, Calif.). Generally, this process requires that cells be labeled with a marker to identify and locate individual cells of a subpopulation of cells within a mixture or larger population of cells. The population of cells is then illuminated, allowing for the position of the individuals cells of the subpopulation to be identified. A treatment laser is then positioned in a manner such that it can emit a beam of energy to induce a change in the identified cells of the subpopulation. The induced change is usually cell death. These processes and devices are further described in U.S. Pat. Nos. 6,534,308; 6,514,722; 6,753,161; and 6,642,018, each of which is hereby incorporated herein by reference.

The energy source as used in the present invention may be any source that, when applied in a certain dose to the sperm cells, decreases the viability of the dosed cells, or at least their capacity to fertilize an egg, with minimal or no similar affect to sperm cells at other positions in the dispersion. Typically, the energy source will be in the form of an energy beam. Examples of suitable energy sources include lasers, collimated or focused non-laser light, RF energy, accelerated particles, focused ultrasonic energy, electron beams, or other radiation beams. Preferably, however, the energy source is a laser, as a laser provides the advantages of high intensity and relatively efficient use of energy in a compact size and with minimal heat generation, thereby allowing dosing of a single cell without significantly adversely affecting surrounding cells.

The cells may be placed on any surface suitable for optical inspection and dosing of the cells. Generally, such surfaces will have a horizontal surface (either a top, a bottom, or both) that is optically transparent to the energy source used to optically inspect the cells as well as the energy source used to dose members of the subpopulation. Such suitable surfaces include, for example, glass, plastics or other related polymers, and Pyrex®, and may be in the form of a flat slide, a petri dish, a single-well plate, or a multi-well plate. Examples are discussed in, for example, U.S. Pat. Nos. 6,534,308 and 6,514,722.

A sample of sperm cells may be divided into several smaller, individual samples, such as for example, by being divided into a number of individual samples for use with a multi-well plate. Each sample (for example, within each well) may be enriched for the same characteristic, thereby producing multiple samples each of which is enriched for a single characteristic. Advantageously, however, each of the samples may be enriched for a different characteristic. By way of example, a sample of sperm cells may be divided into smaller, individual samples, and each individual sample placed in one well of a 96 well plate. The individual sample of each well may then be enriched with respect to a single characteristic different from that of the samples in each of the other wells, resulting in 96 individual samples, each enriched with respect to a different characteristic.

Once the member cells of the subpopulation have been dosed with an energy source, the cell population may be further enriched by purifying the non-dosed cells (i.e., the sperm cells that were not dosed with energy). The purification of the non-dosed cells may occur by removal of either the dosed cells or the non-dosed cells from the dispersion, resulting in a subpopulation comprising non-dosed cells that are enriched for a particular characteristic. For example, if the particular characteristic is Y chromosome-bearing sperm cells, the non-dosed cells may be purified such that they comprise at least about 85% Y chromosome-bearing sperm cells; preferably at least about 90% Y chromosome-bearing sperm cells; more preferably at least about 95% Y chromosome-bearing sperm cells; even more preferably at least about 97% Y chromosome-bearing sperm cells; and most preferably at least about 99% Y chromosome-bearing sperm cells. Alternatively, if the particular desired characteristic is X chromosome-bearing sperm cells, the non-dosed cells may be purified such that they comprise at least about 85% X chromosome-bearing sperm cells; preferably at least about 90% X chromosome-bearing sperm cells; more preferably at least about 95% X chromosome-bearing sperm cells; even more preferably at least about 97% X chromosome-bearing sperm cells; and most preferably at least about 99% X chromosome-bearing sperm cells.

Removal of either the dosed or non-dosed cells from the dosed dispersion (i.e., from the larger population of sperm cells comprising both the dosed and non-dosed cells) may be achieved by any of a number of means known to those of skill in the art. Such methods include, for example, spinning down the entire dispersion, such as by centrifugation, and then removing or wicking the supernatant containing the dosed cells. Another method includes the addition of a high-density medium to the dispersion. High-density mediums that may be added to the dispersion include, for example, Percoll® and Isolate®. Generally, in a high-density separation, viable cells (i.e., non-dosed cells with respect to the present application) are able to swim to the top of the high-density medium and may thereafter be skimmed from the top of the medium, whereas damaged or dead cells (i.e., dosed cells) will remain dispersed within the high-density medium, generally within the bulk phase. Methods of using such mediums are well known in the art.

Advantageously, a dispersion of labeled cells may contain a subpopulation of cells labeled with different labels. Each label may identify a different genetic, proteomic, structural, or functional characteristic of a subpopulation of sperm cells in the dispersion. Moreover, each label may be individually detectable when bound to a sperm cell; that is to say, it is possible to separately detect the different labels. For example, the labels may each fluoresce at different wavelengths.

A different label may be added to the labeling mixture or to the dispersion of labeled cells. Alternatively, a different label may be added subsequent to any of the steps of inspection, determination, or dosing of the cells. Preferably, however, a different label will be added subsequent to the dosing of the dispersion. For example, once the members of a subpopulation of sperm cells have been dosed, the dosed dispersion (including both the dosed cells and the non-dosed cells) or a purified dosed dispersion (including only the non-dosed cells) may be labeled again, but with a different label, and the process of inspection, determination, and dosing of the cells may be repeated, generally as disclosed above, based upon the absence or amount of the different label associated with a sperm cell.

Generally, the different label may be used to identify an additional genetic, proteomic, structural, or functional characteristic of the non-dosed cells that may be different from the characteristic used to previously identify members of a subpopulation to which a dose of energy was delivered (i.e., that is different from the characteristic used to previously determine cells to be dosed or not dosed). This provides a manner of further enriching an already enriched population of cells.

By way of example, a dispersion of labeled cells may be formed using a fluorescent DNA selective dye. The dispersion may then be optically inspected to identify individual sperm cells that are X chromosome-bearing. The position of the X chromosome-bearing sperm cells may subsequently be determined, and a dose of energy may then be delivered to one or more of the X chromosome-bearing cells, thereby achieving an enriched Y chromosome-bearing viable cell population. Thereafter, the dosed dispersion (including both the dosed (X chromosome-bearing) and non-dosed (Y chromosome-bearing) cells) or a purified dosed dispersion (including only the non-dosed cells) may be labeled with another label that indicates acrosomal integrity, such as for example, phycoerythrin-conjugated peanut agglutinin (PE-PNA) that induces cell fluorescence, and in particular acrosomal fluorescence, when contacted with a cell having a reacted or damaged acrosome. The steps of optical identification and determination of the position of PE-PNA fluorescing cells may then be performed, and those cells dosed with energy. The result is a subpopulation of non-dosed cells that are Y chromosome-bearing and that have unreacted and undamaged (i.e., intact) acrosomes. See, for example, Nagy et al., Biol Reprod, 68: 1828-1835 (2003).

Cryoextension of the Cells

Once the member cells of the subpopulation have been dosed with an energy source, the entire sperm cell population (both dosed and non-dosed cells) or a subset of the population (the non-dosed cells only) may be cooled or frozen for use at a later date, for example, in fertilization procedures. In such instances, the non-dosed sperm calls may benefit from the addition of a cryoextender to minimize the impact upon viability or post-thaw motility as a result of cooling and freezing.

Generally, a cryoextender may comprise a protein source, a cryoprotectant, and a motility inhibitor. If included, a protein source may be added to provide support to the cells. The protein source may be any protein source that does not interfere with the viability of the non-dosed sperm cells and is compatible with the motility inhibitor. Examples of common protein sources include milk (including heat homogenized and skim), milk extract, egg yolk, egg yolk extract, soy protein and soy protein extract. Such proteins may be found in a concentration from about 10% (v/v) to about 30% (v/v), preferably from about 10% (v/v) to about 20% (v/v), and more preferably about 20% (v/v).

A cryoprotectant is preferably included in the cryoextender to lessen or prevent cold shock or to maintain fertility of the non-dosed sperm cells. Numerous cryoprotectants are known in the art. Selection of a cryoprotectant suitable for use with a given extender may vary, and depends upon the species from which the sperm to be frozen were obtained. Examples of suitable cryoprotectants include, for example, glycerol, dimethyl sulfoxide, ethylene glycol, propylene glycol, trehalose, Triladyl®, and combinations thereof. If included, generally, these cryoprotectants are present in the cryoextender in an amount of about 1% (v/v) to about 15% (v/v), preferably in an amount of about 5% (v/v) to about 10% (v/v), more preferably in an amount of about 7% (v/v), and most preferably in an amount of about 6% (v/v).

In addition, the cryoextender may contain a motility inhibitor as discussed above with respect to cell sample collection. The motility inhibitor(s) may be added to the cryoextender in accordance therewith.

In one particular embodiment, the cryoextender comprises a motility inhibitor, water, Triladyl®, egg yolk, and pyruvic acid. In yet another embodiment, the cryoextender comprises 0.097 moles/L of $NaHCO_3$, 0.173 moles/L of $KHCO_3$, 0.090 moles/L $C_6H_8O_7.H_2O$ in water, and 25 g Triladyl®, 25 g egg yolk, and 10 mM pyruvic acid per 75 mL of water.

In another particular embodiment, the cryoextender comprises a motility inhibitor, water, Triladyl®, and egg yolk. In yet another embodiment, the cryoextender comprises 0.097 moles/L of $NaHCO_3$, 0.173 moles/L of $KHCO_3$, 0.090 moles/L $C_6H_8O_7.H_2O$ in water, and 25 g Triladyl®, and 25 g egg yolk per 75 mL of water.

Optionally, the cryoextender may also contain an antibiotic or a composition which regulates oxidation/reduction reactions intracellularly and/or extracellularly as discussed above with respect to cell sample collection. Each of these additives may be added to the cryoextender in accordance therewith.

Cryopreservation of the entire sperm population (i.e., cryopreservation of the dosed dispersion) results in the formation of a frozen dispersion having two subpopulations, each of these subpopulations being substantially different from the other. However, each subpopulation is composed of substantially homogenous cells. That is to say, each subpopulation is comprised of cells, each of the individual cells of a single subpopulation having a characteristic common to each of the other cells in the same subpopulation. In a preferred embodiment, the dispersion is further enriched prior to cryopreservation by purifying the dispersion, based upon the presence or the absence of the common characteristic(s), according to methods described above.

Therefore, for example, the present process could be used to form a frozen sperm dispersion, the dispersion comprising a dosed subpopulation of cells, wherein all the cells of the dosed subpopulation are X chromosome-bearing cells, and a non-dosed subpopulation of cells, wherein all the cells of the non-dosed subpopulation are Y chromosome-bearing cells. According to this embodiment of the invention, the cells not receiving a dose of energy (i.e., the non-dosed Y chromosome-bearing cells) will comprise at least about 85% Y chromosome-bearing sperm cells; preferably at least about 90% Y chromosome-bearing sperm cells; more preferably at least about 95% Y chromosome-bearing sperm cells; even more preferably at least about 97% Y chromosome-bearing sperm cells; and most preferably at least about 99% Y chromosome-bearing sperm cells.

Alternatively, the present process could be used to form a frozen sperm dispersion, the dispersion comprising a dosed subpopulation of cells, wherein all the cells of the dosed subpopulation are Y chromosome-bearing cells, and a non-dosed subpopulation of cells, wherein all the cells of the non-dosed subpopulation are X chromosome-bearing cells. According to this embodiment of the invention, the non-dosed X chromosome-bearing cells will comprise at least about 85% X chromosome-bearing sperm cells; preferably at least about 90% X chromosome-bearing sperm cells; more preferably at least about 95% X chromosome-bearing sperm cells; even more preferably at least about 97% X chromosome-bearing sperm cells; and most preferably at least about 99% X chromosome-bearing sperm cells.

Fertilization

The present invention also provides for a novel process for fertilizing an egg or a female mammal, generally employing the novel process for selectively decreasing the viability of a subpopulation of sperm cells in a cell dispersion as described above.

Once the dosing of the dispersion of labeled cells has occurred, the dosed dispersion (comprising both the dosed and non-dosed cells) may be used to fertilize a female mammal. Fertilization may be performed according to any of a number of methods well known to those of skill in the art. These methods include, for example, microinjection, artificial insemination, and other methods well known to those of skill in the art. For example, a dosed dispersion comprising both the dosed and non-dosed cells, a purified dispersion comprising only the non-dosed cells, or a derivative of either may be used to inseminate a female mammal, such as for example, by artificial insemination.

Alternatively, once the dosing of the dispersion of labeled cells has occurred, the dispersion may be used to fertilize an egg, and more particularly, an egg in vitro. The fertilized egg may thereafter be introduced into the uterus of a female mammal by any of a number of means well known to those of skill in the art, such as for example embryo transplant. For example, a dosed dispersion, a purified dispersion, or a derivative of either may be used to fertilize an egg in vitro. Subsequently, the fertilized egg may be introduced into the uterus of a female mammal.

Fertilization of a female mammal or an egg in vitro using any of the aforementioned dispersions may occur shortly after dosing of the dispersion is complete, such as for example, within about 7 days, preferably within about 5 days, more preferably within about 3 days, still more preferably within about 2 days, and in a particular embodiment, within about 1 day after dosing of the dispersion is complete. In such an instance, generally the dispersion may not have been cryopreserved prior to fertilization of a female mammal or an egg in vitro (i.e., the dispersion is fresh or comprises fresh sperm cells); instead it may have been maintained in a motility inhibitor and/or may have been refrigerated at temperatures of about 2° C. to about 7° C., more preferably from about 3° C. to about 5° C., and most preferably at about 4° C. Alternatively, the dispersion may be cryopreserved and then thawed prior to fertilization of a female mammal or an egg in vitro (i.e., the dispersion is frozen/thawed or comprises frozen/thawed sperm cells). Typically, in such an instance, the cryopreserved dispersion will be thawed immediately before fertilization of a female mammal or an egg in vitro.

Having described the invention in detail, it will be apparent that modifications and variations are possible without departing from the scope of the invention defined in the appended claims.

What is claimed is:

1. A process for selectively decreasing the capacity of a subpopulation of sperm cells in a sperm cell dispersion to fertilize an egg, the process comprising: forming a dispersion of labeled sperm cells in a liquid, the liquid comprising a chemical agent that induces sperm immotility, wherein the presence, absence or amount of the label associated with a sperm cell indicates a genetic, proteomic, structural, or functional characteristic of a subpopulation of sperm cells in the dispersion, adjusting the density of the spermatozoa in the dispersion based upon variations among different species of mammals, variations among the mammals of a single species, or variations among different ejaculates of a single mammal; optically inspecting the dispersion to identify individual sperm cells as members of the subpopulation; determining the position of members of the subpopulation in the dispersion; delivering a dose of energy to different positions within the dispersion to selectively decrease the capacity of members of the subpopulation to fertilize an egg without similarly affecting sperm cells at other positions in the dispersion, and returing the non-dosed subpopulation of sperm to an active state.

2. The process of claim 1, wherein the liquid comprises a chemical agent and has a temperature that induces sperm immotility.

3. The process of claim 1, wherein the amount of the label associated with the sperm cell indicates that the sperm cell is an X chromosome-bearing sperm cell.

4. The process of claim 1, wherein the amount of the label associated with the sperm cell indicates that the sperm cell is a Y chromosome-bearing sperm cell.

5. The process of claim 1, wherein the label is selected from the group consisting of fluorescent dyes, DNA selective dyes, polyamides, oligonucleotides, and a polypeptide that binds to a surface specific characteristic of a sperm cell.

6. The process of claim 5, wherein the label is a DNA selective fluorescent dye.

7. The process of claim 6, wherein the label is Hoechst 33342, Hoechst 33258, or SYBR-14.

8. The process of claim 1, wherein the dose of energy is selected from the group consisting of radiation beams, laser beams, collimated non-laser light, focused non-laser light, and focused ultrasonic energy.

9. The process of claim 1, wherein the process further comprises purifying the sperm cells not receiving a dose of energy, the non-dosed cells.

10. The process of claim 9, wherein purifying the non-dosed cells comprises centrifuging the dispersion and removing the dosed cells.

11. The process of claim 9, wherein purifying the non-dosed cells comprises contacting the dispersion with a high-density medium.

12. The process of claim 1, wherein optically inspecting the dispersion to identify individual sperm cells as members of the subpopulation comprises optically inspecting a captured image of the cells.

13. The process of claim 1, wherein prior to optically inspecting the dispersion, the dispersion is distributed onto a multi-well plate.

14. The process of claim 13, wherein the multi-well plate is a 96 or 384 well plate.

15. The process of claim 1, wherein the dose of energy is sufficient to decrease the viability of the members of the subpopulation as compared to the viability of sperm cells not receiving a dose of energy.

16. The process of claim 1, wherein the dose of energy is sufficient to cause the death of the members of the subpopulation.

17. The process of claim 1 wherein the process further comprises cryopreserving the dispersion subsequent to delivering the dose of energy.

18. The process of claim 1 wherein the sperm cells not receiving a dose of energy comprise at least 85% X chromosome bearing sperm cells.

19. The process of claim 1 wherein the sperm cells not receiving a dose of energy comprise at least 85% Y chromosome bearing sperm cells.

20. The process of claim 1 wherein the sperm cells not receiving a dose of energy comprise at least 90% X chromosome bearing sperm cells.

21. The process of claim 1 wherein the sperm cells not receiving a dose of energy comprise at least 90% Y chromosome bearing sperm cells.

22. The process of claim 1, wherein the sperm cells not receiving a dose of energy comprise at least 95% X chromosome bearing sperm cells.

23. The process of claim 1, wherein the sperm cells not receiving a dose of energy comprise at least 95% Y chromosome bearing sperm cells.

24. The process of claim 1, wherein the sperm cells not receiving a dose of energy comprise at least 97% X chromosome bearing sperm cells.

25. The process of claim 1, wherein the sperm cells not receiving a dose of energy comprise at least 97% Y chromosome bearing sperm cells.

26. The process of claim 1, the process further comprising: labeling the dosed dispersion with an additional label, wherein the presence, absence or amount of the additional label associated with a sperm cell indicates a genetic, proteomic, structural, or functional characteristic of a second subpopulation of sperm cells in the dosed dispersion; optically inspecting the dosed dispersion to identify individual sperm cells as members of the second subpopulation; determining the position of members of the second subpopulation in the dosed dispersion; and delivering a dose of energy to different positions within the dispersion to selectively decrease the capacity of members of the second subpopulation to fertilize an egg without similarly affecting sperm cells at other positions in the dispersion.

27. The process of claim 1, wherein the temperature of the labeled sperm cells is about 0° C. to about 15° C.

28. The process of claim 1, wherein the temperature of the labeled sperm cells is about 1° C. to about 10° C.

29. The process of claim 1, wherein the temperature of the labeled sperm cells is about 2° C. to about 8° C.

30. The process of claim 1, wherein the temperature of the labeled sperm cells is about 3° C. to about 6° C.

31. The process of claim 1, wherein the temperature of the labeled sperm cells is about 4° C. to about 5° C.

32. The process of claim 1, wherein the temperature of the labeled sperm cells is about 5° C.

33. The process of claim 1, wherein the temperature of the labeled sperm cells is about 4° C.

34. The process of claim 1, wherein the density of the spermatozoa in the dispersion is between about $1 \times 10^3$ sperm/ml and about $5 \times 10^{10}$ sperm/ml.

35. The process of claim 1, wherein the density of the spermatozoa in the dispersion is between about $1 \times 10^3$ sperm/ml and about $1 \times 10^7$ sperm/ml.

36. The process of claim 1, wherein the density of the spermatozoa in the dispersion is between about $1 \times 10^7$ sperm/ml and about $1 \times 10^8$ sperm/ml.

37. The process of claim 1, wherein the density of the spermatozoa in the dispersion is between about $1 \times 10^8$ sperm/ml and about $5 \times 10^{10}$ sperm/ml.

38. A process for inseminating a female mammal with an enriched sperm cell population, the process comprising: forming a dispersion of labeled sperm cells in a liquid, the liquid comprising a chemical agent that induces sperm immotility wherein the presence, absence or amount of the label associated with a sperm cell indicates a genetic, proteomic structural, or functional characteristic of a subpopulation of sperm cells in the dispersion, adjusting the density of the spermatozoa in the dispersion based upon variations among different species of mammals, variations among the mammals of a single species, or variations among different ejaculates of a single mammal; optically inspecting the dispersion to identify individual sperm cells as members of the subpopulation; determining the position of members of the subpopulation in the dispersion; delivering a dose of energy to different positions within the dispersion to selectively decrease the capacity of members of the subpopulation to fertilize an egg without similarly affecting sperm cells at other positions in the dispersion; returing the non-dosed subpopulation of sperm to an active state; and thereafter inseminating a female mammal with the dispersion or a derivative thereof.

39. The process of any of claim 38 wherein the female mammal is a bovine, equine, or porcine.

40. The process of claim 38, wherein the insemination of the female mammal occurs within about 7 days, 5 days, 3 days, 2 days, or 1 day after the dosing of the cells is complete.

41. The process of claim 38, wherein the dispersion is not cryopreserved prior to insemination of a female mammal.

42. The process of claim 38, wherein the dispersion is cryopreserved prior to insemination of a female mammal.

43. A process for in vitro fertilization, the process comprising: forming a dispersion of labeled sperm cells in a liquid, the liquid comprising a chemical agent that induces sperm immotility wherein the presence, absence or amount of the label associated with a sperm cell indicates a genetic, proteomic structural, or functional characteristic of a subpopulation of sperm cells in the dispersion, adjusting the density of the spermatozoa in the dispersion based upon variations among different species of mammals, variations among the mammals of a single species, or variations among different ejaculates of a single mammal; optically inspecting the dispersion to identify individual sperm cells as members of the subpopulation; determining the position of members of the subpopulation in the dispersion; delivering a dose of energy to different positions within the dispersion to selectively decrease the capacity of members of the subpopulation to fertilize an egg without similarly affecting sperm cells at other positions in the dispersion; returing the non-dosed subpopulation of sperm to an active state; and thereafter fertilizing an egg, in vitro, using the dispersion or a derivative thereof.

44. The process of claim 43, wherein the fertilization of an egg, in vitro, occurs within about 7 days, 5 days, 3 days, 2 days, or 1 day after the dosing of the cells is complete.

45. The process of claim 43, wherein the process further comprises introducing the fertilized egg into the uterus of a female mammal.

46. The process of claim 43, wherein the enriched dispersion is not cryopreserved prior to fertilization of an egg.

47. The process of claim 43, wherein the enriched dispersion is cryopreserved prior to fertilization of an egg.

48. A process for forming a frozen sperm dispersion, the process comprising: forming a dispersion of labeled sperm cells in a liquid, the liquid comprising a chemical agent that induces sperm immotility wherein the presence, absence or amount of the label associated with a sperm cell indicates a genetic, proteomic structural, or functional characteristic of a subpopulation of sperm cells in the dispersion, adjusting the density of the spermatozoa in the dispersion based upon variations among different species of mammals, variations among the mammals of a single species, or variations among different ejaculates of a single mammal; optically inspecting the dispersion to identify individual sperm cells as members of the subpopulation; determining the position of members of the subpopulation in the dispersion; delivering a dose of energy to different positions within the dispersion to selectively decrease the capacity of members of the subpopulation to fertilize an egg without similarly affecting sperm cells at other positions in the dispersion; and, thereafter cryopreserving the dispersion.

49. The method of claim 48, wherein the dosed dispersion is placed into a straw before freezing.

\* \* \* \* \*

UNITED STATES PATENT AND TRADEMARK OFFICE
CERTIFICATE OF CORRECTION

PATENT NO. : 7,833,147 B2
APPLICATION NO. : 11/572376
DATED : November 16, 2010
INVENTOR(S) : Jeffrey A. Graham It is certified that error appears in the above-identified patent and that said Letters Patent is hereby corrected as shown below:

In the Claims,

Column 20, claim 1, line 32, "returing" should be replaced with -- returning --.

Column 22, claim 39, line 34, "of any" should be deleted.

Signed and Sealed this
Twenty-ninth Day of December, 2015

Michelle K. Lee
*Director of the United States Patent and Trademark Office*